US012281320B2

(12) United States Patent
Asokan et al.

(10) Patent No.: US 12,281,320 B2
(45) Date of Patent: Apr. 22, 2025

(54) METHODS AND COMPOSITIONS FOR ANTIBODY-EVADING VIRUS VECTORS

(71) Applicants: The University of North Carolina at Chapel Hill, Chapel Hill, NC (US); University of Florida Research Foundation, Incorporated, Gainsville, NC (US)

(72) Inventors: Aravind Asokan, Chapel Hill, NC (US); Patrick Havlik, Carrboro, NC (US); Mavis Agbandje-McKenna, Gainesville, FL (US); James K. Smith, Gainesville, FL (US); Mario Mietzsch, Gainesville, FL (US)

(73) Assignees: The University of North Carolina at Chapel Hill, Chapel Hill, NC (US); University of Florida Research Foundation, Incorporated, Gainsville, FL (US)

( * ) Notice: Subject to any disclaimer, the term of this patent is extended or adjusted under 35 U.S.C. 154(b) by 1248 days.

(21) Appl. No.: 16/976,408

(22) PCT Filed: Feb. 28, 2019

(86) PCT No.: PCT/US2019/020053
§ 371 (c)(1),
(2) Date: Aug. 27, 2020

(87) PCT Pub. No.: WO2019/169132
PCT Pub. Date: Sep. 6, 2019

(65) Prior Publication Data
US 2023/0242938 A1  Aug. 3, 2023

Related U.S. Application Data

(60) Provisional application No. 62/687,583, filed on Jun. 20, 2018, provisional application No. 62/636,598, filed on Feb. 28, 2018.

(51) Int. Cl.
C12N 15/86 (2006.01)
(52) U.S. Cl.
CPC .... *C12N 15/86* (2013.01); *C12N 2750/14122* (2013.01); *C12N 2750/14142* (2013.01)
(58) Field of Classification Search
CPC .................. C12N 15/86; C12N 2750/14122
See application file for complete search history.

(56) References Cited

U.S. PATENT DOCUMENTS

| 4,501,729 A | 2/1985 | Boucher et al. |
| 4,968,603 A | 11/1990 | Slamon et al. |
| 5,139,941 A | 8/1992 | Muzyczka et al. |
| 5,399,346 A | 3/1995 | Anderson et al. |
| 5,478,745 A | 12/1995 | Samulski et al. |
| 5,863,541 A | 1/1999 | Samulski et al. |
| 5,869,248 A | 2/1999 | Yuan et al. |
| 5,877,022 A | 3/1999 | Stinchcomb et al. |
| 5,882,652 A | 3/1999 | Valdes et al. |
| 5,905,040 A | 5/1999 | Mazzara et al. |
| 5,916,563 A | 6/1999 | Young et al. |
| 5,962,313 A | 10/1999 | Podsakoff et al. |
| 6,013,487 A | 1/2000 | Mitchell |
| 6,040,183 A | 3/2000 | Ferrari et al. |
| 6,083,702 A | 7/2000 | Mitchell et al. |
| 6,093,570 A | 7/2000 | Ferrari et al. |
| 6,156,303 A | 12/2000 | Russell et al. |
| 7,071,172 B2 | 7/2006 | McCown et al. |
| 7,201,898 B2 | 4/2007 | Monahan et al. |
| 7,314,912 B1 | 1/2008 | Hallek et al. |
| 2002/0192189 A1 | 12/2002 | Xiao et al. |
| 2003/0017131 A1 | 1/2003 | Park et al. |
| 2004/0013645 A1 | 1/2004 | Monahan et al. |
| 2007/0015238 A1 | 1/2007 | Snyder et al. |
| 2009/0215879 A1* | 8/2009 | Diprimio et al. .. A61K 31/7088 514/44 R |
| 2012/0322861 A1 | 12/2012 | Byrne et al. |

FOREIGN PATENT DOCUMENTS

| WO | 9005142 A1 | 5/1990 |
| WO | 9811244 A2 | 3/1998 |
| WO | 9961601 A2 | 12/1999 |
| WO | 0017377 A2 | 3/2000 |
| WO | 0028004 A1 | 5/2000 |

(Continued)

OTHER PUBLICATIONS

Agbandje et al. "The Structure of Human Parvovirus B19 at 8 Å; Resolution" Virology, 203:106-115 (1994).
Asokan et al. "The AAV Vector Toolkit: Poised at the Clinical Crossroads" Molecular Therapy, 20(4):699-708 (2012).
Bennett et al. "AAV6 K531 serves a dual function in selective receptor and antibody ADK6 recognition" Virology, 518:369-376 (2018).
Chapman et al. "Structure, sequence and Function Correlations among Parvoviruses" Virology, 194:491-508 (1993).
Chipman et al. "Cryo-electron microscopy studies of empty capsids of human parvovirus B19 complexed with its cellular receptor" Proceedings of the National Academy of Sciences USA, 93:7502-7506 (1996).
Cleves, Ann E. "Protein transport: The nonclassical ins and outs" Current Biology, 7:R318-R320 (1997).
Dimattia et al. "Structural Insight into the Unique Properties of Adeno-Associated Virus Serotype 9" Journal of Virology, 86(12):6947-6958 (2012).

(Continued)

Primary Examiner — Teresa E Knight
Assistant Examiner — James Joseph Graber
(74) Attorney, Agent, or Firm — Myers Bigel, P.A.

(57) ABSTRACT

The present disclosure provides AAV capsid proteins comprising a modification in the amino acid sequence and virus vectors comprising the modified AAV capsid protein. The disclosure also provides methods of administering the virus vectors and virus capsids of the disclosure to a cell or to a subject in vivo. This disclosure also relates to recombinant adeno associated virus (rAAV) capsid proteins comprising one or more amino acid substitutions in the 5-fold region of the rAAV capsid that result in decreased reactivity to neutralizing antibodies, and their use as gene delivery vehicles.

18 Claims, 7 Drawing Sheets

Specification includes a Sequence Listing.

(56) References Cited

FOREIGN PATENT DOCUMENTS

| WO | 0028061 A2 | 5/2000 |
|---|---|---|
| WO | 0192551 A2 | 12/2001 |
| WO | 03095647 A2 | 11/2003 |
| WO | 2006021724 A2 | 3/2006 |
| WO | 2006029319 A2 | 3/2006 |
| WO | 2006066066 A2 | 6/2006 |
| WO | 2006119137 A1 | 11/2006 |
| WO | 2007089632 A2 | 8/2007 |
| WO | 2007100465 A2 | 9/2007 |
| WO | 2008088895 A2 | 7/2008 |
| WO | 2009108274 A2 | 9/2009 |
| WO | 2010093784 A2 | 8/2010 |
| WO | 2012064960 A2 | 5/2012 |
| WO | 2014144229 A1 | 9/2014 |
| WO | 2017058892 | 4/2017 |
| WO | WO2017058892 A2 * | 4/2017 |

OTHER PUBLICATIONS

Fang et al. "Stable antibody expression at therapeutic levels using the 2A peptide" Nature Biotechnology, 23(5):584-590 (2005).
Gao et al. "Clades of Adeno-Associated Viruses Are Widely Disseminated in Human Tissues" Journal of Virology, 78(12):6381-6388 (2004).
Govindasamy et al. "Structural Insights into Adeno-Associated Virus Serotype 5" Journal of Virology, 87(20):11187-11199 (2013).
Govindasamy et al. "Structurally Mapping the Diverse Phenotype of Adeno-Associated Virus Serotype 4" Journal of Virology, 80(23):11556-11570 (2006).
Grifman et al. "Incorporation of Tumor-Targeting Peptides into Recombinant Adeno-associated Virus Capsids" Molecular Therapy, 3(6):964-975 (2001).
Gurda et al. "Capsid Antibodies to Different Adeno-Associated Virus Serotypes Bind Common Regions" Journal of Virology, 87(16):9111-9124 (2013).
Gurda et al. "Mapping a Neutralizing Epitope onto the Capsid of Adeno-Associated Virus Serotype 8" Journal of Virology, 86(15)7739-7751 (2012).
Hajitou et al. "Vascular Targeting: Recent Advances and Therapeutic Perspectives" Trends in Cardiovascular Medicine, 16(3):80-88 (2006).
Hauck et al. "Characterization of Tissue Tropism Determinants of Adeno-Associated Virus Type 1" Journal of Virology, 77(4):2786-2774 (2003).
International Preliminary Report on Patentability corresponding to International Patent Application No. PCT/US2019/020053 (7 pages) (dated Sep. 10, 2020).
Kailasan et al. "Structure of an Enteric Pathogen, Bovine Parvovirus" Journal of Virology, 89(5):2603-2614 (2015).
Koivunen et al. "Identification of Receptor Ligands with Phage Display Peptide Libraries" The Journal of Nuclear Medicine, 40:883-888 (1999).
Kuck et al. "Development of AAV serotype-specific ELISAs using novel monoclonal antibodies" Journal of Virological Methods, 140(1-2):17-24 (2007) (Abstract only).
Lerch et al. "The structure of adeno-associated virus serotype 3B (AAV-3B): Insights into receptor binding and immune evasion" Virology, 403(1):26-36 (2010).
Lux et al. "Green Fluorescent Protein-Tagged Adeno-Associated Virus Particles Allow the Study of Cytosolic and Nuclear Trafficking" Journal of Virology, 79(18):11776-11787 (2005).
McCraw et al. "structurE of adeno-associated virus-2 In Complex with Neutralizing Monoclonal antibodY A20" Virology, 431(1-2):40-49 (2012).
Mori et al. "Two novel adeno-associated viruses from cynomolgus monkey: pseudotyping characterization of capsid protein" Virology, 330:375-383 (2004).
Müller et al. "Random peptide libraries displayed on adeno-associated virus to select for targeted gene therapy vectors" Nature Biotechnology, 21(9):1040-1046 (2003).
Nam et al. "Structure of Adeno-Associated Virus Serotype 8, a Gene Therapy Vector" Journal of Virology, 81(22):12260-12271 (2007).
Ng et al. "Structural Characterization of the Dual Glycan Binding Adeno-Associated Virus Serotype 6" Journal of Virology, 84(24):12945-12957 (2010).
Shi et al. "Insertional Mutagenesis at Positions 520 and 584 of Adeno-Associated Virus Type 2 (AAV2) Capsid Gene and Generation of AAV2 Vectors with Eliminated Heparin—Binding Ability and Introduced Novel Tropism" Human Gene Therapy, 17:353-361 (2006).
Sonntag et al. "The Assembly-Activating Protein Promotes Capsid Assembly of Different Adeno-Associated Virus Serotypes" Journal of Virology, 85(23):12686-12697 (2011).
Tsao et al. "The Three-Dimensional Structure of Canine Parvovirus and Its Functional Implications" Science, 251:1456-1464 (1991).
Tseng et al. "Generation and characterization of anti-Adeno-associated virus serotype 8 (AAV8) and anti-AAV9 monoclonal antibodies" Journal of Virological Methods, 236:105-110 (2016).
Urabe et al. "Insect Cells as a Factory to Produce Adeno-Associated Virus Type 2 Vectors" Human Gene Therapy, 13:1935-1943 (2002).
Veron et al. "Humoral and Cellular Capsid-Specific Immune Responses to Adeno-Associated Virus Type 1 in Randomized Healthy Donors" The Journal of Immunology, 188:6418-6424 (2012).
Wobus et al. "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection" J. of Virology, 74:9281-9293 (2000).
Work et al. "Vascular Bed-Targeted in Vivo Gene Delivery Using Tropism-Modified Adeno-associated Viruses" Molecular Therapy, 13(4):683-693 (2006).
Xie et al. "Canine Parvovirus Capsid Structure, Analyzed at 2.9 Å Resolution" Journal of Molecular Biology, 264:497-520 (1996).
Xie et al. "The atomic structure of adeno-associated virus (AAV-2), a vector for human gene therapy" Proceedings of the National Academy of Sciences USA, 99(16):10405-10410 (2002).
Zhang et al. "Recombinant adenovirus expressing adeno-associated virus cap and rep proteins supports production of high-titer recombinant adeno-associated virus" Gene Therapy, 8:704-712 (2001).
Zhong et al. "Next generation of adeno-associated virus 2 vectors: Point mutations in tyrosines lead to high-efficiency transduction at lower doses" Proceedings of the National Academy of Sciences USA, 105(22):7827-7832 (2008).
Zhong et al. "Tyrosine-phosphorylation of AAV2 vectors and its consequences on viral intracellular trafficking and transgene expression" Virology, 381(2):194-202 (2008).
Zolotukhin et al. "Production and purification of serotype 1, 2, and 5 recombinant adeno-associated viral vectors" Methods, 28(2):158-167 (2002) (Abstract only).
Extended European Search Report corresponding to European Patent Application No. 19760157.8 (7 pages) (dated Nov. 8, 2021).
Grimm et al. "In Vitro and In Vivo Gene Therapy Vector Evolution via Multispecies Interbreeding and Retargeting of Adeno-Associated Viruses" Journal of Virology, 82(12):5887-5911 (2008).
Lisowski et al. "Selection and evaluation of clinically relevant AAV variants in a xenograft liver model" Nature, 506:382-386 (2014).
Tse et al. "Structure-guided evolution of antigenically distinct adeno-associated virus variants for immune evasion" Proceedings of the National Academy of Sciences, 114(24):E4812-E4821 (2017).
International Search Report and the Written Opinion of the International Searching Authority corresponding to International Patent Application No. PCT/US2019/020053 (10 pages) (mailed Jun. 6, 2019).
GenBank Accession No. ACW56705.1 "Sequence 5 from patent U.S. Pat. No. 7,588,772" NCBI (1 page) (Sep. 24, 2009).
GenBank Accession No. ABS91093.1 "Sequence 7 from patent U.S. Pat. No. 7,198,951" NCBI (1 page) (Aug. 10, 2007).
ACS on STN, BD Registry, 1182714-97-1 [online] [retrieved on Apr. 30, 2019], US2009215879, Aug. 27, 2009, SEQ ID No. 210.

(56) References Cited

OTHER PUBLICATIONS

ACS on STN, BD Registry, 1182714-10-8 (online) [retrieved on Apr. 30, 2019], US2009215879, Aug. 27, 2009, SEQ ID No. 7.

* cited by examiner

```
WT      ADPPTFNQSKLNSFIT
h1      ADPVGTFNEAKLHSFIT
h9      ADPVSTFNPAKLMSFIT
d5      ADPPLTFNCCKLNSFIT
d4      ADPPVTFNQDKLWSFIT
h6      ADPPVTFNSGKLCSFIT
h4      ADPIGTFNGQKLCSFIT
h5      ADPQVTFNGGKLFSFIT
h3      ADPPGTFNGGKLWSFIT
h8      ADPPGTFNGGKLASFIT
h7      ADPPGTFNRGKLQSFIT
d6      ADPPGTFNDGKLGSFIT
h2      ADPPSTFNCMKLPSFIT
h11     ADPPSTFNCPKLQSFIT
d1      ADPPSTFNLGKLSSFIT
d7      ADPPSTFNGGKLPSFIT
h12     ADPSCTFNLHKLCSFIT
h10     ADPQDTFNRTKLCSFIT
d3      ADPPTFNRTKLMSFIT
xx4     ADPFVTFNGDKLMSFIT
xx2     ADPRRTFNSRKLKSFIT
e2      ADPSVTFNSAKLQSFIT
e1      ADPVLTFNGSKLASFIT
xx3     ADPPTFNPSKLWSFIT
e3      ADPPVTFNEGKLFSFIT
e5      ADPPTFNQGKLQSFIT
xx1     ADPPGTFNGGKLGSFIT
xx5     ADPPLTFNNGKLSSFIT
hi-C    ADPRSTFNGDKLNSFIT
hi-A    ADPPTFNVDKLGSFIT
hi-B    ADPPITFNEPKLASFIT
hi-e    ADPWPTFNAGKLRSFIT
        ***   ***  ** ****
```

FIG. 1

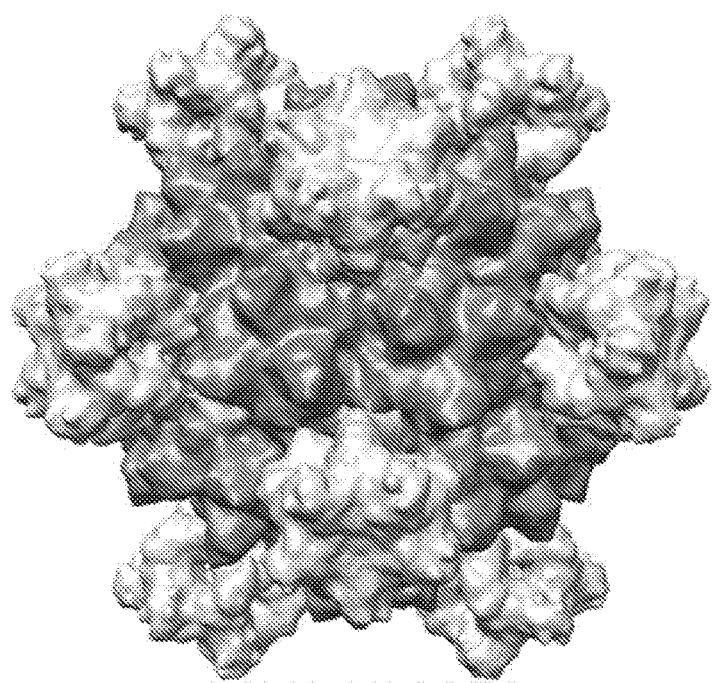
AAV8:HL2372
12.6Å
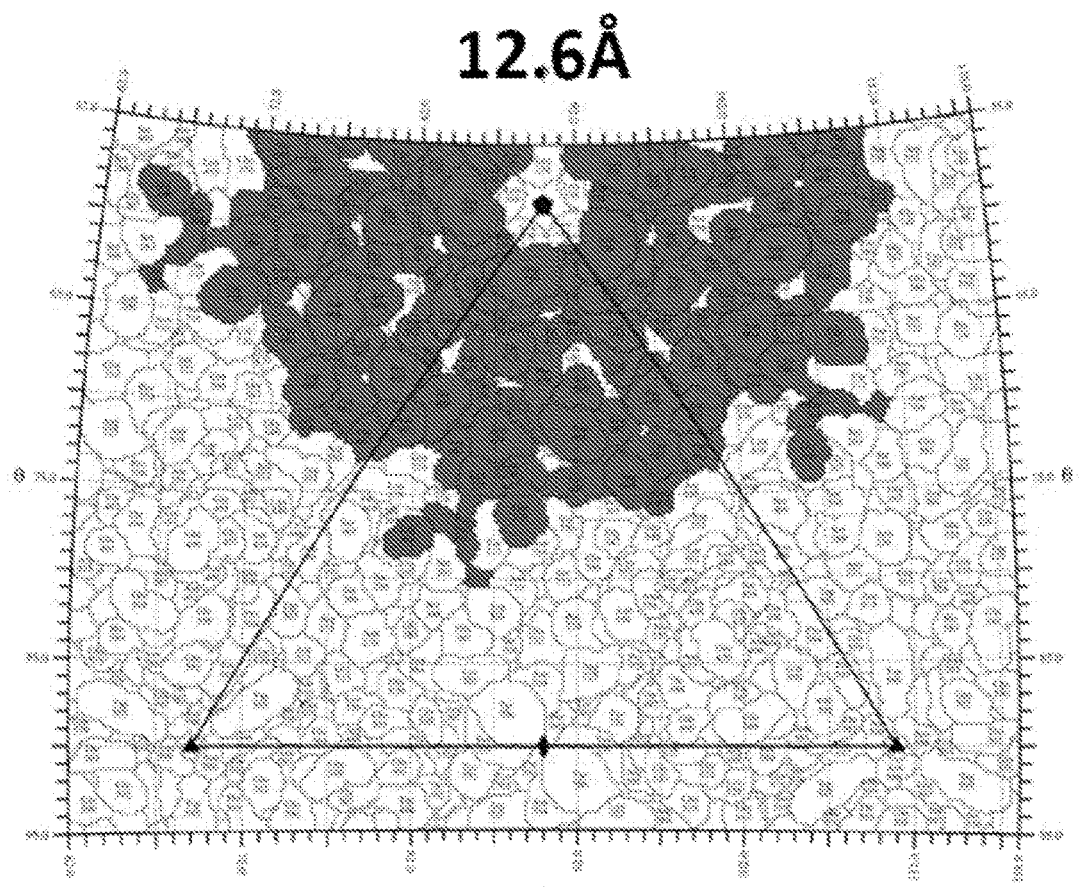
FIG. 6A

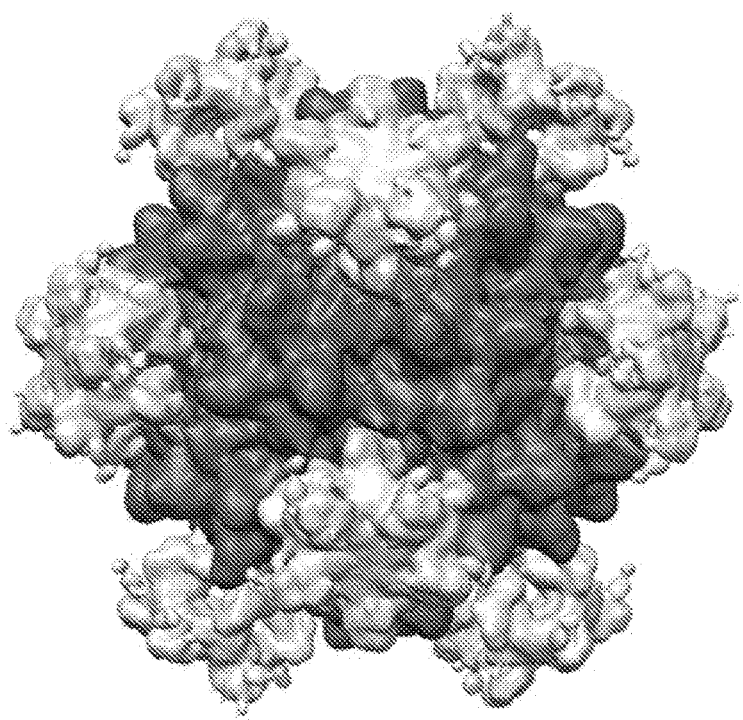
AAV9:HL2372
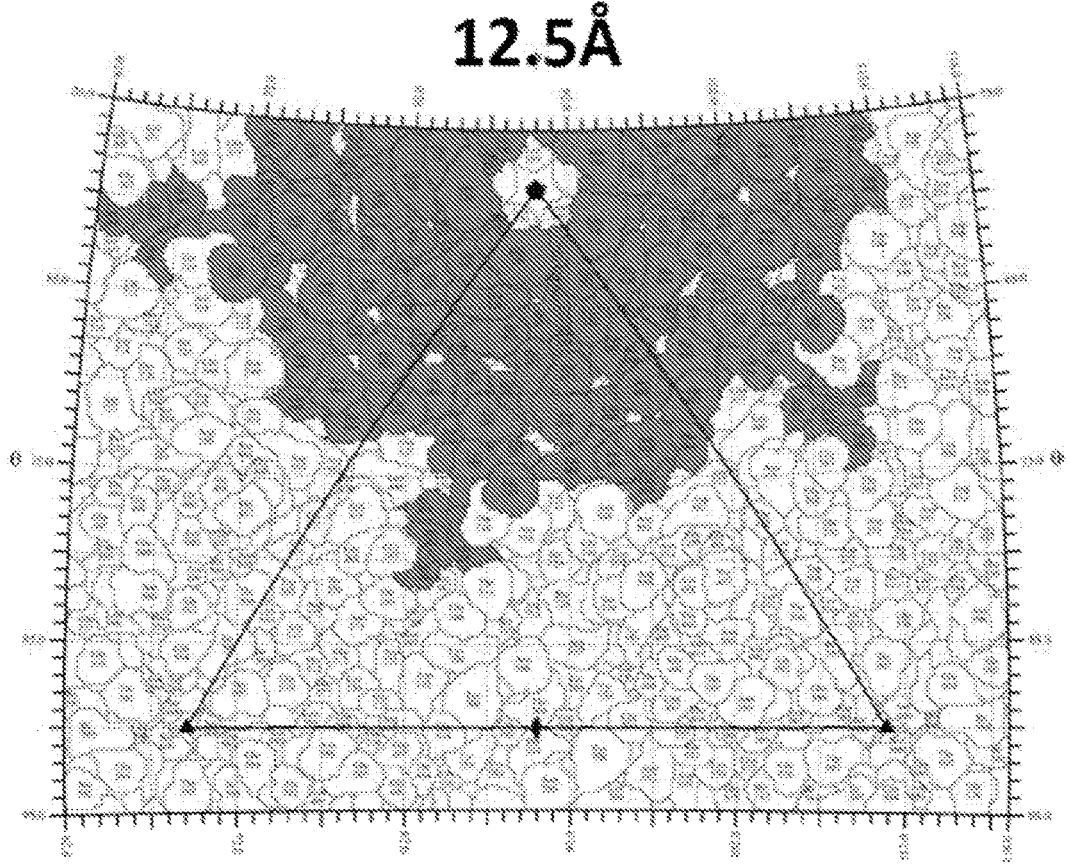
12.5Å
FIG. 6B

SEQUENCE LISTING

<160> NUMBER OF SEQ ID NOS: 262

<210> SEQ ID NO 1
<211> LENGTH: 736
<212> TYPE: PRT
<213> ORGANISM: artificial
<220> FEATURE:
<223> OTHER INFORMATION: AAV1 capsid protein

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg

```
            130                 135                 140
Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
                435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
                515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560
```

```
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: artificial
<220> FEATURE:
<223> OTHER INFORMATION: AAV2 capsid protein

<400> SEQUENCE: 2

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
```

-continued

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

```
Arg Asp Val Tyr Leu Gln Gly Pro Ile Trp Ala Lys Ile Pro His Thr
    610             615                 620

Asp Gly His Phe His Pro Ser Pro Leu Met Gly Gly Phe Gly Leu Lys
625             630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: artificial
<220> FEATURE:
<223> OTHER INFORMATION: AAV3 capsid protein

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Lys Thr Ala Pro Gly Lys Lys Gly Ala Val
    130                 135                 140

Asp Gln Ser Pro Gln Glu Pro Asp Ser Ser Ser Gly Val Gly Lys Ser
145                 150                 155                 160

Gly Lys Gln Pro Ala Arg Lys Arg Leu Asn Phe Gly Gln Thr Gly Asp
                165                 170                 175

Ser Glu Ser Val Pro Asp Pro Gln Pro Leu Gly Glu Pro Pro Ala Ala
            180                 185                 190

Pro Thr Ser Leu Gly Ser Asn Thr Met Ala Ser Gly Gly Gly Ala Pro
        195                 200                 205

Met Ala Asp Asn Asn Glu Gly Ala Asp Gly Val Gly Asn Ser Ser Gly
    210                 215                 220

Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
```

```
                660                 665                 670
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 734
<212> TYPE: PRT
<213> ORGANISM: artificial
<220> FEATURE:
<223> OTHER INFORMATION: AAV4 capsid protein

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
```

-continued

```
            290                 295                 300
Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                    325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Thr Asp Arg Asn
        370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                    405                 410                 415

Met Tyr Ala His Ser Gln Ser Leu Asp Arg Leu Met Asn Pro Leu Ile
                420                 425                 430

Asp Gln Tyr Leu Trp Gly Leu Gln Ser Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
            530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
                675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720
```

```
Glu Pro Arg Ala Ile Gly Thr Arg Tyr Leu Thr His His Leu
                725                 730

<210> SEQ ID NO 5
<211> LENGTH: 724
<212> TYPE: PRT
<213> ORGANISM: artificial
<220> FEATURE:
<223> OTHER INFORMATION: AAV5 capsid protein

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350
```

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: artificial
<220> FEATURE:
<223> OTHER INFORMATION: AAV6 capsid protein

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe

```
            405                 410                 415
Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
                705                 710                 715                 720

Tyr Thr Glu Pro Arg Pro Ile Gly Thr Arg Tyr Leu Thr Arg Pro Leu
            725                 730                 735

<210> SEQ ID NO 7
<211> LENGTH: 737
<212> TYPE: PRT
<213> ORGANISM: artificial
<220> FEATURE:
<223> OTHER INFORMATION: AAV7 capsid protein

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
```

```
                35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Gly Ala Lys Thr Ala Pro Ala Lys Lys Arg
130                 135                 140
Pro Val Glu Pro Ser Pro Gln Arg Ser Pro Asp Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
                180                 185                 190
Pro Ala Ala Pro Ser Ser Val Gly Ser Gly Thr Val Ala Ala Gly Gly
                195                 200                 205
Gly Ala Pro Met Ala Asp Asn Asn Glu Gly Ala Asp Gly Val Gly Asn
210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Glu Thr Ala Gly Ser Thr Asn Asp Asn
                260                 265                 270
Thr Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Ile Gln Val Phe Ser Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
                370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ala
                435                 440                 445
Arg Thr Gln Ser Asn Pro Gly Gly Thr Ala Gly Asn Arg Glu Leu Gln
450                 455                 460
```

-continued

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
            485                 490                 495

Gln Asn Asn Asn Ser Asn Phe Ala Trp Thr Gly Ala Thr Lys Tyr His
        500                 505                 510

Leu Asn Gly Arg Asn Ser Leu Val Asn Pro Gly Val Ala Met Ala Thr
    515                 520                 525

His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 8
<211> LENGTH: 738
<212> TYPE: PRT
<213> ORGANISM: artificial
<220> FEATURE:
<223> OTHER INFORMATION: AAV8 capsid protein

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

```
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
```

```
                500             505             510
Leu Asn Gly Arg Asn Ser Leu Ala Asn Pro Gly Ile Ala Met Ala Thr
            515                 520             525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 9
<211> LENGTH: 736
<212> TYPE: PRT
<213> ORGANISM: artificial
<220> FEATURE:
<223> OTHER INFORMATION: AAV9 capsid protein

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Ala Ala Lys Thr Ala Pro Gly Lys Lys Arg
            130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
530                 535                 540
```

-continued

```
Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 736
<212> TYPE: PRT
<213> ORGANISM: artificial
<220> FEATURE:
<223> OTHER INFORMATION: AAVrh.8 capsid protein

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175
```

-continued

```
Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ser Thr Asn Asp Asn
            260                 265                 270

Thr Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
    355                 360                 365

Ala Asp Val Phe Met Val Pro Gln Tyr Gly Tyr Leu Thr Leu Asn Asn
370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
    435                 440                 445

Arg Thr Gln Thr Thr Gly Thr Gly Thr Gln Thr Leu Ala Phe Ser
450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
    515                 520                 525

Asp Asp Asp Asp Arg Phe Phe Pro Ser Ser Gly Val Leu Ile Phe Gly
530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
```

```
            595                 600                 605
Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
                    645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 11
<211> LENGTH: 738
<212> TYPE: PRT
<213> ORGANISM: artificial
<220> FEATURE:
<223> OTHER INFORMATION: AAVrh.10 capsid protein

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
```

```
            225                 230                 235                 240
    Ile Thr Thr Ser Thr Arg Thr Trp Ala Leu Pro Thr Tyr Asn Asn His
                        245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
    305                 310                 315                 320

Ile Gln Val Lys Glu Val Thr Gln Asn Glu Gly Thr Lys Thr Ile Ala
                        325                 330                 335

Asn Asn Leu Thr Ser Thr Ile Gln Val Phe Thr Asp Ser Glu Tyr Gln
                    340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
    385                 390                 395                 400

Phe Pro Ser Gln Met Leu Arg Thr Gly Asn Asn Phe Glu Phe Ser Tyr
                    405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
                450                 455                 460

Phe Ser Gln Ala Gly Pro Asn Asn Met Ser Ala Gln Ala Lys Asn Trp
    465                 470                 475                 480

Leu Pro Gly Pro Cys Tyr Arg Gln Gln Arg Val Ser Thr Thr Leu Ser
                    485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
    545                 550                 555                 560

Met Leu Thr Ser Glu Glu Ile Lys Thr Thr Asn Pro Val Ala Thr
                        565                 570                 575

Glu Gln Tyr Gly Val Val Ala Asp Asn Leu Gln Gln Asn Ala Ala
                    580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
    625                 630                 635                 640

Gly Leu Lys His Pro Pro Gln Ile Leu Ile Lys Asn Thr Pro Val
                        645                 650                 655
```

```
Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 12
<211> LENGTH: 738
<212> TYPE: PRT
<213> ORGANISM: artificial
<220> FEATURE:
<223> OTHER INFORMATION: AAV10 capsid protein

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270
```

```
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
```

```
                    690             695             700
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                    725                 730                 735

Asn Leu

<210> SEQ ID NO 13
<211> LENGTH: 733
<212> TYPE: PRT
<213> ORGANISM: artificial
<220> FEATURE:
<223> OTHER INFORMATION: AAV11 capsid protein

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320
```

Thr Thr Val Ala Asn Asn Leu Thr Ser Thr Val Gln Ile Phe Ala Asp
            325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
            370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
            405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
            450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
            485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
            645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
            690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
            725                 730

-continued

```
<210> SEQ ID NO 14
<211> LENGTH: 742
<212> TYPE: PRT
<213> ORGANISM: artificial
<220> FEATURE:
<223> OTHER INFORMATION: AAV12 capsid protein

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270

Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365
```

-continued

Val Phe Met Val Pro Gln Tyr Gly Tyr Cys Gly Val Val Thr Gly Lys
370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
            405                 410                 415

Phe Glu Lys Val Pro Phe His Ser Met Tyr Ala His Ser Gln Ser Leu
        420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
            515                 520                 525

Pro Pro Met Ala Thr Ala Gly Ala Gly Asp Ser Asp Phe Ser Asn Ser
530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
            580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
            675                 680                 685

Ile Asp Trp Glu Ile Gln Lys Glu His Ser Lys Arg Trp Asn Pro Glu
690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
            725                 730                 735

Phe Leu Thr His His Leu
            740

<210> SEQ ID NO 15
<211> LENGTH: 733
<212> TYPE: PRT
<213> ORGANISM: artificial
<220> FEATURE:
<223> OTHER INFORMATION: AAVrh.32.33 capsid protein

<400> SEQUENCE: 15

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Thr Ser Ala Met Ser
            180                 185                 190

Ser Asp Ile Glu Met Arg Ala Ala Pro Gly Gly Asn Ala Val Asp Ala
            195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Leu Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
            370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
```

```
                    405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
            485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
            515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
            645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Tyr Gly Asn
            690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
            725                 730

<210> SEQ ID NO 16
<211> LENGTH: 736
<212> TYPE: PRT
<213> ORGANISM: artificial
<220> FEATURE:
<223> OTHER INFORMATION: Bovine AAV capsid protein

<400> SEQUENCE: 16

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
```

```
            35                  40                  45
Tyr Lys Tyr Leu Gly Pro Gly Asn Gly Leu Asp Lys Gly Asp Pro Val
 50                  55                  60
Asn Phe Ala Asp Glu Val Ala Arg Glu His Asp Leu Ser Tyr Gln Lys
 65                      70                  75                  80
Gln Leu Glu Ala Gly Asp Asn Pro Tyr Leu Lys Tyr Asn His Ala Asp
                     85                  90                  95
Ala Glu Phe Gln Glu Lys Leu Ala Ser Asp Thr Ser Phe Gly Gly Asn
                100                 105                 110
Leu Gly Lys Ala Val Phe Gln Ala Lys Lys Arg Ile Leu Glu Pro Leu
                115                 120                 125
Gly Leu Val Glu Thr Pro Asp Lys Thr Ala Pro Ala Ala Lys Lys Arg
                130                 135                 140
Pro Leu Glu Gln Ser Pro Gln Glu Pro Asp Ser Ser Ser Gly Val Gly
145                 150                 155                 160
Lys Lys Gly Lys Gln Pro Ala Arg Lys Arg Leu Asn Phe Asp Asp Glu
                165                 170                 175
Pro Gly Ala Gly Asp Gly Pro Pro Glu Gly Pro Ser Ser Gly Ala
                180                 185                 190
Met Ser Thr Glu Thr Glu Met Arg Ala Ala Gly Gly Asn Gly Gly
                195                 200                 205
Asp Ala Gly Gln Gly Ala Glu Gly Val Gly Asn Ala Ser Gly Asp Trp
210                 215                 220
His Cys Asp Ser Thr Trp Ser Glu Ser His Val Thr Thr Ser Thr
225                 230                 235                 240
Arg Thr Trp Val Leu Pro Thr Tyr Asn Asn His Leu Tyr Leu Arg Leu
                245                 250                 255
Gly Ser Ser Asn Ala Ser Asp Thr Phe Asn Gly Phe Ser Thr Pro Trp
                260                 265                 270
Gly Tyr Phe Asp Phe Asn Arg Phe His Cys His Phe Ser Pro Arg Asp
                275                 280                 285
Trp Gln Arg Leu Ile Asn Asn His Trp Gly Leu Arg Pro Lys Ser Met
                290                 295                 300
Gln Val Arg Ile Phe Asn Ile Gln Val Lys Glu Val Thr Thr Ser Asn
305                 310                 315                 320
Gly Glu Thr Thr Val Ser Asn Asn Leu Thr Ser Thr Val Gln Ile Phe
                325                 330                 335
Ala Asp Ser Thr Tyr Glu Leu Pro Tyr Val Met Asp Ala Gly Gln Glu
                340                 345                 350
Gly Ser Leu Pro Pro Phe Pro Asn Asp Val Phe Met Val Pro Gln Tyr
                355                 360                 365
Gly Tyr Cys Gly Leu Val Thr Gly Gly Ser Ser Gln Asn Gln Thr Asp
                370                 375                 380
Arg Asn Ala Phe Tyr Cys Leu Glu Tyr Phe Pro Ser Gln Met Leu Arg
385                 390                 395                 400
Thr Gly Asn Asn Phe Glu Met Val Tyr Lys Phe Glu Asn Val Pro Phe
                405                 410                 415
His Ser Met Tyr Ala His Ser Gln Ser Leu Asp Arg Leu Met Asn Pro
                420                 425                 430
Leu Leu Asp Gln Tyr Leu Trp Glu Leu Gln Ser Thr Thr Ser Gly Gly
                435                 440                 445
Thr Leu Asn Gln Gly Asn Ser Ala Thr Asn Phe Ala Lys Leu Thr Lys
                450                 455                 460
```

```
Thr Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
                485                 490                 495

Gln Gly Arg Asn Asn Ser Leu Leu His Tyr Glu Thr Arg Thr Thr Leu
            500                 505                 510

Asp Gly Arg Trp Ser Asn Phe Ala Pro Gly Thr Ala Met Ala Thr Ala
            515                 520                 525

Ala Asn Asp Ala Thr Asp Phe Ser Gln Ala Gln Leu Ile Phe Ala Gly
530                 535                 540

Pro Asn Ile Thr Gly Asn Thr Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
            595                 600                 605

Asp Arg Asp Ile Tyr Tyr Gln Gly Pro Ile Trp Ala Lys Ile Pro His
610                 615                 620

Thr Asp Gly His Phe His Pro Ser Pro Leu Ile Gly Gly Phe Gly Leu
625                 630                 635                 640

Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
            675                 680                 685

Lys Glu Arg Ser Lys Arg Trp Asn Pro Glu Val Gln Phe Thr Ser Asn
690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 17
<211> LENGTH: 743
<212> TYPE: PRT
<213> ORGANISM: artificial
<220> FEATURE:
<223> OTHER INFORMATION: Avian AAV ATCC VR-865 capsid protein

<400> SEQUENCE: 17

Met Ser Leu Ile Ser Asp Ala Ile Pro Asp Trp Leu Glu Arg Leu Val
1               5                   10                  15

Lys Lys Gly Val Asn Ala Ala Ala Asp Phe Tyr His Leu Glu Ser Gly
                20                  25                  30

Pro Pro Arg Pro Lys Ala Asn Gln Gln Thr Gln Glu Ser Leu Glu Lys
            35                  40                  45

Asp Asp Ser Arg Gly Leu Val Phe Pro Gly Tyr Asn Tyr Leu Gly Pro
        50                  55                  60

Phe Asn Gly Leu Asp Lys Gly Glu Pro Val Asn Glu Ala Asp Ala Ala
65                  70                  75                  80

Ala Leu Glu His Asp Lys Ala Tyr Asp Leu Glu Ile Lys Asp Gly His
                85                  90                  95
```

```
Asn Pro Tyr Phe Glu Tyr Asn Glu Ala Asp Arg Arg Phe Gln Glu Arg
            100                 105                 110

Leu Lys Asp Asp Thr Ser Phe Gly Gly Asn Leu Gly Lys Ala Ile Phe
            115                 120                 125

Gln Ala Lys Lys Arg Val Leu Glu Pro Phe Gly Leu Val Glu Asp Ser
        130                 135                 140

Lys Thr Ala Pro Thr Gly Asp Lys Arg Lys Gly Glu Asp Glu Pro Arg
145                 150                 155                 160

Leu Pro Asp Thr Ser Ser Gln Thr Pro Lys Lys Asn Lys Lys Pro Arg
                165                 170                 175

Lys Glu Arg Pro Ser Gly Gly Ala Glu Asp Pro Gly Glu Gly Thr Ser
            180                 185                 190

Ser Asn Ala Gly Ala Ala Pro Ala Ser Ser Val Gly Ser Ser Ile
        195                 200                 205

Met Ala Glu Gly Gly Gly Pro Val Gly Asp Ala Gly Gln Gly Ala
        210                 215                 220

Asp Gly Val Gly Asn Ser Ser Gly Asn Trp His Cys Asp Ser Gln Trp
225                 230                 235                 240

Leu Glu Asn Gly Val Val Thr Arg Thr Thr Arg Thr Trp Val Leu Pro
                245                 250                 255

Ser Tyr Asn Asn His Leu Tyr Lys Arg Ile Gln Gly Pro Ser Gly Gly
            260                 265                 270

Asp Asn Asn Asn Lys Phe Phe Gly Phe Ser Thr Pro Trp Gly Tyr Phe
        275                 280                 285

Asp Tyr Asn Arg Phe His Cys His Phe Ser Pro Arg Asp Trp Gln Arg
        290                 295                 300

Leu Ile Asn Asn Asn Trp Gly Ile Arg Pro Lys Ala Met Arg Phe Arg
305                 310                 315                 320

Leu Phe Asn Ile Gln Val Lys Glu Val Thr Val Gln Asp Phe Asn Thr
                325                 330                 335

Thr Ile Gly Asn Asn Leu Thr Ser Thr Val Gln Val Phe Ala Asp Lys
            340                 345                 350

Asp Tyr Gln Leu Pro Tyr Val Leu Gly Ser Ala Thr Glu Gly Thr Phe
        355                 360                 365

Pro Pro Phe Pro Ala Asp Ile Tyr Thr Ile Pro Gln Tyr Gly Tyr Cys
        370                 375                 380

Thr Leu Asn Tyr Asn Asn Glu Ala Val Asp Arg Ser Ala Phe Tyr Cys
385                 390                 395                 400

Leu Asp Tyr Phe Pro Ser Asp Met Leu Arg Thr Gly Asn Asn Phe Glu
                405                 410                 415

Phe Thr Tyr Thr Phe Glu Asp Val Pro Phe His Ser Met Phe Ala His
            420                 425                 430

Asn Gln Thr Leu Asp Arg Leu Met Asn Pro Leu Val Asp Gln Tyr Leu
        435                 440                 445

Trp Ala Phe Ser Ser Val Ser Gln Ala Gly Ser Ser Gly Arg Ala Leu
        450                 455                 460

His Tyr Ser Arg Ala Thr Lys Thr Asn Met Ala Ala Gln Tyr Arg Asn
465                 470                 475                 480

Trp Leu Pro Gly Pro Phe Phe Arg Asp Gln Gln Ile Phe Thr Gly Ala
                485                 490                 495

Ser Asn Ile Thr Lys Asn Asn Val Phe Ser Val Trp Glu Lys Gly Lys
            500                 505                 510
```

```
Gln Trp Glu Leu Asp Asn Arg Thr Asn Leu Met Gln Pro Gly Pro Ala
            515                 520                 525

Ala Ala Thr Thr Phe Ser Gly Glu Pro Asp Arg Gln Ala Met Gln Asn
530                 535                 540

Thr Leu Ala Phe Ser Arg Thr Val Tyr Asp Gln Thr Thr Ala Thr Thr
545                 550                 555                 560

Asp Arg Asn Gln Ile Leu Ile Thr Asn Glu Asp Glu Ile Arg Pro Thr
                565                 570                 575

Asn Ser Val Gly Ile Asp Ala Trp Gly Ala Val Pro Thr Asn Asn Gln
            580                 585                 590

Ser Ile Val Thr Pro Gly Thr Arg Ala Ala Val Asn Asn Gln Gly Ala
        595                 600                 605

Leu Pro Gly Met Val Trp Gln Asn Arg Asp Ile Tyr Pro Thr Gly Thr
    610                 615                 620

His Leu Ala Lys Ile Pro Asp Thr Asp Asn His Phe His Pro Ser Pro
625                 630                 635                 640

Leu Ile Gly Arg Phe Gly Cys Lys His Pro Pro Gln Ile Phe Ile
                645                 650                 655

Lys Asn Thr Pro Val Pro Ala Asn Pro Ser Glu Thr Phe Gln Thr Ala
                660                 665                 670

Lys Val Ala Ser Phe Ile Asn Gln Tyr Ser Thr Gly Gln Cys Thr Val
            675                 680                 685

Glu Ile Phe Trp Glu Leu Lys Lys Glu Thr Ser Lys Arg Trp Asn Pro
        690                 695                 700

Glu Ile Gln Phe Thr Ser Asn Phe Gly Asn Ala Ala Asp Ile Gln Phe
705                 710                 715                 720

Ala Val Ser Asp Thr Gly Ser Tyr Ser Glu Pro Arg Pro Ile Gly Thr
                725                 730                 735

Arg Tyr Leu Thr Lys Pro Leu
                740

<210> SEQ ID NO 18
<211> LENGTH: 736
<212> TYPE: PRT
<213> ORGANISM: artificial
<220> FEATURE:
<223> OTHER INFORMATION: AAV1 VP1 capsid protein sequence

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Thr Pro Ala Ala Val Gly Pro Thr Met Ala Ser Gly Gly Gly
                195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
                275                 280                 285
His Cys His Phe Ser Pro Arg Asp Trp Gln Arg Leu Ile Asn Asn Asn
                290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
                355                 360                 365
Asp Val Phe Met Ile Pro Gln Tyr Gly Tyr Leu Thr Leu Asn Asn Gly
                370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
                435                 440                 445
Thr Gln Asn Gln Ser Gly Ser Ala Gln Asn Lys Asp Leu Leu Phe Ser
450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
                515                 520                 525
Asp Asp Glu Asp Lys Phe Phe Pro Met Ser Gly Val Met Ile Phe Gly
530                 535                 540
Lys Glu Ser Ala Gly Ala Ser Asn Thr Ala Leu Asp Asn Val Met Ile
```

```
        545                 550                 555                 560
Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Val Gln Tyr Thr Ser Asn
                690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 19
<211> LENGTH: 735
<212> TYPE: PRT
<213> ORGANISM: artificial
<220> FEATURE:
<223> OTHER INFORMATION: AAV2 VP1 capsid protein sequence

<400> SEQUENCE: 19

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
                20                  25                  30

Lys Pro Ala Glu Arg His Lys Asp Asp Ser Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Pro Val Lys Thr Ala Pro Gly Lys Lys Arg
            130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
```

```
              180                 185                 190
Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605
```

```
Arg Asp Val Tyr Leu Gln Gly Pro Ile Trp Ala Lys Ile Pro His Thr
    610                 615                 620

Asp Gly His Phe His Pro Ser Pro Leu Met Gly Phe Gly Leu Lys
625                 630                 635                 640

His Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 20
<211> LENGTH: 736
<212> TYPE: PRT
<213> ORGANISM: artificial
<220> FEATURE:
<223> OTHER INFORMATION: AAV3 VP1 capsid protein sequence

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
            290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655
```

-continued

```
Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 734
<212> TYPE: PRT
<213> ORGANISM: artificial
<220> FEATURE:
<223> OTHER INFORMATION: AAV4 VP1 capsid protein sequence

<400> SEQUENCE: 21

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285
```

```
Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
```

```
            705                 710                 715                 720
Glu Pro Arg Ala Ile Gly Thr Arg Tyr Leu Thr His His Leu
                725                 730

<210> SEQ ID NO 22
<211> LENGTH: 724
<212> TYPE: PRT
<213> ORGANISM: artificial
<220> FEATURE:
<223> OTHER INFORMATION: AAV5 VP1 capsid protein sequence

<400> SEQUENCE: 22

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
```

```
                    340                 345                 350
Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 23
<211> LENGTH: 736
<212> TYPE: PRT
<213> ORGANISM: artificial
<220> FEATURE:
```

-continued

<223> OTHER INFORMATION: AAV6 VP1 capsid protein sequence

<400> SEQUENCE: 23

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

-continued

```
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Lys Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Leu Gln Ser Ser Ser Thr Asp Pro Ala
            580                 585                 590
Thr Gly Asp Val His Val Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 24
<211> LENGTH: 737
<212> TYPE: PRT
<213> ORGANISM: artificial
<220> FEATURE:
<223> OTHER INFORMATION: AAV7 VP1 capsid protein sequence

<400> SEQUENCE: 24

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
```

```
Lys Ala Asn Gln Gln Lys Gln Asp Asn Gly Arg Gly Leu Val Leu Pro
             35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65              70                  75                  80
Gln Gln Leu Lys Ala Gly Asp Asn Pro Tyr Leu Arg Tyr Asn His Ala
             85                  90                  95
Asp Ala Glu Phe Gln Glu Arg Leu Gln Glu Asp Thr Ser Phe Gly Gly
                 100                 105                 110
Asn Leu Gly Arg Ala Val Phe Gln Ala Lys Lys Arg Val Leu Glu Pro
             115                 120                 125
Leu Gly Leu Val Glu Glu Gly Ala Lys Thr Ala Pro Ala Lys Lys Arg
 130                 135                 140
Pro Val Glu Pro Ser Pro Gln Arg Ser Pro Asp Ser Ser Thr Gly Ile
 145                 150                 155                 160
Gly Lys Lys Gly Gln Gln Pro Ala Arg Lys Arg Leu Asn Phe Gly Gln
                 165                 170                 175
Thr Gly Asp Ser Glu Ser Val Pro Asp Pro Gln Pro Leu Gly Glu Pro
                 180                 185                 190
Pro Ala Ala Pro Ser Ser Val Gly Ser Gly Thr Val Ala Ala Gly Gly
                 195                 200                 205
Gly Ala Pro Met Ala Asp Asn Asn Glu Gly Ala Asp Gly Val Gly Asn
         210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                 245                 250                 255
Leu Tyr Lys Gln Ile Ser Ser Glu Thr Ala Gly Ser Thr Asn Asp Asn
                 260                 265                 270
Thr Tyr Phe Gly Tyr Ser Thr Pro Trp Gly Tyr Phe Asp Phe Asn Arg
             275                 280                 285
Phe His Cys His Phe Ser Pro Arg Asp Trp Gln Arg Leu Ile Asn Asn
         290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                 325                 330                 335
Asn Leu Thr Ser Thr Ile Gln Val Phe Ser Asp Ser Glu Tyr Gln Leu
             340                 345                 350
Pro Tyr Val Leu Gly Ser Ala His Gln Gly Cys Leu Pro Pro Phe Pro
             355                 360                 365
Ala Asp Val Phe Met Ile Pro Gln Tyr Gly Tyr Leu Thr Leu Asn Asn
 370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
             405                 410                 415
Phe Glu Asp Val Pro Phe His Ser Ser Tyr Ala His Ser Gln Ser Leu
                 420                 425                 430
Asp Arg Leu Met Asn Pro Leu Ile Asp Gln Tyr Leu Tyr Tyr Leu Ala
             435                 440                 445
Arg Thr Gln Ser Asn Pro Gly Gly Thr Ala Gly Asn Arg Glu Leu Gln
```

```
                450             455             460
Phe Tyr Gln Gly Gly Pro Ser Thr Met Ala Glu Gln Ala Lys Asn Trp
465                     470                     475             480

Leu Pro Gly Pro Cys Phe Arg Gln Gln Arg Val Ser Lys Thr Leu Asp
                485                     490                     495

Gln Asn Asn Asn Ser Asn Phe Ala Trp Thr Gly Ala Thr Lys Tyr His
                500                     505                     510

Leu Asn Gly Arg Asn Ser Leu Val Asn Pro Gly Val Ala Met Ala Thr
            515                     520                     525

His Lys Asp Asp Glu Asp Arg Phe Phe Pro Ser Ser Gly Val Leu Ile
            530                     535                     540

Phe Gly Lys Thr Gly Ala Thr Asn Lys Thr Thr Leu Glu Asn Val Leu
545                     550                     555                 560

Met Thr Asn Glu Glu Glu Ile Arg Pro Thr Asn Pro Val Ala Thr Glu
                565                     570                     575

Glu Tyr Gly Ile Val Ser Ser Asn Leu Gln Ala Ala Asn Thr Ala Ala
            580                     585                     590

Gln Thr Gln Val Val Asn Asn Gln Gly Ala Leu Pro Gly Met Val Trp
            595                     600                     605

Gln Asn Arg Asp Val Tyr Leu Gln Gly Pro Ile Trp Ala Lys Ile Pro
            610                     615                     620

His Thr Asp Gly Asn Phe His Pro Ser Pro Leu Met Gly Gly Phe Gly
625                     630                     635                 640

Leu Lys His Pro Pro Pro Gln Ile Leu Ile Lys Asn Thr Pro Val Pro
                645                     650                     655

Ala Asn Pro Pro Glu Val Phe Thr Pro Ala Lys Phe Ala Ser Phe Ile
                660                     665                     670

Thr Gln Tyr Ser Thr Gly Gln Val Ser Val Glu Ile Glu Trp Glu Leu
            675                     680                     685

Gln Lys Glu Asn Ser Lys Arg Trp Asn Pro Glu Ile Gln Tyr Thr Ser
            690                     695                     700

Asn Phe Glu Lys Gln Thr Gly Val Asp Phe Ala Val Asp Ser Gln Gly
705                     710                     715                 720

Val Tyr Ser Glu Pro Arg Pro Ile Gly Thr Arg Tyr Leu Thr Arg Asn
                725                     730                     735

Leu

<210> SEQ ID NO 25
<211> LENGTH: 738
<212> TYPE: PRT
<213> ORGANISM: artificial
<220> FEATURE:
<223> OTHER INFORMATION: AAV8 VP1 capsid protein sequence

<400> SEQUENCE: 25

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80
```

```
Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495
```

-continued

```
Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 26
<211> LENGTH: 736
<212> TYPE: PRT
<213> ORGANISM: artificial
<220> FEATURE:
<223> OTHER INFORMATION: AAV9 VP1 capsid protein sequence

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
```

-continued

```
            115                 120                 125
Leu Gly Leu Val Glu Ala Ala Lys Thr Ala Pro Gly Lys Lys Arg
            130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                    165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                    245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                    325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                    405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
                450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                    485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
```

```
Lys Gln Gly Thr Gly Arg Asp Asn Val Asp Ala Asp Lys Val Met Ile
545                 550                 555                 560

Thr Asn Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 27
<211> LENGTH: 738
<212> TYPE: PRT
<213> ORGANISM: artificial
<220> FEATURE:
<223> OTHER INFORMATION: AAV10 VP1 capsid protein sequence

<400> SEQUENCE: 27

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175
```

```
Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590
```

-continued

```
Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 28
<211> LENGTH: 733
<212> TYPE: PRT
<213> ORGANISM: artificial
<220> FEATURE:
<223> OTHER INFORMATION: AAV11 VP1 capsid protein sequence

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
```

```
              210                 215                 220
Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                    245                 250                 255

Thr Ser Ser Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
            275                 280                 285

Arg Leu Ile Asn Asn Asn Trp Gly Leu Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                    325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
        370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                    405                 410                 415

Tyr Ala His Ser Gln Ser Leu Asp Arg Leu Met Asn Pro Leu Leu Asp
                420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
        450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                    485                 490                 495

Gly Asn Ala Leu Leu Lys Tyr Asp Thr His Tyr Thr Leu Asn Asn Arg
                500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
        530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                    565                 570                 575

Ile Ala Asp Asn Asn Gln Asn Ala Thr Thr Ala Pro Ile Thr Gly Asn
                580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
        610                 615                 620

His Phe His Pro Ser Pro Leu Ile Gly Gly Phe Gly Leu Lys His Pro
625                 630                 635                 640
```

```
Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 29
<211> LENGTH: 742
<212> TYPE: PRT
<213> ORGANISM: artificial
<220> FEATURE:
<223> OTHER INFORMATION: AAV12 VP1 capsid protein sequence

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Gln Arg Leu Ala Thr Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
            180                 185                 190

Glu Gly Ser Ser Ser Gly Glu Met Ser His Asp Ala Glu Met Arg Ala
        195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
            260                 265                 270
```

```
Asn Gly Phe Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
            340                 345                 350

Val Met Asp Ala Gly Gln Glu Gly Ser Phe Pro Pro Phe Pro Asn Asp
        355                 360                 365

Val Phe Met Val Pro Gln Tyr Gly Tyr Cys Gly Val Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
            420                 425                 430

Asp Arg Met Met Asn Pro Leu Leu Asp Gln Tyr Leu Trp His Leu Gln
        435                 440                 445

Ser Thr Thr Thr Gly Asn Ser Leu Asn Gln Gly Thr Ala Thr Thr Thr
    450                 455                 460

Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Ile Ala Thr Thr Asn
                565                 570                 575

Pro Arg Asp Thr Asp Met Phe Gly Gln Ile Ala Asp Asn Gln Asn
        580                 585                 590

Ala Thr Thr Ala Pro His Ile Ala Asn Leu Asp Ala Met Gly Ile Val
            595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Gln Ile Phe Ile Lys
                645                 650                 655

Asn Thr Pro Val Pro Ala Asn Pro Asn Thr Thr Phe Ser Ala Ala Arg
            660                 665                 670

Ile Asn Ser Phe Leu Thr Gln Tyr Ser Thr Gly Gln Val Ala Val Gln
        675                 680                 685
```

```
Ile Asp Trp Glu Ile Gln Lys Glu His Ser Lys Arg Trp Asn Pro Glu
690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740

<210> SEQ ID NO 30
<211> LENGTH: 733
<212> TYPE: PRT
<213> ORGANISM: artificial
<220> FEATURE:
<223> OTHER INFORMATION: AAV13 VP1 capsid protein sequence

<400> SEQUENCE: 30

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Gly Ile Gly Lys Ser
145                 150                 155                 160

Ser Gly Gln Gln Pro Ala Arg Lys Arg Leu Asn Phe Gly Gln Thr Gly
                165                 170                 175

Asp Thr Glu Ser Val Pro Asp Pro Gln Pro Leu Gly Gln Pro Pro Ala
            180                 185                 190

Ala Pro Ser Gly Val Gly Ser Thr Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Thr Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300
```

```
Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
            325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
            355                 360                 365

Phe Met Val Pro Gln Tyr Gly Tyr Leu Thr Leu Asn Asn Gly Ser Gln
370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
            405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
            435                 440                 445

Thr Ala Ser Gly Thr Gln Gln Ser Arg Leu Leu Phe Ser Gln Ala Gly
450                 455                 460

Pro Thr Ser Met Ser Leu Gln Ala Lys Asn Trp Leu Pro Gly Pro Cys
465                 470                 475                 480

Tyr Arg Gln Gln Arg Leu Ser Lys Gln Ala Asn Asp Asn Asn Asn Ser
            485                 490                 495

Asn Phe Pro Trp Thr Gly Ala Thr Lys Tyr His Leu Asn Gly Arg Asp
            500                 505                 510

Ser Leu Val Asn Pro Gly Pro Ala Met Ala Ser His Lys Asp Asp Lys
            515                 520                 525

Glu Lys Phe Phe Pro Met His Gly Thr Leu Ile Phe Gly Lys Glu Gly
            530                 535                 540

Thr Asn Ala Asn Asn Ala Asp Leu Glu Asn Val Met Ile Thr Asp Glu
545                 550                 555                 560

Glu Glu Ile Arg Thr Thr Asn Pro Val Ala Thr Glu Gln Tyr Gly Thr
            565                 570                 575

Val Ser Asn Asn Leu Gln Asn Ser Asn Ala Gly Pro Thr Thr Gly Thr
            580                 585                 590

Val Asn His Gln Gly Ala Leu Pro Gly Met Val Trp Gln Asp Arg Asp
            595                 600                 605

Val Tyr Leu Gln Gly Pro Ile Trp Ala Lys Ile Pro His Thr Asp Gly
610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
            645                 650                 655

Thr Asn Phe Ser Ala Ala Lys Phe Ala Ser Phe Ile Thr Gln Tyr Ser
            660                 665                 670

Thr Gly Gln Val Ser Val Glu Ile Glu Trp Glu Leu Gln Lys Glu Asn
            675                 680                 685

Ser Lys Arg Trp Asn Pro Glu Ile Gln Tyr Thr Ser Asn Tyr Asn Lys
            690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
```

```
                725                 730

<210> SEQ ID NO 31
<211> LENGTH: 5
<212> TYPE: PRT
<213> ORGANISM: artificial
<220> FEATURE:
<223> OTHER INFORMATION: peptide

<400> SEQUENCE: 31

Phe Val Phe Leu Pro
1               5

<210> SEQ ID NO 32
<211> LENGTH: 4
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(3)
<223> OTHER INFORMATION: Xaa can be any naturally occuring amino acid

<400> SEQUENCE: 32

Asx Xaa Xaa Asx
1

<210> SEQ ID NO 33
<211> LENGTH: 4
<212> TYPE: PRT
<213> ORGANISM: artificial
<220> FEATURE:
<223> OTHER INFORMATION: peptide

<400> SEQUENCE: 33

Arg Gly Asn Arg
1

<210> SEQ ID NO 34
<211> LENGTH: 7
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (7)..(7)
<223> OTHER INFORMATION: Xaa is G or S

<400> SEQUENCE: 34

Asn Ser Val Arg Asp Leu Xaa
1               5

<210> SEQ ID NO 35
<211> LENGTH: 7
<212> TYPE: PRT
<213> ORGANISM: artificial
<220> FEATURE:
<223> OTHER INFORMATION: peptide

<400> SEQUENCE: 35

Pro Arg Ser Val Thr Val Pro
1               5

<210> SEQ ID NO 36
<211> LENGTH: 7
<212> TYPE: PRT
```

```
<213> ORGANISM: artificial
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: Xaa is any naturally occuring amino acid
<220> FEATURE:
<221> NAME/KEY: MISC_FEATURE
<222> LOCATION: (7)..(7)
<223> OTHER INFORMATION: Xaa is S or A

<400> SEQUENCE: 36

Asn Ser Val Ser Ser Xaa Xaa
1               5

<210> SEQ ID NO 37
<211> LENGTH: 6
<212> TYPE: PRT
<213> ORGANISM: artificial
<220> FEATURE:
<223> OTHER INFORMATION: peptide

<400> SEQUENCE: 37

Asn Gly Arg Ala His Ala
1               5

<210> SEQ ID NO 38
<211> LENGTH: 7
<212> TYPE: PRT
<213> ORGANISM: artificial
<220> FEATURE:
<223> OTHER INFORMATION: peptide

<400> SEQUENCE: 38

Gln Pro Glu His Ser Ser Thr
1               5

<210> SEQ ID NO 39
<211> LENGTH: 7
<212> TYPE: PRT
<213> ORGANISM: artificial
<220> FEATURE:
<223> OTHER INFORMATION: peptide

<400> SEQUENCE: 39

Val Asn Thr Ala Asn Ser Thr
1               5

<210> SEQ ID NO 40
<211> LENGTH: 7
<212> TYPE: PRT
<213> ORGANISM: artificial
<220> FEATURE:
<223> OTHER INFORMATION: peptide

<400> SEQUENCE: 40

His Gly Pro Met Gln Lys Ser
1               5

<210> SEQ ID NO 41
<211> LENGTH: 7
<212> TYPE: PRT
<213> ORGANISM: artificial
<220> FEATURE:
<223> OTHER INFORMATION: peptide

<400> SEQUENCE: 41
```

```
Pro His Lys Pro Pro Leu Ala
1               5

<210> SEQ ID NO 42
<211> LENGTH: 7
<212> TYPE: PRT
<213> ORGANISM: artificial
<220> FEATURE:
<223> OTHER INFORMATION: peptide

<400> SEQUENCE: 42

Ile Lys Asn Asn Glu Met Trp
1               5

<210> SEQ ID NO 43
<211> LENGTH: 7
<212> TYPE: PRT
<213> ORGANISM: artificial
<220> FEATURE:
<223> OTHER INFORMATION: peptide

<400> SEQUENCE: 43

Arg Asn Leu Asp Thr Pro Met
1               5

<210> SEQ ID NO 44
<211> LENGTH: 7
<212> TYPE: PRT
<213> ORGANISM: artificial
<220> FEATURE:
<223> OTHER INFORMATION: peptide

<400> SEQUENCE: 44

Val Asp Ser His Arg Gln Ser
1               5

<210> SEQ ID NO 45
<211> LENGTH: 7
<212> TYPE: PRT
<213> ORGANISM: artificial
<220> FEATURE:
<223> OTHER INFORMATION: peptide

<400> SEQUENCE: 45

Tyr Asp Ser Lys Thr Lys Thr
1               5

<210> SEQ ID NO 46
<211> LENGTH: 7
<212> TYPE: PRT
<213> ORGANISM: artificial
<220> FEATURE:
<223> OTHER INFORMATION: peptide

<400> SEQUENCE: 46

Ser Gln Leu Pro His Gln Lys
1               5

<210> SEQ ID NO 47
<211> LENGTH: 7
<212> TYPE: PRT
<213> ORGANISM: artificial
<220> FEATURE:
<223> OTHER INFORMATION: peptide

<400> SEQUENCE: 47

Ser Thr Met Gln Gln Asn Thr
```

```
1               5

<210> SEQ ID NO 48
<211> LENGTH: 7
<212> TYPE: PRT
<213> ORGANISM: artificial
<220> FEATURE:
<223> OTHER INFORMATION: peptide

<400> SEQUENCE: 48

Thr Glu Arg Tyr Met Thr Gln
1               5

<210> SEQ ID NO 49
<211> LENGTH: 7
<212> TYPE: PRT
<213> ORGANISM: artificial
<220> FEATURE:
<223> OTHER INFORMATION: peptide

<400> SEQUENCE: 49

Gln Pro Glu His Ser Ser Thr
1               5

<210> SEQ ID NO 50
<211> LENGTH: 7
<212> TYPE: PRT
<213> ORGANISM: artificial
<220> FEATURE:
<223> OTHER INFORMATION: peptide

<400> SEQUENCE: 50

Asp Ala Ser Leu Ser Thr Ser
1               5

<210> SEQ ID NO 51
<211> LENGTH: 7
<212> TYPE: PRT
<213> ORGANISM: artificial
<220> FEATURE:
<223> OTHER INFORMATION: peptide

<400> SEQUENCE: 51

Asp Leu Pro Asn Lys Lys Thr
1               5

<210> SEQ ID NO 52
<211> LENGTH: 7
<212> TYPE: PRT
<213> ORGANISM: artificial
<220> FEATURE:
<223> OTHER INFORMATION: peptide

<400> SEQUENCE: 52

Asp Leu Thr Ala Ala Arg Leu
1               5

<210> SEQ ID NO 53
<211> LENGTH: 7
<212> TYPE: PRT
<213> ORGANISM: artificial
<220> FEATURE:
<223> OTHER INFORMATION: peptide

<400> SEQUENCE: 53

Glu Pro His Gln Phe Asn Tyr
1               5
```

```
<210> SEQ ID NO 54
<211> LENGTH: 7
<212> TYPE: PRT
<213> ORGANISM: artificial
<220> FEATURE:
<223> OTHER INFORMATION: peptide

<400> SEQUENCE: 54

Glu Pro Gln Ser Asn His Thr
1               5

<210> SEQ ID NO 55
<211> LENGTH: 7
<212> TYPE: PRT
<213> ORGANISM: artificial
<220> FEATURE:
<223> OTHER INFORMATION: peptide

<400> SEQUENCE: 55

Met Ser Ser Trp Pro Ser Gln
1               5

<210> SEQ ID NO 56
<211> LENGTH: 7
<212> TYPE: PRT
<213> ORGANISM: artificial
<220> FEATURE:
<223> OTHER INFORMATION: peptide

<400> SEQUENCE: 56

Asn Pro Lys His Asn Ala Thr
1               5

<210> SEQ ID NO 57
<211> LENGTH: 7
<212> TYPE: PRT
<213> ORGANISM: artificial
<220> FEATURE:
<223> OTHER INFORMATION: peptide

<400> SEQUENCE: 57

Pro Asp Gly Met Arg Thr Thr
1               5

<210> SEQ ID NO 58
<211> LENGTH: 7
<212> TYPE: PRT
<213> ORGANISM: artificial
<220> FEATURE:
<223> OTHER INFORMATION: peptide

<400> SEQUENCE: 58

Pro Asn Asn Asn Lys Thr Thr
1               5

<210> SEQ ID NO 59
<211> LENGTH: 7
<212> TYPE: PRT
<213> ORGANISM: artificial
<220> FEATURE:
<223> OTHER INFORMATION: peptide

<400> SEQUENCE: 59

Gln Ser Thr Thr His Asp Ser
1               5
```

```
<210> SEQ ID NO 60
<211> LENGTH: 7
<212> TYPE: PRT
<213> ORGANISM: artificial
<220> FEATURE:
<223> OTHER INFORMATION: peptide

<400> SEQUENCE: 60

Thr Gly Ser Lys Gln Lys Gln
1               5

<210> SEQ ID NO 61
<211> LENGTH: 7
<212> TYPE: PRT
<213> ORGANISM: artificial
<220> FEATURE:
<223> OTHER INFORMATION: peptide

<400> SEQUENCE: 61

Ser Leu Lys His Gln Ala Leu
1               5

<210> SEQ ID NO 62
<211> LENGTH: 7
<212> TYPE: PRT
<213> ORGANISM: artificial
<220> FEATURE:
<223> OTHER INFORMATION: peptide

<400> SEQUENCE: 62

Ser Pro Ile Asp Gly Glu Gln
1               5

<210> SEQ ID NO 63
<211> LENGTH: 8
<212> TYPE: PRT
<213> ORGANISM: artificial
<220> FEATURE:
<223> OTHER INFORMATION: peptide

<400> SEQUENCE: 63

Trp Ile Phe Pro Trp Ile Gln Leu
1               5

<210> SEQ ID NO 64
<211> LENGTH: 9
<212> TYPE: PRT
<213> ORGANISM: artificial
<220> FEATURE:
<223> OTHER INFORMATION: peptide

<400> SEQUENCE: 64

Cys Asp Cys Arg Gly Asp Cys Phe Cys
1               5

<210> SEQ ID NO 65
<211> LENGTH: 5
<212> TYPE: PRT
<213> ORGANISM: artificial
<220> FEATURE:
<223> OTHER INFORMATION: peptide

<400> SEQUENCE: 65

Cys Asn Gly Arg Cys
1               5
```

```
<210> SEQ ID NO 66
<211> LENGTH: 7
<212> TYPE: PRT
<213> ORGANISM: artificial
<220> FEATURE:
<223> OTHER INFORMATION: peptide

<400> SEQUENCE: 66

Cys Pro Arg Glu Cys Glu Ser
1               5

<210> SEQ ID NO 67
<211> LENGTH: 10
<212> TYPE: PRT
<213> ORGANISM: artificial
<220> FEATURE:
<223> OTHER INFORMATION: peptide

<400> SEQUENCE: 67

Cys Thr Thr His Trp Gly Phe Thr Leu Cys
1               5                   10

<210> SEQ ID NO 68
<211> LENGTH: 9
<212> TYPE: PRT
<213> ORGANISM: artificial
<220> FEATURE:
<223> OTHER INFORMATION: peptide

<400> SEQUENCE: 68

Cys Gly Arg Arg Ala Gly Gly Ser Cys
1               5

<210> SEQ ID NO 69
<211> LENGTH: 9
<212> TYPE: PRT
<213> ORGANISM: artificial
<220> FEATURE:
<223> OTHER INFORMATION: peptide

<400> SEQUENCE: 69

Cys Lys Gly Gly Arg Ala Lys Asp Cys
1               5

<210> SEQ ID NO 70
<211> LENGTH: 9
<212> TYPE: PRT
<213> ORGANISM: artificial
<220> FEATURE:
<223> OTHER INFORMATION: peptide

<400> SEQUENCE: 70

Cys Val Pro Glu Leu Gly His Glu Cys
1               5

<210> SEQ ID NO 71
<211> LENGTH: 9
<212> TYPE: PRT
<213> ORGANISM: artificial
<220> FEATURE:
<223> OTHER INFORMATION: peptide

<400> SEQUENCE: 71

Cys Arg Arg Glu Thr Ala Trp Ala Lys
1               5

<210> SEQ ID NO 72
```

```
<211> LENGTH: 14
<212> TYPE: PRT
<213> ORGANISM: artificial
<220> FEATURE:
<223> OTHER INFORMATION: peptide

<400> SEQUENCE: 72

Val Ser Trp Phe Ser His Arg Tyr Ser Pro Phe Ala Val Ser
1               5                   10

<210> SEQ ID NO 73
<211> LENGTH: 13
<212> TYPE: PRT
<213> ORGANISM: artificial
<220> FEATURE:
<223> OTHER INFORMATION: peptide

<400> SEQUENCE: 73

Gly Tyr Arg Asp Gly Tyr Ala Gly Pro Ile Leu Tyr Asn
1               5                   10

<210> SEQ ID NO 74
<211> LENGTH: 7
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (5)..(7)
<223> OTHER INFORMATION: Xaa can be any naturally occurring amino acid

<400> SEQUENCE: 74

Xaa Xaa Xaa Tyr Xaa Xaa Xaa
1               5

<210> SEQ ID NO 75
<211> LENGTH: 4
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa can be any naturally occurring amino acid

<400> SEQUENCE: 75

Tyr Xaa Asn Trp
1

<210> SEQ ID NO 76
<211> LENGTH: 7
<212> TYPE: PRT
<213> ORGANISM: artificial
<220> FEATURE:
<223> OTHER INFORMATION: peptide

<400> SEQUENCE: 76

Arg Pro Leu Pro Pro Leu Pro
1               5

<210> SEQ ID NO 77
<211> LENGTH: 7
<212> TYPE: PRT
```

```
-continued

<213> ORGANISM: artificial
<220> FEATURE:
<223> OTHER INFORMATION: peptide

<400> SEQUENCE: 77

Ala Pro Pro Leu Pro Pro Arg
1               5

<210> SEQ ID NO 78
<211> LENGTH: 12
<212> TYPE: PRT
<213> ORGANISM: artificial
<220> FEATURE:
<223> OTHER INFORMATION: peptide

<400> SEQUENCE: 78

Asp Val Phe Tyr Pro Tyr Pro Tyr Ala Ser Gly Ser
1               5                   10

<210> SEQ ID NO 79
<211> LENGTH: 6
<212> TYPE: PRT
<213> ORGANISM: artificial
<220> FEATURE:
<223> OTHER INFORMATION: peptide

<400> SEQUENCE: 79

Met Tyr Trp Tyr Pro Tyr
1               5

<210> SEQ ID NO 80
<211> LENGTH: 12
<212> TYPE: PRT
<213> ORGANISM: artificial
<220> FEATURE:
<223> OTHER INFORMATION: peptide

<400> SEQUENCE: 80

Asp Ile Thr Trp Asp Gln Leu Trp Asp Leu Met Lys
1               5                   10

<210> SEQ ID NO 81
<211> LENGTH: 8
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa is G or L

<400> SEQUENCE: 81

Cys Trp Asp Asp Xaa Trp Leu Cys
1               5

<210> SEQ ID NO 82
<211> LENGTH: 14
<212> TYPE: PRT
<213> ORGANISM: artificial
<220> FEATURE:
<223> OTHER INFORMATION: peptide

<400> SEQUENCE: 82

Glu Trp Cys Glu Tyr Leu Gly Gly Tyr Leu Arg Cys Tyr Ala
1               5                   10
```

```
<210> SEQ ID NO 83
<211> LENGTH: 14
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be any naturally occurring amino acid

<400> SEQUENCE: 83

Tyr Xaa Cys Xaa Xaa Gly Pro Xaa Thr Trp Xaa Cys Xaa Pro
1               5                   10

<210> SEQ ID NO 84
<211> LENGTH: 14
<212> TYPE: PRT
<213> ORGANISM: artificial
<220> FEATURE:
<223> OTHER INFORMATION: peptide

<400> SEQUENCE: 84

Ile Glu Gly Pro Thr Leu Arg Gln Trp Leu Ala Ala Arg Ala
1               5                   10

<210> SEQ ID NO 85
<211> LENGTH: 5
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Y, W, F or H

<400> SEQUENCE: 85

Leu Trp Xaa Xaa Xaa
1               5

<210> SEQ ID NO 86
<211> LENGTH: 7
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
```

```
<222> LOCATION: (3)..(4)
<223> OTHER INFORMATION: Xaa can be any naturally occurring amino acid

<400> SEQUENCE: 86

Xaa Phe Xaa Xaa Tyr Leu Trp
1               5

<210> SEQ ID NO 87
<211> LENGTH: 13
<212> TYPE: PRT
<213> ORGANISM: artificial
<220> FEATURE:
<223> OTHER INFORMATION: peptide

<400> SEQUENCE: 87

Ser Ser Ile Ile Ser His Phe Arg Trp Gly Leu Cys Asp
1               5                   10

<210> SEQ ID NO 88
<211> LENGTH: 13
<212> TYPE: PRT
<213> ORGANISM: artificial
<220> FEATURE:
<223> OTHER INFORMATION: peptide

<400> SEQUENCE: 88

Met Ser Arg Pro Ala Cys Pro Pro Asn Asp Lys Tyr Glu
1               5                   10

<210> SEQ ID NO 89
<211> LENGTH: 8
<212> TYPE: PRT
<213> ORGANISM: artificial
<220> FEATURE:
<223> OTHER INFORMATION: peptide

<400> SEQUENCE: 89

Cys Leu Arg Ser Gly Arg Gly Cys
1               5

<210> SEQ ID NO 90
<211> LENGTH: 9
<212> TYPE: PRT
<213> ORGANISM: artificial
<220> FEATURE:
<223> OTHER INFORMATION: peptide

<400> SEQUENCE: 90

Cys His Trp Met Phe Ser Pro Trp Cys
1               5

<210> SEQ ID NO 91
<211> LENGTH: 4
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 91

Trp Xaa Xaa Phe
1

<210> SEQ ID NO 92
```

```
<211> LENGTH: 8
<212> TYPE: PRT
<213> ORGANISM: artificial
<220> FEATURE:
<223> OTHER INFORMATION: peptide

<400> SEQUENCE: 92

Cys Ser Ser Arg Leu Asp Ala Cys
1               5

<210> SEQ ID NO 93
<211> LENGTH: 7
<212> TYPE: PRT
<213> ORGANISM: artificial
<220> FEATURE:
<223> OTHER INFORMATION: peptide

<400> SEQUENCE: 93

Cys Leu Pro Val Ala Ser Cys
1               5

<210> SEQ ID NO 94
<211> LENGTH: 13
<212> TYPE: PRT
<213> ORGANISM: artificial
<220> FEATURE:
<223> OTHER INFORMATION: peptide

<400> SEQUENCE: 94

Cys Gly Phe Glu Cys Val Arg Gln Cys Pro Glu Arg Cys
1               5                   10

<210> SEQ ID NO 95
<211> LENGTH: 13
<212> TYPE: PRT
<213> ORGANISM: artificial
<220> FEATURE:
<223> OTHER INFORMATION: peptide

<400> SEQUENCE: 95

Cys Val Ala Leu Cys Arg Glu Ala Cys Gly Glu Gly Cys
1               5                   10

<210> SEQ ID NO 96
<211> LENGTH: 9
<212> TYPE: PRT
<213> ORGANISM: artificial
<220> FEATURE:
<223> OTHER INFORMATION: peptide

<400> SEQUENCE: 96

Ser Trp Cys Glu Pro Gly Trp Cys Arg
1               5

<210> SEQ ID NO 97
<211> LENGTH: 7
<212> TYPE: PRT
<213> ORGANISM: artificial
<220> FEATURE:
<223> OTHER INFORMATION: peptide

<400> SEQUENCE: 97

Tyr Ser Gly Lys Trp Gly Trp
1               5

<210> SEQ ID NO 98
<211> LENGTH: 7
```

```
<212> TYPE: PRT
<213> ORGANISM: artificial
<220> FEATURE:
<223> OTHER INFORMATION: peptide

<400> SEQUENCE: 98

Gly Leu Ser Gly Gly Arg Ser
1               5

<210> SEQ ID NO 99
<211> LENGTH: 7
<212> TYPE: PRT
<213> ORGANISM: artificial
<220> FEATURE:
<223> OTHER INFORMATION: peptide

<400> SEQUENCE: 99

Leu Met Leu Pro Arg Ala Asp
1               5

<210> SEQ ID NO 100
<211> LENGTH: 9
<212> TYPE: PRT
<213> ORGANISM: artificial
<220> FEATURE:
<223> OTHER INFORMATION: peptide

<400> SEQUENCE: 100

Cys Ser Cys Phe Arg Asp Val Cys Cys
1               5

<210> SEQ ID NO 101
<211> LENGTH: 9
<212> TYPE: PRT
<213> ORGANISM: artificial
<220> FEATURE:
<223> OTHER INFORMATION: peptide

<400> SEQUENCE: 101

Cys Arg Asp Val Val Ser Val Ile Cys
1               5

<210> SEQ ID NO 102
<211> LENGTH: 5
<212> TYPE: PRT
<213> ORGANISM: artificial
<220> FEATURE:
<223> OTHER INFORMATION: peptide

<400> SEQUENCE: 102

Cys Asn Gly Arg Cys
1               5

<210> SEQ ID NO 103
<211> LENGTH: 6
<212> TYPE: PRT
<213> ORGANISM: artificial
<220> FEATURE:
<223> OTHER INFORMATION: peptide

<400> SEQUENCE: 103

Met Ala Arg Ser Gly Leu
1               5

<210> SEQ ID NO 104
<211> LENGTH: 6
<212> TYPE: PRT
```

<213> ORGANISM: artificial
<220> FEATURE:
<223> OTHER INFORMATION: peptide

<400> SEQUENCE: 104

Met Ala Arg Ala Lys Glu
1               5

<210> SEQ ID NO 105
<211> LENGTH: 6
<212> TYPE: PRT
<213> ORGANISM: artificial
<220> FEATURE:
<223> OTHER INFORMATION: peptide

<400> SEQUENCE: 105

Met Ser Arg Thr Met Ser
1               5

<210> SEQ ID NO 106
<211> LENGTH: 6
<212> TYPE: PRT
<213> ORGANISM: artificial
<220> FEATURE:
<223> OTHER INFORMATION: peptide

<400> SEQUENCE: 106

Lys Cys Cys Tyr Ser Leu
1               5

<210> SEQ ID NO 107
<211> LENGTH: 14
<212> TYPE: PRT
<213> ORGANISM: artificial
<220> FEATURE:
<223> OTHER INFORMATION: peptide

<400> SEQUENCE: 107

Met Tyr Trp Gly Asp Ser His Trp Leu Gln Tyr Trp Tyr Glu
1               5                   10

<210> SEQ ID NO 108
<211> LENGTH: 7
<212> TYPE: PRT
<213> ORGANISM: artificial
<220> FEATURE:
<223> OTHER INFORMATION: peptide

<400> SEQUENCE: 108

Met Gln Leu Pro Leu Ala Thr
1               5

<210> SEQ ID NO 109
<211> LENGTH: 4
<212> TYPE: PRT
<213> ORGANISM: artificial
<220> FEATURE:
<223> OTHER INFORMATION: peptide

<400> SEQUENCE: 109

Glu Trp Leu Ser
1

<210> SEQ ID NO 110
<211> LENGTH: 4
<212> TYPE: PRT
<213> ORGANISM: artificial

```
<220> FEATURE:
<223> OTHER INFORMATION: peptide

<400> SEQUENCE: 110

Ser Asn Glu Trp
1

<210> SEQ ID NO 111
<211> LENGTH: 4
<212> TYPE: PRT
<213> ORGANISM: artificial
<220> FEATURE:
<223> OTHER INFORMATION: peptide

<400> SEQUENCE: 111

Thr Asn Tyr Leu
1

<210> SEQ ID NO 112
<211> LENGTH: 8
<212> TYPE: PRT
<213> ORGANISM: artificial
<220> FEATURE:
<223> OTHER INFORMATION: peptide

<400> SEQUENCE: 112

Trp Ile Phe Pro Trp Ile Gln Leu
1               5

<210> SEQ ID NO 113
<211> LENGTH: 12
<212> TYPE: PRT
<213> ORGANISM: artificial
<220> FEATURE:
<223> OTHER INFORMATION: peptide

<400> SEQUENCE: 113

Trp Asp Leu Ala Trp Met Phe Arg Leu Pro Val Gly
1               5                   10

<210> SEQ ID NO 114
<211> LENGTH: 13
<212> TYPE: PRT
<213> ORGANISM: artificial
<220> FEATURE:
<223> OTHER INFORMATION: peptide

<400> SEQUENCE: 114

Cys Thr Val Ala Leu Pro Gly Gly Tyr Val Arg Val Cys
1               5                   10

<210> SEQ ID NO 115
<211> LENGTH: 9
<212> TYPE: PRT
<213> ORGANISM: artificial
<220> FEATURE:
<223> OTHER INFORMATION: peptide

<400> SEQUENCE: 115

Cys Val Pro Glu Leu Gly His Glu Cys
1               5

<210> SEQ ID NO 116
<211> LENGTH: 9
<212> TYPE: PRT
<213> ORGANISM: artificial
<220> FEATURE:
```

<223> OTHER INFORMATION: peptide

<400> SEQUENCE: 116

Cys Gly Arg Arg Ala Gly Gly Ser Cys
1               5

<210> SEQ ID NO 117
<211> LENGTH: 13
<212> TYPE: PRT
<213> ORGANISM: artificial
<220> FEATURE:
<223> OTHER INFORMATION: peptide

<400> SEQUENCE: 117

Cys Val Ala Tyr Cys Ile Glu His His Cys Trp Thr Cys
1               5                   10

<210> SEQ ID NO 118
<211> LENGTH: 12
<212> TYPE: PRT
<213> ORGANISM: artificial
<220> FEATURE:
<223> OTHER INFORMATION: peptide

<400> SEQUENCE: 118

Cys Val Phe Ala His Asn Tyr Asp Tyr Leu Val Cys
1               5                   10

<210> SEQ ID NO 119
<211> LENGTH: 10
<212> TYPE: PRT
<213> ORGANISM: artificial
<220> FEATURE:
<223> OTHER INFORMATION: peptide

<400> SEQUENCE: 119

Cys Val Phe Thr Ser Asn Tyr Ala Phe Cys
1               5                   10

<210> SEQ ID NO 120
<211> LENGTH: 7
<212> TYPE: PRT
<213> ORGANISM: artificial
<220> FEATURE:
<223> OTHER INFORMATION: peptide

<400> SEQUENCE: 120

Val His Ser Pro Asn Lys Lys
1               5

<210> SEQ ID NO 121
<211> LENGTH: 9
<212> TYPE: PRT
<213> ORGANISM: artificial
<220> FEATURE:
<223> OTHER INFORMATION: peptide

<400> SEQUENCE: 121

Cys Asp Cys Arg Gly Asp Cys Phe Cys
1               5

<210> SEQ ID NO 122
<211> LENGTH: 7
<212> TYPE: PRT
<213> ORGANISM: artificial
<220> FEATURE:
<223> OTHER INFORMATION: peptide

```
<400> SEQUENCE: 122

Cys Arg Gly Asp Gly Trp Cys
1               5

<210> SEQ ID NO 123
<211> LENGTH: 6
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 123

Xaa Arg Gly Cys Asp Xaa
1               5

<210> SEQ ID NO 124
<211> LENGTH: 4
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is S or T

<400> SEQUENCE: 124

Pro Xaa Xaa Xaa
1

<210> SEQ ID NO 125
<211> LENGTH: 10
<212> TYPE: PRT
<213> ORGANISM: artificial
<220> FEATURE:
<223> OTHER INFORMATION: peptide

<400> SEQUENCE: 125

Cys Thr Thr His Trp Gly Phe Thr Leu Cys
1               5                   10

<210> SEQ ID NO 126
<211> LENGTH: 11
<212> TYPE: PRT
<213> ORGANISM: artificial
<220> FEATURE:
<223> OTHER INFORMATION: peptide

<400> SEQUENCE: 126

Ser Gly Lys Gly Pro Arg Gln Ile Thr Ala Leu
1               5                   10

<210> SEQ ID NO 127
<211> LENGTH: 6
<212> TYPE: PRT
<213> ORGANISM: artificial
```

```
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is A or Q
<220> FEATURE:
<221> NAME/KEY: MISC_FEATURE
<222> LOCATION: (3)..(3)
<223> OTHER INFORMATION: Xaa is N or A
<220> FEATURE:
<221> NAME/KEY: MISC_FEATURE
<222> LOCATION: (4)..(4)
<223> OTHER INFORMATION: Xaa is L or Y
<220> FEATURE:
<221> NAME/KEY: MISC_FEATURE
<222> LOCATION: (5)..(5)
<223> OTHER INFORMATION: Xaa is T, V, M or R
<220> FEATURE:
<221> NAME/KEY: MISC_FEATURE
<222> LOCATION: (6)..(6)
<223> OTHER INFORMATION: Xaa is R or K

<400> SEQUENCE: 127

Ala Xaa Xaa Xaa Xaa Xaa
1               5

<210> SEQ ID NO 128
<211> LENGTH: 6
<212> TYPE: PRT
<213> ORGANISM: artificial
<220> FEATURE:
<223> OTHER INFORMATION: peptide

<400> SEQUENCE: 128

Val Tyr Met Ser Pro Phe
1               5

<210> SEQ ID NO 129
<211> LENGTH: 7
<212> TYPE: PRT
<213> ORGANISM: artificial
<220> FEATURE:
<223> OTHER INFORMATION: peptide

<400> SEQUENCE: 129

Met Gln Leu Pro Leu Ala Thr
1               5

<210> SEQ ID NO 130
<211> LENGTH: 7
<212> TYPE: PRT
<213> ORGANISM: artificial
<220> FEATURE:
<223> OTHER INFORMATION: peptide

<400> SEQUENCE: 130

Ala Thr Trp Leu Pro Pro Arg
1               5

<210> SEQ ID NO 131
<211> LENGTH: 12
<212> TYPE: PRT
<213> ORGANISM: artificial
<220> FEATURE:
<223> OTHER INFORMATION: peptide

<400> SEQUENCE: 131

His Thr Met Tyr Tyr His His Tyr Gln His His Leu
1               5                   10
```

<210> SEQ ID NO 132
<211> LENGTH: 19
<212> TYPE: PRT
<213> ORGANISM: artificial
<220> FEATURE:
<223> OTHER INFORMATION: peptide

<400> SEQUENCE: 132

Ser Glu Val Gly Cys Arg Ala Gly Pro Leu Gln Trp Leu Cys Glu Lys
1               5                   10                  15

Tyr Phe Gly

<210> SEQ ID NO 133
<211> LENGTH: 18
<212> TYPE: PRT
<213> ORGANISM: artificial
<220> FEATURE:
<223> OTHER INFORMATION: peptide

<400> SEQUENCE: 133

Cys Gly Leu Leu Pro Val Gly Arg Pro Asp Arg Asn Val Trp Arg Trp
1               5                   10                  15

Leu Cys

<210> SEQ ID NO 134
<211> LENGTH: 15
<212> TYPE: PRT
<213> ORGANISM: artificial
<220> FEATURE:
<223> OTHER INFORMATION: peptide

<400> SEQUENCE: 134

Cys Lys Gly Gln Cys Asp Arg Phe Lys Gly Leu Pro Trp Glu Cys
1               5                   10                  15

<210> SEQ ID NO 135
<211> LENGTH: 5
<212> TYPE: PRT
<213> ORGANISM: artificial
<220> FEATURE:
<223> OTHER INFORMATION: peptide

<400> SEQUENCE: 135

Ser Gly Arg Ser Ala
1               5

<210> SEQ ID NO 136
<211> LENGTH: 4
<212> TYPE: PRT
<213> ORGANISM: artificial
<220> FEATURE:
<223> OTHER INFORMATION: peptide

<400> SEQUENCE: 136

Trp Gly Phe Pro
1

<210> SEQ ID NO 137
<211> LENGTH: 7
<212> TYPE: PRT
<213> ORGANISM: artificial
<220> FEATURE:
<223> OTHER INFORMATION: peptide
<220> FEATURE:
<221> NAME/KEY: MISC_FEATURE

```
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid

<400> SEQUENCE: 137

Xaa Phe Xaa Xaa Tyr Leu Trp
1               5

<210> SEQ ID NO 138
<211> LENGTH: 17
<212> TYPE: PRT
<213> ORGANISM: artificial
<220> FEATURE:
<223> OTHER INFORMATION: peptide

<400> SEQUENCE: 138

Ala Glu Pro Met Pro His Ser Leu Asn Phe Ser Gln Tyr Leu Trp Tyr
1               5                   10                  15
Thr

<210> SEQ ID NO 139
<211> LENGTH: 6
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Xaa is W or F

<400> SEQUENCE: 139

Trp Ala Tyr Xaa Ser Pro
1               5

<210> SEQ ID NO 140
<211> LENGTH: 7
<212> TYPE: PRT
<213> ORGANISM: artificial
<220> FEATURE:
<223> OTHER INFORMATION: peptide

<400> SEQUENCE: 140

Ile Glu Leu Leu Gln Ala Arg
1               5

<210> SEQ ID NO 141
<211> LENGTH: 12
<212> TYPE: PRT
<213> ORGANISM: artificial
<220> FEATURE:
<223> OTHER INFORMATION: peptide

<400> SEQUENCE: 141

Asp Ile Thr Trp Asp Gln Leu Trp Asp Leu Met Lys
1               5                   10

<210> SEQ ID NO 142
<211> LENGTH: 16
<212> TYPE: PRT
<213> ORGANISM: artificial
<220> FEATURE:
<223> OTHER INFORMATION: peptide

<400> SEQUENCE: 142
```

Ala Tyr Thr Lys Cys Ser Arg Gln Trp Arg Thr Cys Met Thr Thr His
1               5                   10                  15

<210> SEQ ID NO 143
<211> LENGTH: 15
<212> TYPE: PRT
<213> ORGANISM: artificial
<220> FEATURE:
<223> OTHER INFORMATION: peptide

<400> SEQUENCE: 143

Pro Gln Asn Ser Lys Ile Pro Gly Pro Thr Phe Leu Asp Pro His
1               5                   10                  15

<210> SEQ ID NO 144
<211> LENGTH: 15
<212> TYPE: PRT
<213> ORGANISM: artificial
<220> FEATURE:
<223> OTHER INFORMATION: peptide

<400> SEQUENCE: 144

Ser Met Glu Pro Ala Leu Pro Asp Trp Trp Trp Lys Met Phe Lys
1               5                   10                  15

<210> SEQ ID NO 145
<211> LENGTH: 16
<212> TYPE: PRT
<213> ORGANISM: artificial
<220> FEATURE:
<223> OTHER INFORMATION: peptide

<400> SEQUENCE: 145

Ala Asn Thr Pro Cys Gly Pro Tyr Thr His Asp Cys Pro Val Lys Arg
1               5                   10                  15

<210> SEQ ID NO 146
<211> LENGTH: 12
<212> TYPE: PRT
<213> ORGANISM: artificial
<220> FEATURE:
<223> OTHER INFORMATION: peptide

<400> SEQUENCE: 146

Thr Ala Cys His Gln His Val Arg Met Val Arg Pro
1               5                   10

<210> SEQ ID NO 147
<211> LENGTH: 12
<212> TYPE: PRT
<213> ORGANISM: artificial
<220> FEATURE:
<223> OTHER INFORMATION: peptide

<400> SEQUENCE: 147

Val Pro Trp Met Glu Pro Ala Tyr Gln Arg Phe Leu
1               5                   10

<210> SEQ ID NO 148
<211> LENGTH: 8
<212> TYPE: PRT
<213> ORGANISM: artificial
<220> FEATURE:
<223> OTHER INFORMATION: peptide

<400> SEQUENCE: 148

```
Asp Pro Arg Ala Thr Pro Gly Ser
1               5

<210> SEQ ID NO 149
<211> LENGTH: 12
<212> TYPE: PRT
<213> ORGANISM: artificial
<220> FEATURE:
<223> OTHER INFORMATION: peptide

<400> SEQUENCE: 149

Phe Arg Pro Asn Arg Ala Gln Asp Tyr Asn Thr Asn
1               5                   10

<210> SEQ ID NO 150
<211> LENGTH: 9
<212> TYPE: PRT
<213> ORGANISM: artificial
<220> FEATURE:
<223> OTHER INFORMATION: peptide

<400> SEQUENCE: 150

Cys Thr Lys Asn Ser Tyr Leu Met Cys
1               5

<210> SEQ ID NO 151
<211> LENGTH: 11
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is R or Q
<220> FEATURE:
<221> NAME/KEY: MISC_FEATURE
<222> LOCATION: (3)..(3)
<223> OTHER INFORMATION: Xaa is L or R
<220> FEATURE:
<221> NAME/KEY: MISC_FEATURE
<222> LOCATION: (5)..(5)
<223> OTHER INFORMATION: Xaa is G or N
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is A or V

<400> SEQUENCE: 151

Cys Xaa Xaa Thr Xaa Xaa Xaa Gly Xaa Gly Cys
1               5                   10

<210> SEQ ID NO 152
<211> LENGTH: 9
<212> TYPE: PRT
<213> ORGANISM: artificial
<220> FEATURE:
<223> OTHER INFORMATION: peptide

<400> SEQUENCE: 152

Cys Pro Ile Glu Asp Arg Pro Met Cys
1               5

<210> SEQ ID NO 153
<211> LENGTH: 12
<212> TYPE: PRT
```

```
<213> ORGANISM: artificial
<220> FEATURE:
<223> OTHER INFORMATION: peptide

<400> SEQUENCE: 153

His Glu Trp Ser Tyr Leu Ala Pro Tyr Pro Trp Phe
1               5                  10

<210> SEQ ID NO 154
<211> LENGTH: 9
<212> TYPE: PRT
<213> ORGANISM: artificial
<220> FEATURE:
<223> OTHER INFORMATION: peptide

<400> SEQUENCE: 154

Met Cys Pro Lys His Pro Leu Gly Cys
1               5

<210> SEQ ID NO 155
<211> LENGTH: 15
<212> TYPE: PRT
<213> ORGANISM: artificial
<220> FEATURE:
<223> OTHER INFORMATION: peptide

<400> SEQUENCE: 155

Arg Met Trp Pro Ser Ser Thr Val Asn Leu Ser Ala Gly Arg Arg
1               5                  10                  15

<210> SEQ ID NO 156
<211> LENGTH: 20
<212> TYPE: PRT
<213> ORGANISM: artificial
<220> FEATURE:
<223> OTHER INFORMATION: peptide

<400> SEQUENCE: 156

Ser Ala Lys Thr Ala Val Ser Gln Arg Val Trp Leu Pro Ser His Arg
1               5                  10                  15

Gly Gly Glu Pro
            20

<210> SEQ ID NO 157
<211> LENGTH: 20
<212> TYPE: PRT
<213> ORGANISM: artificial
<220> FEATURE:
<223> OTHER INFORMATION: peptide

<400> SEQUENCE: 157

Lys Ser Arg Glu His Val Asn Asn Ser Ala Cys Pro Ser Lys Arg Ile
1               5                  10                  15

Thr Ala Ala Leu
            20

<210> SEQ ID NO 158
<211> LENGTH: 4
<212> TYPE: PRT
<213> ORGANISM: artificial
<220> FEATURE:
<223> OTHER INFORMATION: peptide

<400> SEQUENCE: 158

Glu Gly Phe Arg
1
```

```
<210> SEQ ID NO 159
<211> LENGTH: 6
<212> TYPE: PRT
<213> ORGANISM: artificial
<220> FEATURE:
<223> OTHER INFORMATION: peptide

<400> SEQUENCE: 159

Ala Gly Leu Gly Val Arg
1               5

<210> SEQ ID NO 160
<211> LENGTH: 15
<212> TYPE: PRT
<213> ORGANISM: artificial
<220> FEATURE:
<223> OTHER INFORMATION: peptide

<400> SEQUENCE: 160

Gly Thr Arg Gln Gly His Thr Met Arg Leu Gly Val Ser Asp Gly
1               5                   10                  15

<210> SEQ ID NO 161
<211> LENGTH: 15
<212> TYPE: PRT
<213> ORGANISM: artificial
<220> FEATURE:
<223> OTHER INFORMATION: peptide

<400> SEQUENCE: 161

Ile Ala Gly Leu Ala Thr Pro Gly Trp Ser His Trp Leu Ala Leu
1               5                   10                  15

<210> SEQ ID NO 162
<211> LENGTH: 7
<212> TYPE: PRT
<213> ORGANISM: artificial
<220> FEATURE:
<223> OTHER INFORMATION: peptide

<400> SEQUENCE: 162

Ser Met Ser Ile Ala Arg Leu
1               5

<210> SEQ ID NO 163
<211> LENGTH: 7
<212> TYPE: PRT
<213> ORGANISM: artificial
<220> FEATURE:
<223> OTHER INFORMATION: peptide

<400> SEQUENCE: 163

His Thr Phe Glu Pro Gly Val
1               5

<210> SEQ ID NO 164
<211> LENGTH: 15
<212> TYPE: PRT
<213> ORGANISM: artificial
<220> FEATURE:
<223> OTHER INFORMATION: peptide

<400> SEQUENCE: 164

Asn Thr Ser Leu Lys Arg Ile Ser Asn Lys Arg Ile Arg Arg Lys
1               5                   10                  15
```

<210> SEQ ID NO 165
<211> LENGTH: 15
<212> TYPE: PRT
<213> ORGANISM: artificial
<220> FEATURE:
<223> OTHER INFORMATION: peptide

<400> SEQUENCE: 165

Leu Arg Ile Lys Arg Lys Arg Arg Lys Arg Lys Lys Thr Arg Lys
1               5                   10                  15

<210> SEQ ID NO 166
<211> LENGTH: 10
<212> TYPE: PRT
<213> ORGANISM: artificial
<220> FEATURE:
<223> OTHER INFORMATION: peptide

<400> SEQUENCE: 166

Val Gly Thr Phe Asn Glu Ala Lys Leu His
1               5                   10

<210> SEQ ID NO 167
<211> LENGTH: 10
<212> TYPE: PRT
<213> ORGANISM: artificial
<220> FEATURE:
<223> OTHER INFORMATION: peptide

<400> SEQUENCE: 167

Val Ser Thr Phe Asn Pro Ala Lys Leu Met
1               5                   10

<210> SEQ ID NO 168
<211> LENGTH: 10
<212> TYPE: PRT
<213> ORGANISM: artificial
<220> FEATURE:
<223> OTHER INFORMATION: peptide

<400> SEQUENCE: 168

Pro Leu Thr Phe Asn Cys Cys Lys Leu Asn
1               5                   10

<210> SEQ ID NO 169
<211> LENGTH: 10
<212> TYPE: PRT
<213> ORGANISM: artificial
<220> FEATURE:
<223> OTHER INFORMATION: peptide

<400> SEQUENCE: 169

Pro Val Thr Phe Asn Gln Asp Lys Leu Trp
1               5                   10

<210> SEQ ID NO 170
<211> LENGTH: 10
<212> TYPE: PRT
<213> ORGANISM: artificial
<220> FEATURE:
<223> OTHER INFORMATION: peptide

<400> SEQUENCE: 170

Pro Val Thr Phe Asn Ser Gly Lys Leu Cys
1               5                   10

```
<210> SEQ ID NO 171
<211> LENGTH: 10
<212> TYPE: PRT
<213> ORGANISM: artificial
<220> FEATURE:
<223> OTHER INFORMATION: peptide

<400> SEQUENCE: 171

Ile Gly Thr Phe Asn Gly Gln Lys Leu Cys
1               5                   10

<210> SEQ ID NO 172
<211> LENGTH: 10
<212> TYPE: PRT
<213> ORGANISM: artificial
<220> FEATURE:
<223> OTHER INFORMATION: peptide

<400> SEQUENCE: 172

Gln Val Thr Phe Asn Gly Gly Lys Leu Phe
1               5                   10

<210> SEQ ID NO 173
<211> LENGTH: 10
<212> TYPE: PRT
<213> ORGANISM: artificial
<220> FEATURE:
<223> OTHER INFORMATION: peptide

<400> SEQUENCE: 173

Pro Gly Thr Phe Asn Gly Gly Lys Leu Trp
1               5                   10

<210> SEQ ID NO 174
<211> LENGTH: 10
<212> TYPE: PRT
<213> ORGANISM: artificial
<220> FEATURE:
<223> OTHER INFORMATION: peptide

<400> SEQUENCE: 174

Pro Gly Thr Phe Asn Gly Gly Lys Leu Ala
1               5                   10

<210> SEQ ID NO 175
<211> LENGTH: 10
<212> TYPE: PRT
<213> ORGANISM: artificial
<220> FEATURE:
<223> OTHER INFORMATION: peptide

<400> SEQUENCE: 175

Pro Gly Thr Phe Asn Arg Gly Lys Leu Gln
1               5                   10

<210> SEQ ID NO 176
<211> LENGTH: 10
<212> TYPE: PRT
<213> ORGANISM: artificial
<220> FEATURE:
<223> OTHER INFORMATION: peptide

<400> SEQUENCE: 176

Pro Gly Thr Phe Asn Asp Gly Lys Leu Gly
1               5                   10

<210> SEQ ID NO 177
```

```
<211> LENGTH: 10
<212> TYPE: PRT
<213> ORGANISM: artificial
<220> FEATURE:
<223> OTHER INFORMATION: peptide

<400> SEQUENCE: 177

Pro Ser Thr Phe Asn Cys Met Lys Leu Pro
1               5                   10

<210> SEQ ID NO 178
<211> LENGTH: 10
<212> TYPE: PRT
<213> ORGANISM: artificial
<220> FEATURE:
<223> OTHER INFORMATION: peptide

<400> SEQUENCE: 178

Pro Ser Thr Phe Asn Cys Pro Lys Leu Gln
1               5                   10

<210> SEQ ID NO 179
<211> LENGTH: 10
<212> TYPE: PRT
<213> ORGANISM: artificial
<220> FEATURE:
<223> OTHER INFORMATION: peptide

<400> SEQUENCE: 179

Pro Ser Thr Phe Asn Leu Gly Lys Leu Ser
1               5                   10

<210> SEQ ID NO 180
<211> LENGTH: 10
<212> TYPE: PRT
<213> ORGANISM: artificial
<220> FEATURE:
<223> OTHER INFORMATION: peptide

<400> SEQUENCE: 180

Pro Ser Thr Phe Asn Gly Gly Lys Leu Pro
1               5                   10

<210> SEQ ID NO 181
<211> LENGTH: 10
<212> TYPE: PRT
<213> ORGANISM: artificial
<220> FEATURE:
<223> OTHER INFORMATION: peptide

<400> SEQUENCE: 181

Ser Cys Thr Phe Asn Leu His Lys Leu Cys
1               5                   10

<210> SEQ ID NO 182
<211> LENGTH: 10
<212> TYPE: PRT
<213> ORGANISM: artificial
<220> FEATURE:
<223> OTHER INFORMATION: peptide

<400> SEQUENCE: 182

Gln Asp Thr Phe Asn Arg Thr Lys Leu Cys
1               5                   10

<210> SEQ ID NO 183
<211> LENGTH: 10
```

-continued

```
<212> TYPE: PRT
<213> ORGANISM: artificial
<220> FEATURE:
<223> OTHER INFORMATION: peptide

<400> SEQUENCE: 183

Pro Thr Thr Phe Asn Arg Thr Lys Leu Met
1               5                   10

<210> SEQ ID NO 184
<211> LENGTH: 10
<212> TYPE: PRT
<213> ORGANISM: artificial
<220> FEATURE:
<223> OTHER INFORMATION: peptide

<400> SEQUENCE: 184

Phe Val Thr Phe Asn Gly Asp Lys Leu Met
1               5                   10

<210> SEQ ID NO 185
<211> LENGTH: 10
<212> TYPE: PRT
<213> ORGANISM: artificial
<220> FEATURE:
<223> OTHER INFORMATION: peptide

<400> SEQUENCE: 185

Arg Arg Thr Phe Asn Ser Arg Lys Leu Lys
1               5                   10

<210> SEQ ID NO 186
<211> LENGTH: 10
<212> TYPE: PRT
<213> ORGANISM: artificial
<220> FEATURE:
<223> OTHER INFORMATION: peptide

<400> SEQUENCE: 186

Ser Val Thr Phe Asn Ser Ala Lys Leu Gln
1               5                   10

<210> SEQ ID NO 187
<211> LENGTH: 10
<212> TYPE: PRT
<213> ORGANISM: artificial
<220> FEATURE:
<223> OTHER INFORMATION: peptide

<400> SEQUENCE: 187

Val Leu Thr Phe Asn Gly Ser Lys Leu Ala
1               5                   10

<210> SEQ ID NO 188
<211> LENGTH: 10
<212> TYPE: PRT
<213> ORGANISM: artificial
<220> FEATURE:
<223> OTHER INFORMATION: peptide

<400> SEQUENCE: 188

Pro Thr Thr Phe Asn Pro Ser Lys Leu Trp
1               5                   10

<210> SEQ ID NO 189
<211> LENGTH: 10
<212> TYPE: PRT
```

```
<213> ORGANISM: artificial
<220> FEATURE:
<223> OTHER INFORMATION: peptide

<400> SEQUENCE: 189

Pro Val Thr Phe Asn Glu Gly Lys Leu Phe
1               5                   10

<210> SEQ ID NO 190
<211> LENGTH: 10
<212> TYPE: PRT
<213> ORGANISM: artificial
<220> FEATURE:
<223> OTHER INFORMATION: peptide

<400> SEQUENCE: 190

Pro Thr Thr Phe Asn Gln Gly Lys Leu Gln
1               5                   10

<210> SEQ ID NO 191
<211> LENGTH: 10
<212> TYPE: PRT
<213> ORGANISM: artificial
<220> FEATURE:
<223> OTHER INFORMATION: peptide

<400> SEQUENCE: 191

Pro Gly Thr Phe Asn Gly Gly Lys Leu Gly
1               5                   10

<210> SEQ ID NO 192
<211> LENGTH: 10
<212> TYPE: PRT
<213> ORGANISM: artificial
<220> FEATURE:
<223> OTHER INFORMATION: peptide

<400> SEQUENCE: 192

Pro Leu Thr Phe Asn Asn Gly Lys Leu Ser
1               5                   10

<210> SEQ ID NO 193
<211> LENGTH: 10
<212> TYPE: PRT
<213> ORGANISM: artificial
<220> FEATURE:
<223> OTHER INFORMATION: peptide

<400> SEQUENCE: 193

Arg Ser Thr Phe Asn Gly Asp Lys Leu Asn
1               5                   10

<210> SEQ ID NO 194
<211> LENGTH: 10
<212> TYPE: PRT
<213> ORGANISM: artificial
<220> FEATURE:
<223> OTHER INFORMATION: peptide

<400> SEQUENCE: 194

Pro Thr Thr Phe Asn Val Asp Lys Leu Gly
1               5                   10

<210> SEQ ID NO 195
<211> LENGTH: 10
<212> TYPE: PRT
<213> ORGANISM: artificial
```

```
<220> FEATURE:
<223> OTHER INFORMATION: peptide

<400> SEQUENCE: 195

Pro Ile Thr Phe Asn Glu Pro Lys Leu Ala
1               5                   10

<210> SEQ ID NO 196
<211> LENGTH: 10
<212> TYPE: PRT
<213> ORGANISM: artificial
<220> FEATURE:
<223> OTHER INFORMATION: peptide

<400> SEQUENCE: 196

Trp Pro Thr Phe Asn Ala Gly Lys Leu Arg
1               5                   10

<210> SEQ ID NO 197
<211> LENGTH: 10
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is any amino acid other than P
<220> FEATURE:
<221> NAME/KEY: MISC_FEATURE
<222> LOCATION: (2)..(2)
<223> OTHER INFORMATION: Xaa is any amino acid other than T
<220> FEATURE:
<221> NAME/KEY: MISC_FEATURE
<222> LOCATION: (6)..(6)
<223> OTHER INFORMATION: Xaa is any amino acid other than Q
<220> FEATURE:
<221> NAME/KEY: MISC_FEATURE
<222> LOCATION: (7)..(7)
<223> OTHER INFORMATION: Xaa is any amino acid other than S
<220> FEATURE:
<221> NAME/KEY: MISC_FEATURE
<222> LOCATION: (10)..(10)
<223> OTHER INFORMATION: Xaa is any amino acid other than N

<400> SEQUENCE: 197

Xaa Xaa Thr Phe Asn Xaa Xaa Lys Leu Xaa
1               5                   10

<210> SEQ ID NO 198
<211> LENGTH: 7
<212> TYPE: PRT
<213> ORGANISM: artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is any amino acid other than P
<220> FEATURE:
<221> NAME/KEY: MISC_FEATURE
<222> LOCATION: (2)..(2)
<223> OTHER INFORMATION: Xaa is any amino acid other than T
<220> FEATURE:
<221> NAME/KEY: MISC_FEATURE
<222> LOCATION: (6)..(6)
<223> OTHER INFORMATION: Xaa is any amino acid other than Q
<220> FEATURE:
<221> NAME/KEY: MISC_FEATURE
<222> LOCATION: (7)..(7)
<223> OTHER INFORMATION: Xaa is any amino acid other than S

<400> SEQUENCE: 198
```

```
Xaa Xaa Thr Phe Asn Xaa Xaa
1               5

<210> SEQ ID NO 199
<211> LENGTH: 17
<212> TYPE: PRT
<213> ORGANISM: adeno-associated virus 8

<400> SEQUENCE: 199

Ala Asp Pro Pro Thr Thr Phe Asn Gln Ser Lys Leu Asn Ser Phe Ile
1               5                   10                  15

Thr

<210> SEQ ID NO 200
<211> LENGTH: 17
<212> TYPE: PRT
<213> ORGANISM: Artificial
<220> FEATURE:
<223> OTHER INFORMATION: peptide

<400> SEQUENCE: 200

Ala Asp Pro Val Gly Thr Phe Asn Glu Ala Lys Leu His Ser Phe Ile
1               5                   10                  15

Thr

<210> SEQ ID NO 201
<211> LENGTH: 17
<212> TYPE: PRT
<213> ORGANISM: Artificial
<220> FEATURE:
<223> OTHER INFORMATION: peptide

<400> SEQUENCE: 201

Ala Asp Pro Val Ser Thr Phe Asn Pro Ala Lys Leu Met Ser Phe Ile
1               5                   10                  15

Thr

<210> SEQ ID NO 202
<211> LENGTH: 17
<212> TYPE: PRT
<213> ORGANISM: Artificial
<220> FEATURE:
<223> OTHER INFORMATION: peptide

<400> SEQUENCE: 202

Ala Asp Pro Pro Leu Thr Phe Asn Cys Cys Lys Leu Asn Ser Phe Ile
1               5                   10                  15

Thr

<210> SEQ ID NO 203
<211> LENGTH: 17
<212> TYPE: PRT
<213> ORGANISM: Artificial
<220> FEATURE:
<223> OTHER INFORMATION: peptide

<400> SEQUENCE: 203

Ala Asp Pro Pro Val Thr Phe Asn Gln Asp Lys Leu Trp Ser Phe Ile
1               5                   10                  15

Thr

<210> SEQ ID NO 204
```

```
<211> LENGTH: 17
<212> TYPE: PRT
<213> ORGANISM: Artificial
<220> FEATURE:
<223> OTHER INFORMATION: peptide

<400> SEQUENCE: 204

Ala Asp Pro Pro Val Thr Phe Asn Ser Gly Lys Leu Cys Ser Phe Ile
1               5                   10                  15

Thr

<210> SEQ ID NO 205
<211> LENGTH: 17
<212> TYPE: PRT
<213> ORGANISM: Artificial
<220> FEATURE:
<223> OTHER INFORMATION: peptide

<400> SEQUENCE: 205

Ala Asp Pro Ile Gly Thr Phe Asn Gly Gln Lys Leu Cys Ser Phe Ile
1               5                   10                  15

Thr

<210> SEQ ID NO 206
<211> LENGTH: 17
<212> TYPE: PRT
<213> ORGANISM: Artificial
<220> FEATURE:
<223> OTHER INFORMATION: peptide

<400> SEQUENCE: 206

Ala Asp Pro Gln Val Thr Phe Asn Gly Gly Lys Leu Phe Ser Phe Ile
1               5                   10                  15

Thr

<210> SEQ ID NO 207
<211> LENGTH: 17
<212> TYPE: PRT
<213> ORGANISM: Artificial
<220> FEATURE:
<223> OTHER INFORMATION: peptide

<400> SEQUENCE: 207

Ala Asp Pro Pro Gly Thr Phe Asn Gly Gly Lys Leu Trp Ser Phe Ile
1               5                   10                  15

Thr

<210> SEQ ID NO 208
<211> LENGTH: 17
<212> TYPE: PRT
<213> ORGANISM: Artificial
<220> FEATURE:
<223> OTHER INFORMATION: peptide

<400> SEQUENCE: 208

Ala Asp Pro Pro Gly Thr Phe Asn Gly Gly Lys Leu Ala Ser Phe Ile
1               5                   10                  15

Thr

<210> SEQ ID NO 209
<211> LENGTH: 17
<212> TYPE: PRT
<213> ORGANISM: Artificial
<220> FEATURE:
```

```
<223> OTHER INFORMATION: peptide

<400> SEQUENCE: 209

Ala Asp Pro Pro Gly Thr Phe Asn Arg Gly Lys Leu Gln Ser Phe Ile
1               5                   10                  15

Thr

<210> SEQ ID NO 210
<211> LENGTH: 17
<212> TYPE: PRT
<213> ORGANISM: Artificial
<220> FEATURE:
<223> OTHER INFORMATION: peptide

<400> SEQUENCE: 210

Ala Asp Pro Pro Gly Thr Phe Asn Asp Gly Lys Leu Gly Ser Phe Ile
1               5                   10                  15

Thr

<210> SEQ ID NO 211
<211> LENGTH: 17
<212> TYPE: PRT
<213> ORGANISM: Artificial
<220> FEATURE:
<223> OTHER INFORMATION: peptide

<400> SEQUENCE: 211

Ala Asp Pro Pro Ser Thr Phe Asn Cys Met Lys Leu Pro Ser Phe Ile
1               5                   10                  15

Thr

<210> SEQ ID NO 212
<211> LENGTH: 17
<212> TYPE: PRT
<213> ORGANISM: Artificial
<220> FEATURE:
<223> OTHER INFORMATION: peptide

<400> SEQUENCE: 212

Ala Asp Pro Pro Ser Thr Phe Asn Cys Pro Lys Leu Gln Ser Phe Ile
1               5                   10                  15

Thr

<210> SEQ ID NO 213
<211> LENGTH: 17
<212> TYPE: PRT
<213> ORGANISM: Artificial
<220> FEATURE:
<223> OTHER INFORMATION: peptide

<400> SEQUENCE: 213

Ala Asp Pro Pro Ser Thr Phe Asn Leu Gly Lys Leu Ser Ser Phe Ile
1               5                   10                  15

Thr

<210> SEQ ID NO 214
<211> LENGTH: 17
<212> TYPE: PRT
<213> ORGANISM: Artificial
<220> FEATURE:
<223> OTHER INFORMATION: peptide

<400> SEQUENCE: 214
```

```
Ala Asp Pro Pro Ser Thr Phe Asn Gly Gly Lys Leu Pro Ser Phe Ile
1               5                   10                  15

Thr

<210> SEQ ID NO 215
<211> LENGTH: 17
<212> TYPE: PRT
<213> ORGANISM: Artificial
<220> FEATURE:
<223> OTHER INFORMATION: peptide

<400> SEQUENCE: 215

Ala Asp Pro Ser Cys Thr Phe Asn Leu His Lys Leu Cys Ser Phe Ile
1               5                   10                  15

Thr

<210> SEQ ID NO 216
<211> LENGTH: 17
<212> TYPE: PRT
<213> ORGANISM: Artificial
<220> FEATURE:
<223> OTHER INFORMATION: peptide

<400> SEQUENCE: 216

Ala Asp Pro Gln Asp Thr Phe Asn Arg Thr Lys Leu Cys Ser Phe Ile
1               5                   10                  15

Thr

<210> SEQ ID NO 217
<211> LENGTH: 17
<212> TYPE: PRT
<213> ORGANISM: Artificial
<220> FEATURE:
<223> OTHER INFORMATION: peptide

<400> SEQUENCE: 217

Ala Asp Pro Pro Thr Thr Phe Asn Arg Thr Lys Leu Met Ser Phe Ile
1               5                   10                  15

Thr

<210> SEQ ID NO 218
<211> LENGTH: 17
<212> TYPE: PRT
<213> ORGANISM: Artificial
<220> FEATURE:
<223> OTHER INFORMATION: peptide

<400> SEQUENCE: 218

Ala Asp Pro Phe Val Thr Phe Asn Gly Asp Lys Leu Met Ser Phe Ile
1               5                   10                  15

Thr

<210> SEQ ID NO 219
<211> LENGTH: 17
<212> TYPE: PRT
<213> ORGANISM: Artificial
<220> FEATURE:
<223> OTHER INFORMATION: peptide

<400> SEQUENCE: 219

Ala Asp Pro Arg Arg Thr Phe Asn Ser Arg Lys Leu Lys Ser Phe Ile
1               5                   10                  15

Thr
```

```
<210> SEQ ID NO 220
<211> LENGTH: 17
<212> TYPE: PRT
<213> ORGANISM: Artificial
<220> FEATURE:
<223> OTHER INFORMATION: peptide

<400> SEQUENCE: 220

Ala Asp Pro Ser Val Thr Phe Asn Ser Ala Lys Leu Gln Ser Phe Ile
1               5                   10                  15

Thr

<210> SEQ ID NO 221
<211> LENGTH: 17
<212> TYPE: PRT
<213> ORGANISM: Artificial
<220> FEATURE:
<223> OTHER INFORMATION: peptide

<400> SEQUENCE: 221

Ala Asp Pro Val Leu Thr Phe Asn Gly Ser Lys Leu Ala Ser Phe Ile
1               5                   10                  15

Thr

<210> SEQ ID NO 222
<211> LENGTH: 17
<212> TYPE: PRT
<213> ORGANISM: Artificial
<220> FEATURE:
<223> OTHER INFORMATION: peptide

<400> SEQUENCE: 222

Ala Asp Pro Pro Thr Thr Phe Asn Pro Ser Lys Leu Trp Ser Phe Ile
1               5                   10                  15

Thr

<210> SEQ ID NO 223
<211> LENGTH: 17
<212> TYPE: PRT
<213> ORGANISM: Artificial
<220> FEATURE:
<223> OTHER INFORMATION: peptide

<400> SEQUENCE: 223

Ala Asp Pro Pro Val Thr Phe Asn Glu Gly Lys Leu Phe Ser Phe Ile
1               5                   10                  15

Thr

<210> SEQ ID NO 224
<211> LENGTH: 17
<212> TYPE: PRT
<213> ORGANISM: Artificial
<220> FEATURE:
<223> OTHER INFORMATION: peptide

<400> SEQUENCE: 224

Ala Asp Pro Pro Thr Thr Phe Asn Gln Gly Lys Leu Gln Ser Phe Ile
1               5                   10                  15

Thr

<210> SEQ ID NO 225
<211> LENGTH: 17
```

```
<212> TYPE: PRT
<213> ORGANISM: Artificial
<220> FEATURE:
<223> OTHER INFORMATION: peptide

<400> SEQUENCE: 225

Ala Asp Pro Pro Gly Thr Phe Asn Gly Gly Lys Leu Gly Ser Phe Ile
1               5                   10                  15

Thr

<210> SEQ ID NO 226
<211> LENGTH: 17
<212> TYPE: PRT
<213> ORGANISM: Artificial
<220> FEATURE:
<223> OTHER INFORMATION: peptide

<400> SEQUENCE: 226

Ala Asp Pro Pro Leu Thr Phe Asn Asn Gly Lys Leu Ser Ser Phe Ile
1               5                   10                  15

Thr

<210> SEQ ID NO 227
<211> LENGTH: 17
<212> TYPE: PRT
<213> ORGANISM: Artificial
<220> FEATURE:
<223> OTHER INFORMATION: peptide

<400> SEQUENCE: 227

Ala Asp Pro Arg Ser Thr Phe Asn Gly Asp Lys Leu Asn Ser Phe Ile
1               5                   10                  15

Thr

<210> SEQ ID NO 228
<211> LENGTH: 17
<212> TYPE: PRT
<213> ORGANISM: Artificial
<220> FEATURE:
<223> OTHER INFORMATION: peptide

<400> SEQUENCE: 228

Ala Asp Pro Pro Thr Thr Phe Asn Val Asp Lys Leu Gly Ser Phe Ile
1               5                   10                  15

Thr

<210> SEQ ID NO 229
<211> LENGTH: 17
<212> TYPE: PRT
<213> ORGANISM: Artificial
<220> FEATURE:
<223> OTHER INFORMATION: peptide

<400> SEQUENCE: 229

Ala Asp Pro Pro Ile Thr Phe Asn Glu Pro Lys Leu Ala Ser Phe Ile
1               5                   10                  15

Thr

<210> SEQ ID NO 230
<211> LENGTH: 17
<212> TYPE: PRT
<213> ORGANISM: Artificial
<220> FEATURE:
<223> OTHER INFORMATION: peptide
```

```
<400> SEQUENCE: 230

Ala Asp Pro Trp Pro Thr Phe Asn Ala Gly Lys Leu Arg Ser Phe Ile
1               5                   10                  15

Thr

<210> SEQ ID NO 231
<211> LENGTH: 17
<212> TYPE: PRT
<213> ORGANISM: adeno-associated virus 8

<400> SEQUENCE: 231

Ala Asp Pro Pro Thr Thr Phe Asn Gln Ser Lys Leu Asn Ser Phe Ile
1               5                   10                  15

Thr

<210> SEQ ID NO 232
<211> LENGTH: 17
<212> TYPE: PRT
<213> ORGANISM: Artificial Sequence
<220> FEATURE:
<223> OTHER INFORMATION: h1 synthesized peptide

<400> SEQUENCE: 232

Ala Asp Pro Val Gly Thr Phe Asn Glu Ala Lys Leu His Ser Phe Ile
1               5                   10                  15

Thr

<210> SEQ ID NO 233
<211> LENGTH: 17
<212> TYPE: PRT
<213> ORGANISM: Artificial Sequence
<220> FEATURE:
<223> OTHER INFORMATION: h9 synthesized peptide

<400> SEQUENCE: 233

Ala Asp Pro Val Ser Thr Phe Asn Pro Ala Lys Leu Met Ser Phe Ile
1               5                   10                  15

Thr

<210> SEQ ID NO 234
<211> LENGTH: 17
<212> TYPE: PRT
<213> ORGANISM: Artificial Sequence
<220> FEATURE:
<223> OTHER INFORMATION: d5 synthesized peptide

<400> SEQUENCE: 234

Ala Asp Pro Pro Leu Thr Phe Asn Cys Cys Lys Leu Asn Ser Phe Ile
1               5                   10                  15

Thr

<210> SEQ ID NO 235
<211> LENGTH: 17
<212> TYPE: PRT
<213> ORGANISM: Artificial Sequence
<220> FEATURE:
<223> OTHER INFORMATION: d4 synthesized peptide

<400> SEQUENCE: 235

Ala Asp Pro Pro Val Thr Phe Asn Gln Asp Lys Leu Trp Ser Phe Ile
1               5                   10                  15
```

Thr

<210> SEQ ID NO 236
<211> LENGTH: 17
<212> TYPE: PRT
<213> ORGANISM: Artificial Sequence
<220> FEATURE:
<223> OTHER INFORMATION: h6 synthesized peptide

<400> SEQUENCE: 236

Ala Asp Pro Pro Val Thr Phe Asn Ser Gly Lys Leu Cys Ser Phe Ile
1               5                   10                  15

Thr

<210> SEQ ID NO 237
<211> LENGTH: 17
<212> TYPE: PRT
<213> ORGANISM: Artificial Sequence
<220> FEATURE:
<223> OTHER INFORMATION: h4 synthesized peptide

<400> SEQUENCE: 237

Ala Asp Pro Ile Gly Thr Phe Asn Gly Gln Lys Leu Cys Ser Phe Ile
1               5                   10                  15

Thr

<210> SEQ ID NO 238
<211> LENGTH: 17
<212> TYPE: PRT
<213> ORGANISM: Artificial Sequence
<220> FEATURE:
<223> OTHER INFORMATION: h5 synthesized peptide

<400> SEQUENCE: 238

Ala Asp Pro Gln Val Thr Phe Asn Gly Gly Lys Leu Phe Ser Phe Ile
1               5                   10                  15

Thr

<210> SEQ ID NO 239
<211> LENGTH: 17
<212> TYPE: PRT
<213> ORGANISM: Artificial Sequence
<220> FEATURE:
<223> OTHER INFORMATION: h3 synthesized peptide

<400> SEQUENCE: 239

Ala Asp Pro Pro Gly Thr Phe Asn Gly Gly Lys Leu Trp Ser Phe Ile
1               5                   10                  15

Thr

<210> SEQ ID NO 240
<211> LENGTH: 17
<212> TYPE: PRT
<213> ORGANISM: Artificial Sequence
<220> FEATURE:
<223> OTHER INFORMATION: h8 synthesized peptide

<400> SEQUENCE: 240

Ala Asp Pro Pro Gly Thr Phe Asn Gly Gly Lys Leu Ala Ser Phe Ile
1               5                   10                  15

Thr

<210> SEQ ID NO 241

-continued

```
<211> LENGTH: 17
<212> TYPE: PRT
<213> ORGANISM: Artificial Sequence
<220> FEATURE:
<223> OTHER INFORMATION: h7 synthesized peptide

<400> SEQUENCE: 241

Ala Asp Pro Pro Gly Thr Phe Asn Arg Gly Lys Leu Gln Ser Phe Ile
1               5                   10                  15

Thr

<210> SEQ ID NO 242
<211> LENGTH: 17
<212> TYPE: PRT
<213> ORGANISM: Artificial Sequence
<220> FEATURE:
<223> OTHER INFORMATION: d6 synthesized peptide

<400> SEQUENCE: 242

Ala Asp Pro Pro Gly Thr Phe Asn Asp Gly Lys Leu Gly Ser Phe Ile
1               5                   10                  15

Thr

<210> SEQ ID NO 243
<211> LENGTH: 17
<212> TYPE: PRT
<213> ORGANISM: Artificial Sequence
<220> FEATURE:
<223> OTHER INFORMATION: h2 synthesized peptide

<400> SEQUENCE: 243

Ala Asp Pro Pro Ser Thr Phe Asn Cys Met Lys Leu Pro Ser Phe Ile
1               5                   10                  15

Thr

<210> SEQ ID NO 244
<211> LENGTH: 17
<212> TYPE: PRT
<213> ORGANISM: Artificial Sequence
<220> FEATURE:
<223> OTHER INFORMATION: h11 synthesized peptide

<400> SEQUENCE: 244

Ala Asp Pro Pro Ser Thr Phe Asn Cys Pro Lys Leu Gln Ser Phe Ile
1               5                   10                  15

Thr

<210> SEQ ID NO 245
<211> LENGTH: 17
<212> TYPE: PRT
<213> ORGANISM: Artificial Sequence
<220> FEATURE:
<223> OTHER INFORMATION: d1 synthesized peptide

<400> SEQUENCE: 245

Ala Asp Pro Pro Ser Thr Phe Asn Leu Gly Lys Leu Ser Ser Phe Ile
1               5                   10                  15

Thr

<210> SEQ ID NO 246
<211> LENGTH: 17
<212> TYPE: PRT
<213> ORGANISM: Artificial Sequence
<220> FEATURE:
```

<223> OTHER INFORMATION: d7 synthesized peptide

<400> SEQUENCE: 246

Ala Asp Pro Pro Ser Thr Phe Asn Gly Gly Lys Leu Pro Ser Phe Ile
1               5                   10                  15

Thr

<210> SEQ ID NO 247
<211> LENGTH: 17
<212> TYPE: PRT
<213> ORGANISM: Artificial Sequence
<220> FEATURE:
<223> OTHER INFORMATION: h12 synthesized peptide

<400> SEQUENCE: 247

Ala Asp Pro Ser Cys Thr Phe Asn Leu His Lys Leu Cys Ser Phe Ile
1               5                   10                  15

Thr

<210> SEQ ID NO 248
<211> LENGTH: 17
<212> TYPE: PRT
<213> ORGANISM: Artificial Sequence
<220> FEATURE:
<223> OTHER INFORMATION: h10 synthesized peptide

<400> SEQUENCE: 248

Ala Asp Pro Gln Asp Thr Phe Asn Arg Thr Lys Leu Cys Ser Phe Ile
1               5                   10                  15

Thr

<210> SEQ ID NO 249
<211> LENGTH: 17
<212> TYPE: PRT
<213> ORGANISM: Artificial Sequence
<220> FEATURE:
<223> OTHER INFORMATION: d3 synthesized peptide

<400> SEQUENCE: 249

Ala Asp Pro Pro Thr Thr Phe Asn Arg Thr Lys Leu Met Ser Phe Ile
1               5                   10                  15

Thr

<210> SEQ ID NO 250
<211> LENGTH: 17
<212> TYPE: PRT
<213> ORGANISM: Artificial Sequence
<220> FEATURE:
<223> OTHER INFORMATION: xx4 synthesized peptide

<400> SEQUENCE: 250

Ala Asp Pro Pro Thr Thr Phe Asn Arg Thr Lys Leu Met Ser Phe Ile
1               5                   10                  15

Thr

<210> SEQ ID NO 251
<211> LENGTH: 17
<212> TYPE: PRT
<213> ORGANISM: Artificial Sequence
<220> FEATURE:
<223> OTHER INFORMATION: xx2 synthesized peptide

<400> SEQUENCE: 251

```
Ala Asp Pro Arg Arg Thr Phe Asn Ser Arg Lys Leu Lys Ser Phe Ile
1               5                   10                  15

Thr

<210> SEQ ID NO 252
<211> LENGTH: 17
<212> TYPE: PRT
<213> ORGANISM: Artificial Sequence
<220> FEATURE:
<223> OTHER INFORMATION: e2 synthetized peptide

<400> SEQUENCE: 252

Ala Asp Pro Ser Val Thr Phe Asn Ser Ala Lys Leu Gln Ser Phe Ile
1               5                   10                  15

Thr

<210> SEQ ID NO 253
<211> LENGTH: 17
<212> TYPE: PRT
<213> ORGANISM: Artificial Sequence
<220> FEATURE:
<223> OTHER INFORMATION: e1 synthesized peptide

<400> SEQUENCE: 253

Ala Asp Pro Val Leu Thr Phe Asn Gly Ser Lys Leu Ala Ser Phe Ile
1               5                   10                  15

Thr

<210> SEQ ID NO 254
<211> LENGTH: 17
<212> TYPE: PRT
<213> ORGANISM: Artificial Sequence
<220> FEATURE:
<223> OTHER INFORMATION: xx3 synthesized peptide

<400> SEQUENCE: 254

Ala Asp Pro Pro Thr Thr Phe Asn Pro Ser Lys Leu Trp Ser Phe Ile
1               5                   10                  15

Thr

<210> SEQ ID NO 255
<211> LENGTH: 17
<212> TYPE: PRT
<213> ORGANISM: Artificial Sequence
<220> FEATURE:
<223> OTHER INFORMATION: e3 synthesized peptide

<400> SEQUENCE: 255

Ala Asp Pro Pro Val Thr Phe Asn Glu Gly Lys Leu Phe Ser Phe Ile
1               5                   10                  15

Thr

<210> SEQ ID NO 256
<211> LENGTH: 17
<212> TYPE: PRT
<213> ORGANISM: Artificial Sequence
<220> FEATURE:
<223> OTHER INFORMATION: e5 synthesized peptide

<400> SEQUENCE: 256

Ala Asp Pro Pro Thr Thr Phe Asn Gln Gly Lys Leu Gln Ser Phe Ile
1               5                   10                  15

Thr
```

<210> SEQ ID NO 257
<211> LENGTH: 17
<212> TYPE: PRT
<213> ORGANISM: Artificial Sequence
<220> FEATURE:
<223> OTHER INFORMATION: xx1 synthesized peptide

<400> SEQUENCE: 257

Ala Asp Pro Pro Gly Thr Phe Asn Gly Gly Lys Leu Gly Ser Phe Ile
1               5                   10                  15

Thr

<210> SEQ ID NO 258
<211> LENGTH: 17
<212> TYPE: PRT
<213> ORGANISM: Artificial Sequence
<220> FEATURE:
<223> OTHER INFORMATION: xx5 synthesized peptide

<400> SEQUENCE: 258

Ala Asp Pro Pro Leu Thr Phe Asn Asn Gly Lys Leu Ser Ser Phe Ile
1               5                   10                  15

Thr

<210> SEQ ID NO 259
<211> LENGTH: 17
<212> TYPE: PRT
<213> ORGANISM: Artificial Sequence
<220> FEATURE:
<223> OTHER INFORMATION: hi-C synthesized peptide

<400> SEQUENCE: 259

Ala Asp Pro Arg Ser Thr Phe Asn Gly Asp Lys Leu Asn Ser Phe Ile
1               5                   10                  15

Thr

<210> SEQ ID NO 260
<211> LENGTH: 17
<212> TYPE: PRT
<213> ORGANISM: Artificial Sequence
<220> FEATURE:
<223> OTHER INFORMATION: hi-A synthesized peptide

<400> SEQUENCE: 260

Ala Asp Pro Pro Thr Thr Phe Asn Val Asp Lys Leu Gly Ser Phe Ile
1               5                   10                  15

Thr

<210> SEQ ID NO 261
<211> LENGTH: 17
<212> TYPE: PRT
<213> ORGANISM: Artificial Sequence
<220> FEATURE:
<223> OTHER INFORMATION: hi-B synthesized peptide

<400> SEQUENCE: 261

Ala Asp Pro Pro Ile Thr Phe Asn Glu Pro Lys Leu Ala Ser Phe Ile
1               5                   10                  15

Thr

<210> SEQ ID NO 262
<211> LENGTH: 17

```
<212> TYPE: PRT
<213> ORGANISM: Artificial Sequence
<220> FEATURE:
<223> OTHER INFORMATION: hi-e synthesized peptide

<400> SEQUENCE: 262

Ala Asp Pro Trp Pro Thr Phe Asn Ala Gly Lys Leu Arg Ser Phe Ile
1               5                   10                  15

Thr
```

METHODS AND COMPOSITIONS FOR ANTIBODY-EVADING VIRUS VECTORS

STATEMENT OF PRIORITY

This application is a 35 U.S.C. § 371 national phase application of International Application Serial No. PCT/US2019/020053, filed Feb. 28, 2019, which claims the benefit, under 35 U.S.C. § 119(e), of U.S. Provisional Application No. 62/687,583, filed on Jun. 20, 2018, and U.S. Provisional Application No. 62/636,598, filed on Feb. 28, 2018, the entire contents of each of which are incorporated by reference herein.

STATEMENT OF GOVERNMENT SUPPORT

This invention was made with government funding under Grant Nos. HL112761, GM082946, and HL089221 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-838_11252024_ST25.txt, 241,556 bytes in size, generated on Nov. 25, 2024 and filed electronically, is provided in lieu of a paper copy. This Sequence Listing is hereby incorporated herein by reference into the specification for its disclosures.

FIELD

The present disclosure relates to modified capsid proteins from adeno-associated virus (AAV) and virus capsids and virus vectors comprising the same. In particular, the disclosure relates to modified AAV capsid proteins and capsids comprising the same that can be incorporated into virus vectors to confer a phenotype of evasion of neutralizing antibodies without decreased transduction efficiency.

BACKGROUND

Host-derived pre-existing antibodies generated upon natural encounter of AAV or recombinant AAV vectors prevent first time as well as repeat administration of AAV vectors as vaccines and/or for gene therapy. Serological studies reveal a high prevalence of antibodies in the human population worldwide with about 67% of people having antibodies against AAV1, 72% against AAV2, and about 40% against AAV5 through AAV9.

Furthermore, in gene therapy, certain clinical scenarios involving gene silencing or tissue degeneration may require multiple AAV vector administrations to sustain long term expression of the transgene. Compositions and methods to increase the efficiency of gene therapy involving rAAV would therefore be broadly useful. To facilitate effective clinical use, recombinant AAV vectors which evade antibody recognition (AAVe) are required. Such AAV vectors will help a) expand the eligible cohort of patients suitable for AAV-based gene therapy and b) allow multiple, repeat administrations of AAV-based gene therapy vectors.

Provided herein are methods and compositions comprising an adeno-associated virus (AAV) capsid protein that overcome previous shortcomings in the art. The AAV capsid proteins comprise one or more amino acid substitutions, wherein the substitutions introduce into an AAV vector comprising these modified capsid proteins the ability to evade host antibodies.

SUMMARY

Despite recent success in gene delivery with rAAV particles, pre-existing antibodies, which are able to neutralize rAAV particles administered to a subject, represent a significant challenge. Compositions of rAAV particles and methods to decrease the interaction with, or escape altogether, these neutralizing antibodies would be useful at least for the reason that a lower concentration of rAAV particles that have the ability to evade or escape neutralizing antibodies would be required to be administered to a subject in need of gene therapy compared to rAAV particles without such an ability.

In one aspect, the present disclosure provides an adeno-associated virus (AAV) capsid protein, wherein the capsid protein comprises a substitution resulting in the amino acid sequence: $X^1$—$X^2$-T-F—N—$X^3$—$X^4$—K-L-$X^5$ (SEQ ID NO:197) at the amino acids corresponding to amino acid positions 661 to 670 of the native AAV8 capsid protein (VP1 numbering) based on the reference amino acid sequence of AAV8 identified as SEQ ID NO:8 and corresponding to amino acid positions 659 to 668 of the native AAV9 capsid protein (VP1 numbering) based on the reference amino acid sequence of AAV9 identified as SEQ ID NO:26 or at the equivalent amino acid positions in the capsid protein of any other AAV serotype, wherein $X^1$ is any amino acid other than P; wherein $X^2$ is any amino acid other than T; wherein $X^3$ is any amino acid other than Q; wherein $X^4$ is any amino acid other than S; and/or wherein $X^5$ is any amino acid other than N.

As an additional aspect, the present disclosure provides an adeno-associated virus (AAV) capsid protein, wherein the capsid protein comprises a substitution resulting in the amino acid sequence: VGTFNEAKLH (h1; SEQ ID NO:166), VSTFNPAKLM (h9; SEQ ID NO:167), PLTFNCCKLN (d5; SEQ ID NO:168), PVTFNQDKLW (d4; SEQ ID NO:169), PVTFNSGKLC (h6; SEQ ID NO:170), IGTFNGQKLC (h4; SEQ ID NO:171), QVTFNGGKLF (h5; SEQ ID NO:172), PGTFNGGKLW (h3; SEQ ID NO:173), PGTFNGGKLA (h8; SEQ ID NO:174), PGTFNRGKLQ (h7; SEQ ID NO:175), PGTFNDGKLG (d6; SEQ ID NO:176), PSTFNCMKLP (h2; SEQ ID NO:177), PSTFNCPKLQ (h11; SEQ ID NO:178), PSTFNLGKLS (d1; SEQ ID NO:179), PSTFNGGKLP (d7; SEQ ID NO:180), SCTFNLHKLC (h12; SEQ ID NO:181), QDTFNRTKLC (h10; SEQ ID NO:182), PTTFNRTKLM (d3; SEQ ID NO:183), FVTFNGDKLM (xx4; SEQ ID NO:184), RRTFNSRKLK (xx2; SEQ ID NO:185), SVTFNSAKLQ (e2; SEQ ID NO:186), VLTFNGSKLA (e1; SEQ ID NO:187), PTTFNPSKLW (xx3; SEQ ID NO:188), PVTFNEGKLF (e3; SEQ ID NO:189), PTTFNQGKLQ (e5; SEQ ID NO:190), PGTFNGGKLG (xx1; SEQ ID NO:191), PLTFNNGKLS (xx5; SEQ ID NO:192), RSTFNGDKLN (hi-C; SEQ ID NO:193), PTTFNVDKLG (hi-A; SEQ ID NO:194), PITFNEPKLA (hi-B; SEQ ID NO:195), or WPTFNAGKLR (hi-e; SEQ ID NO:196) at the amino acids corresponding to amino acid positions 661 to 670 of the native AAV8 capsid protein (VP1 numbering) based on the reference amino acid sequence of AAV8 identified as SEQ ID NO:8 and corresponding to amino acid positions 659 to 668 of the native AAV9 capsid protein (VP1 numbering) based on the reference amino acid sequence of AAV9 identified as SEQ ID NO:26 or at the equivalent amino acid positions in the capsid protein of any other AAV serotype.

As an additional aspect, the present disclosure provides an AAV capsid protein, wherein the capsid protein comprises a substitution resulting in the amino acid sequence: $X^1$—$X^2$-T-F—N—$X^3$—$X^4$ (SEQ ID NO:198) at the amino acids corresponding to amino acid positions 661 to 667 of the native AAV8 capsid protein (VP1 numbering) based on the reference amino acid sequence of AAV8 identified as SEQ ID NO:8 and corresponding to amino acid positions 659 to 665 of the native AAV9 capsid protein (VP1 numbering) based on the reference amino acid sequence of AAV9 identified as SEQ ID NO:26 or at the equivalent amino acid positions in the capsid protein of any other AAV serotype, wherein $X^1$ is any amino acid other than P; wherein $X^2$ is any amino acid other than T; wherein $X^3$ is any amino acid other than Q; and/or wherein $X^4$ is any amino acid other than S.

In addition, the present disclosure is based, at least in part, on the generation of antigenic footprints, or maps, of neutralizing antibodies on AAV particles, and the development of rAAV particles with amino acid substitutions within these footprints that result in a decreased reactivity to one or more neutralizing antibodies. In particular, the inventors of this disclosure developed antigenic footprints in the 5-fold region of AAV particles.

Accordingly, provided herein is a recombinant adeno-associated virus (rAAV) capsid protein comprising a modified 5-fold region, wherein the modified 5-fold region comprises one or more amino acid substitutions. In some embodiments, one or more amino acid substitutions in a modified 5-fold region results in decreased reactivity to a neutralizing antibody compared to an AAV particle that comprises capsid protein (i.e., VP) without a modified 5-fold region.

In some embodiments, a rAAV is of serotype 1, and the one or more amino acid substitutions are at positions 250-258, 324-333, 371, 372, 546-550, 557, 655-674 or 716-721 (VP1 numbering) based on the reference amino acid sequence of AAV1 identified as SEQ ID NO:18. In some embodiments, a rAAV is of serotype 2, and the one or more amino acid substitutions are at positions 250-258, 323-332, 370, 371, 545-548, 556, 655-673 or 715-720 (VP1 numbering) based on the reference amino acid sequence of AAV2 identified as SEQ ID NO:19. In some embodiments, a rAAV is of serotype 5, and the one or more amino acid substitutions are at positions 240-248, 314-323, 372, 373, 532-535, 546, 644-662 or 704-709 (VP1 numbering) based on the reference amino acid sequence of AAV5 identified as SEQ ID NO:22. In some embodiments where a rAAV is of serotype 2, and the one or more amino acid substitutions are at positions 250-258, 323-332, 370, 371, 545-548, 556, 655-673 or 715-720, a neutralizing antibody is AVB. In some embodiments where a rAAV is of serotype 5, and the one or more amino acid substitutions are at positions 240-248, 314-323, 372, 373, 532-535, 546, 644-662 or 704-709, a neutralizing antibody is AVB.

In some embodiments, a rAAV is of serotype 9, and the one or more amino acid substitutions are at positions 251-255, 264, 325-334 or 656-674 (VP1 numbering) based on the reference amino acid sequence of AAV9 identified as SEQ ID NO:26. In some embodiments where a rAAV is of serotype 9, and the one or more amino acid substitutions are at positions 251-255, 264, 325-334 or 656-674, a neutralizing antibody is CSAL9.

In some embodiments, a rAAV is of serotype 8, and the one or more amino acid substitutions are at positions 252-266, 326-335, 658-676 or 720 (VP1 numbering) based on the reference amino acid sequence of AAV8 identified as SEQ ID NO:25. In some embodiments where rAAV is of serotype 8, and the one or more amino acid substitutions are at positions 252-266, 326-335, 658-676 or 720, a neutralizing antibody is HL2372. In some embodiments, a rAAV is of serotype 9, and the one or more amino acid substitutions are at positions 251-266,325-334, 657-673 or 718 (VP1 numbering) based on the reference amino acid sequence of AAV8 identified as SEQ ID NO:26. In some embodiments where rAAV is of serotype 9, and the one or more amino acid substitutions are at positions 251-266,325-334, 657-673 or 718, a neutralizing antibody is HL2372.

In some embodiments, a rAAV is of serotype 5, and the one or more amino acid substitutions are at positions 218, 240-258, 261, 263, 267, 279, 331, 350, 355-360, 364, 365, 377, 378, 395, 429-432, 437, 450, 451, 453-456, 458, 459, 530-543, 545-548, 639, 641, 642, 648-651, 653-658, 660-662, 697-700 or 704-71 (VP1 numbering) based on the reference amino acid sequence of AAV8 identified as SEQ ID NO:22. In some embodiments where a rAAV is of serotype 5, and the one or more amino acid substitutions are at positions 218, 240-258, 261, 263, 267, 279, 331, 350, 355-360, 364, 365, 377, 378, 395, 429-432, 437, 450, 451, 453-456, 458, 459, 530-543, 545-548, 639, 641, 642, 648-651, 653-658, 660-662, 697-700 or 704-71, a neutralizing antibody is ADK5a.

In some embodiments, a rAAV is of serotype 5, and the one or more amino acid substitutions are at positions 241-248, 313-319, 321, 323, 355, 356, 358-362, 440-443, 446-449, 530-548, 645-651, 653-661, 697, 698 or 704-712 (VP1 numbering) based on the reference amino acid sequence of AAV8 identified as SEQ ID NO:22. In some embodiments where rAAV is of serotype 5, and the one or more amino acid substitutions are at positions 241-248, 313-319, 321, 323, 355, 356, 358-362, 440-443, 446-449, 530-548, 645-651, 653-661, 697, 698 or 704-712, a neutralizing antibody ADK5b.

The present disclosure also provides an AAV capsid comprising the AAV capsid protein of this disclosure. Further provided herein is a viral vector comprising the AAV capsid of this disclosure as well as a composition comprising the AAV capsid protein, AAV capsid and/or viral vector of this disclosure in a pharmaceutically acceptable carrier.

The present disclosure additionally provides a method of introducing a nucleic acid into a cell in the presence of antibodies against the AAV capsid, comprising contacting the cell with the viral vector of this disclosure. The cell can be in a subject and in some embodiments, the subject can be a human subject.

These and other aspects of the invention are addressed in more detail in the description of the invention set forth below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1 shows different amino acid residues that were evolved following selection of AAV capsid libraries randomized in each position (highlighted). From top to bottom, the sequences shown in FIG. 1 correspond to the following sequences: ADPPTTFNQSKLNSFIT (WT AAV8; SEQ ID NO:231), ADPVGTFNEAKLHSFIT (h1; SEQ ID NO:232), ADPVSTFNPAKLMSFIT (h9; SEQ ID NO:233), ADPPLTFNCCKLNSFIT (d5; SEQ ID NO:234), ADPPVTFNQDKLWSFIT (d4; SEQ ID NO:235), ADPPVTFNSGKLCSFIT (h6; SEQ ID NO:236), ADPIGTFNGQKLCSFIT (h4; SEQ ID NO:237), ADPQVTFNGGKLFSFIT (h5; SEQ ID NO:238), ADPPGTFNGGKLWSFIT (h3; SEQ ID NO:239), ADPPGTFNGGKLASFIT (h8; SEQ ID NO:240), ADPPGTFNRGKLQSFIT (h7; SEQ ID NO:241), ADPPGTFNDGKLGSFIT (d6; SEQ ID NO:242), ADPPSTFNCMKLPSFIT (h2; SEQ ID NO:243), ADPPSTFNCPKLQSFIT (h11; SEQ ID NO:244), ADPPSTFNLGKLSSFIT (d1; SEQ ID NO:245), ADPPSTFNGGKLPSFIT (d7; SEQ ID NO:246), ADPSCTFNLHKLCSFIT (h12; SEQ ID NO:247), ADPQDTFNRTKLCSFIT (h10; SEQ ID NO:248), ADPPTTFNRTKLMSFIT (d3; SEQ ID NO:249), ADPPTTFNRTKLMSFIT (xx4; SEQ ID NO:250), ADPRRTFNSRKLKSFIT (xx2; SEQ ID NO:251), ADPSVTFNSAKLQSFIT (e2; SEQ ID NO:252), ADPVLTFNGSKLASFIT (e1; SEQ ID NO:253), ADPPTTFNPSKLWSFIT (xx3; SEQ ID NO:254), ADPPVTFNEGKLFSFIT (e3; SEQ ID NO:255), ADPPTTFNQGKLQSFIT (e5; SEQ ID NO:256), ADPPGTFNGGKLGSFIT (xxi; SEQ ID NO:257), ADPPLTFNNGKLSSFIT (xx5; SEQ ID NO:258), ADPRSTFNGDKLNSFIT (hi-C; SEQ ID NO:259), ADPPTTFNVDKLGSFIT (hi-A; SEQ ID NO:260), ADPPITFNEPKLASFIT (hi-B; SEQ ID NO:261), or ADPWPTFNAGKLRSFIT (hi-e; SEQ ID NO:262).

Definitions

Figure 2:
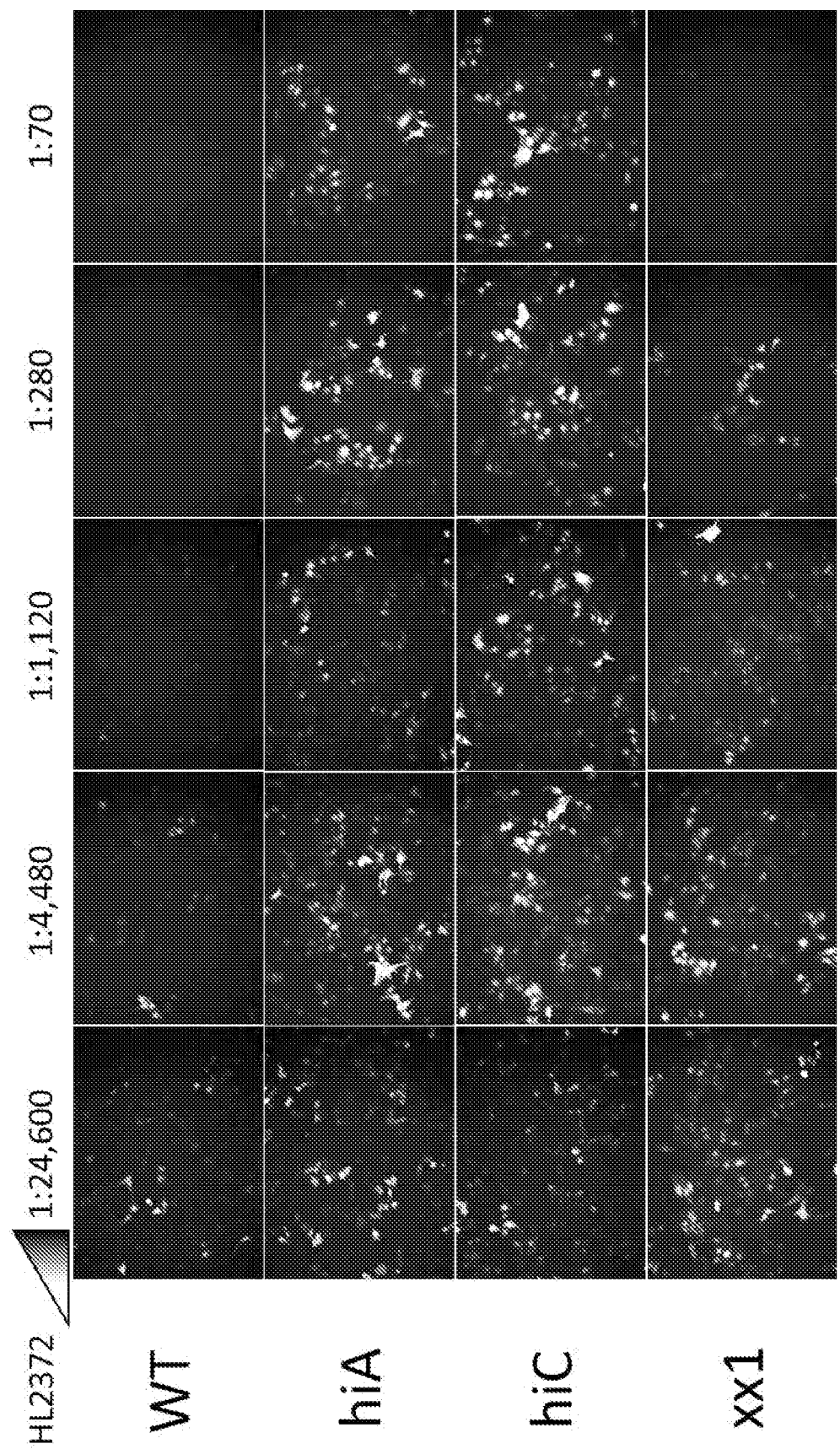
FIG. 2 shows the evaluation of antibody escape capability of exemplary mutant AAV capsids from sequences identified as shown in FIG. 1. Briefly, exemplary AAV mutants packaging GFP sequences were incubated with increasingly concentrated amounts of a neutralizing antibody HL2372 (shown as fold dilutions). The capsid containing the wild type version of the amino acid sequence was readily neutralized in highly diluted samples (at 1:4480); GFP expression (white dots) in cultured cells is markedly reduced. In contrast, mutants hiA and hiC and to a lesser extent xx1 were not neutralized, GFP expression was robust supporting the notion that these evolved vari with respect to VP1 capsid subunit numbering. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

The following terms are used in the description herein and the appended claims: The indefinite articles "a" and "an," as used herein in the specification and in the claims, unless clearly indicated to the contrary, should be understood to mean "at least one." The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or"). The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 10%, 15%, 20%, 25%, 35%, 50%, 75%, 80%, 85%, 90%, 95%, 97% or more.

As used herein, the terms "enhance," "enhances," "enhancement" and similar terms indicate an increase of at least about 10%, 15%, 20%, 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera *Protoparvovirus, Erythroparvovirus, Bocaparvirus,* and Densovirus subfamily. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers; Cotmore et al. Archives of Virology DOI 10.1007/s00705-013-1914-I).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, avian AAV, bovine AAV, canine AAV, equine AAV, ovine AAV, and any other AAV now known or later discovered. See, e.g., BERNARD N. FIELDS et al., *VIROLOGY*, volume 2, chapter 69 (4th ed., Lippincott-Raven Publishers). A number of AAV serotypes and clades have been identified (see, e.g., Gao et al., (2004) *J. Virology* 78:6381-6388; Moris et al., (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC 001729, NC_001863, NC 001829, NC 001862, NC 000883, NC_001701, NC 001510, NC 006152, NC_006261, AF063497, U89790, AF043303, AF028705, AF028704, J02275, J01901, J02275, X01457, AF288061, AH009962, AY028226, AY028223, NC 001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci.* USA 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. The capsid structures of autonomous parvoviruses and AAV are described in more detail in BERNARD N. FIELDS et al., *VIROLOGY*, volume 2, chapters 69 & 70 (4th ed., Lippincott-Raven Publishers). See also, description of the crystal structure of AAV2 (Xie et al., (2002) *Proc. Nat. Acad. Sci.* 99:10405-10), AAV9 (DiMattia et al., (2012) *J. Virol.* 86:6947-6958), AAV8 (Nam et al., (2007) *J. Virol.* 81:12260-12271), AAV6 (Ng et al., (2010) *J. Virol.* 84:12945-12957), AAV5 (Govindasamy et al., (2013) *J. Virol.* 87, 11187-11199), AAV4 (Govindasamy et al., (2006) *J. Virol.* 80:11556-11570), AAV3B (Lerch et al., (2010) *J. Virol.* 403: 26-36), BPV(Kailasan et al., (2015) *J. Virol.* 89:2603-2614) and CPV (Xie et al., (1996) *J. Mol. Biol.* 6:497-520 and Tsao et al., (1991) *Science* 251: 1456-64).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the disclosure exhibits tropism for or transduces, respectively, tissues throughout the body (e.g., brain, lung, skeletal muscle, heart, liver, kidney and/or pancreas). In embodiments of the disclosure, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically).

Unless indicated otherwise, "efficient transduction" or "efficient tropism," or similar terms, can be determined by reference to a suitable control (e.g., at least about 50%, 60%, 70%, 80%, 85%, 90%, 95% or more of the transduction or tropism, respectively, of the control). In particular embodiments, the virus vector efficiently transduces or has efficient tropism for skeletal muscle, cardiac muscle, diaphragm muscle, pancreas (including n-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, the disclosure can be practiced to identify viral vectors that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the disclosure may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is 20% or less, 10% or less, 5% or less, 1% or less, 0.10% or less of the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it is meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the disclosure. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the methods and compositions of the present disclosure.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the disclosure. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments, the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, 12, 13 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the disclosure can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the disclosure can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the disclosure.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2.

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al., *Annu Rev Biophys Biomol Struct.* 35:225-49 (2006)). These unnatural amino acids can advantageously be used to chemically link molecules of interest to the AAV capsid protein.

Modified AAV Capsid Proteins and Virus Capsids and Virus Vectors Comprising the Same The present disclosure provides AAV capsid proteins (VP1, VP2 and/or VP3) comprising a modification (e.g., a substitution) in the amino acid sequence and virus capsids and virus vectors comprising the modified AAV capsid protein. The inventors have discovered that modifications of the AAV capsid proteins can confer one or more desirable properties to virus vectors comprising the modified AAV capsid protein including without limitation, the ability to evade neutralizing antibodies. Thus, the present disclosure addresses some of the limitations associated with conventional AAV vectors.

Accordingly, in one aspect, the present disclosure provides an adeno-associated virus (AAV) capsid protein, comprising one or more amino acid substitutions, wherein the one or more substitutions modify one or more antigenic sites on the AAV capsid protein. The modification of the one or more antigenic sites results in inhibition of binding by an antibody to the one or more antigenic sites and/or inhibition of neutralization of infectivity of a virus particle comprising said AAV capsid protein. The one or more amino acid substitutions can be in one or more antigenic footprints identified by peptide epitope mapping and/or cryo-electron microscopy studies of AAV-antibody complexes containing AAV capsid proteins.

The capsid proteins of this disclosure are modified to produce an AAV capsid that is present in an AAV virus particle or AAV virus vector that has a phenotype of evading neutralizing antibodies. The AAV virus particle or vector of this disclosure can also have a phenotype of enhanced or maintained transduction efficiency in addition to the phenotype of evading neutralizing antibodies. By "evading neutralizing antibodies," it is meant that antibodies that would bind to the original amino acid sequence on natural AAV particles will not recognize and thus will not bind the AAV particles described herein, particularly when the substituted residues do not match those of any natural AAV serotype.

Thus, in one embodiment, the present disclosure provides an adeno-associated virus (AAV) capsid protein, wherein the capsid protein comprises a substitution resulting in the amino acid sequence: $X^1$—$X^2$-T-F—N—$X^3$—$X^4$—K-L-$X^5$ (SEQ ID NO:197) at the amino acids corresponding to amino acid positions 661 to 670 of the native AAV8 capsid protein (VP1 numbering) based on the reference amino acid sequence of AAV8 identified as SEQ ID NO:8 and corresponding to amino acid positions 659 to 668 of the native AAV9 capsid protein (VP1 numbering) based on the reference amino acid sequence of AAV9 identified as SEQ ID NO:26 or at the equivalent amino acid positions in the capsid protein of any other AAV serotype, wherein $X^1$ is any amino acid other than P; wherein $X^2$ is any amino acid other than T; wherein $X^3$ is any amino acid other than Q; wherein $X^4$ is any amino acid other than S; and/or wherein $X^5$ is any amino acid other than N.

In some embodiments, $X^1$ can be V, I, Q, S, F, R, or W.

In some embodiments, $X^2$ can be G, S, L, V, C, D, R, I, or P.

In some embodiments, $X^3$ can be E, P, C, S, G, R, D, L, N, V or A.

In some embodiments, $X^4$ can be P, Q, G, R, D, C, A, M, H, or T.

In some embodiments, $X^5$ can be H, M, W, C, F, A, Q, G, P, S, K, W, or R.

In some embodiments, $X^1$ is P, $X^2$ is G, $X^3$ is G, $X^4$ is G, and $X^5$ is G. In some embodiments, $X^1$ is R, $X^2$ is S, $X^3$ is G, $X^4$ is D, and $X^5$ is N. In some embodiments, In some embodiments, $X^1$ is P, $X^2$ is T, $X^3$ is V, $X^4$ is D, and $X^5$ is G.

In some embodiments, the present disclosure provides an adeno-associated virus (AAV) capsid protein, wherein the capsid protein comprises a substitution resulting in the amino acid sequence: $X^1$—$X^2$-T-F—N—$X^3$—$X^4$ (SEQ ID NO:198) at the amino acids corresponding to amino acid positions 661 to 667 of the native AAV8 capsid protein (VP1 numbering) based on the reference amino acid sequence of AAV8 identified as SEQ ID NO:8 and corresponding to amino acid positions 659 to 665 of the native AAV9 capsid protein (VP1 numbering) based on the reference amino acid sequence of AAV9 identified as SEQ ID NO:26 or at the equivalent amino acid positions in the capsid protein of any other AAV serotype, wherein $X^1$ is any amino acid other than P; wherein $X^2$ is any amino acid other than T; wherein $X^3$ is any amino acid other than Q; and/or wherein $X^4$ is any amino acid other than S. In some embodiments, $X^1$ is R, $X^2$ is S, $X^3$ is G, and $X^4$ is D.

The substitutions at any of $X^1$, $X^2$, $X^3$, $X^4$ and/or $X^5$ can be in any combination of substituted sites and any combination of substitutions at the substituted sites. For example, a capsid may comprise amino acid substitutions at $X^1$, $X^2$ and $X^4$, and wildtype residues at $X^3$ and $X^5$.

In some embodiments, the present disclosure provides an adeno-associated virus (AAV) capsid protein, wherein the capsid protein comprises a substitution resulting in the amino acid sequence: VGTFNEAKLH (h1; SEQ ID NO:166), VSTFNPAKLM (h9; SEQ ID NO:167), PLTFNCCKLN (d5; SEQ ID NO:168), PVTFNQDKLW (d4; SEQ ID NO:169), PVTFNSGKLC (h6; SEQ ID NO:170), IGTFNGQKLC (h4; SEQ ID NO:171), QVTFNGGKLF (h5; SEQ ID NO:172), PGTFNGGKLW (h3; SEQ ID NO:173), PGTFNGGKLA (h8; SEQ ID NO:174), PGTFNRGKLQ (h7; SEQ ID NO:175), PGTFNDGKLG (d6; SEQ ID NO:176), PSTFNCMKLP (h2; SEQ ID NO:177), PSTFNCPKLQ (h11; SEQ ID NO:178), PSTFNLGKLS (d1; SEQ ID NO:179), PSTFNGGKLP (d7; SEQ ID NO:180), SCTFNLHKLC (h12; SEQ ID NO:181), QDTFNRTKLC (h10; SEQ ID NO:182), PTTFNRTKLM (d3; SEQ ID NO:183), FVTFNGDKLM (xx4; SEQ ID NO:184), RRTFNSRKLK (xx2; SEQ ID NO:185), SVTFNSAKLQ (e2; SEQ ID NO:186), VLTFNGSKLA (e1; SEQ ID NO:187), PTTFNPSKLW (xx3; SEQ ID NO:188), PVTFNEGKLF (e3; SEQ ID NO:189), PTTFNQGKLQ (e5; SEQ ID NO:190), PGTFNGGKLG (xx1; SEQ ID NO:191), PLTFNNGKLS (xx5; SEQ ID NO:192), RSTFNGDKLN (hi-C; SEQ ID NO:193), PTTFNVDKLG (hi-A; SEQ ID NO:194), PITFNEPKLA (hi-B; SEQ ID NO:195), or WPTFNAGKLR (hi-e; SEQ ID NO:196) at the amino acids corresponding to amino acid positions 661 to 670 of the native AAV8 capsid protein (VP1 numbering) based on the reference amino acid sequence of AAV8 identified as SEQ ID NO:8 and corresponding to amino acid positions 659 to 668 of the native AAV9 capsid protein (VP1 numbering) based on the reference amino acid sequence of AAV9 identified as SEQ ID NO:26 or at the equivalent amino acid positions in the capsid protein of any other AAV serotype Despite recent success in gene delivery with rAAV particles, pre-existing antibodies, able to neutralize incoming vectors, represent a significant challenge. To this end, the inventors generated a panel of neutralizing anti-AAV (e.g., anti-AAV8, or anti-AAV9) capsid antibodies. They used these antibodies to map the antigenic footprint of AAV so that capsid proteins with one or more amino acid substitutions within this antigenic map or footprint could be developed. An antigenic footprint is therefore a list of amino acid residues on a AAV capsid that interact with an anti-AAV antibody. Recombinant AAV (rAAV) particles comprising these modified capsid proteins would have decreased reactivity to neutralizing antibodies, and thus better transduction efficiency in the presence of neutralizing antibodies. For example, using cryo-electron microscopy (cryo-EM) and image reconstructions techniques, the inventors generated a footprint for an antibody deliberately selected to react with AAV8 and AAV9, HL2372. This antibody binds to the structurally conserved 5-fold region of the AAV capsid. blocking a channel that connects the capsid interior to the exterior. In some embodiments, this channel serves multiple functions during infection, including the externalization of a phospholipase A2 enzyme and elements required during trafficking to a cell nucleus and genome packaging during virion formation. In some embodiments, the neutralization mechanism involves inhibition of one of these steps.

Accordingly, provided herein are rAAV capsid proteins and rAAV particles comprising a modified 5-fold region. In some embodiments, a modified 5-fold region comprises one or more amino acid substitutions. In some embodiments, rAAV capsid proteins and rAAV particles comprising a modified 5-fold region have reduced or decreased reactivity to neutralizing antibodies, compared to capsid proteins and particles with an unmodified 5-fold region. Provided herein are also methods of making rAAV particles comprising a modified 5-fold region, and methods of using rAAV capsid proteins and rAAV particles comprising a modified 5-fold region to deliver one or more genes of interest to a cell, organ, tissue, or subject.

AAV Structure and the 5-Fold Region

The wild-type AAV genome is a single-stranded deoxyribonucleic acid (ssDNA), either positive- or negative-sensed. The genome comprises two inverted terminal repeats (ITRs), one at each end of the DNA strand, and two open reading frames (ORFs): rep and cap between the ITRs. The rep ORF comprises four overlapping genes encoding Rep proteins required for the AAV life cycle: Rep78, Rep68, Rep52 and Rep40. The cap ORF comprises overlapping genes encoding capsid proteins: VP1, VP2 and VP3, which interact together to form the viral capsid. VP1, VP2 and VP3 are translated from two alternatively spliced transcripts. The capsid forms a supramolecular assembly of 60 individual capsid protein subunits into a non-enveloped, T-1 icosahedral capsid capable of protecting the AAV genome. The assembled capsid is composed of VP1, VP2, and VP3 (molecular masses of approximately 87, 73, and 62 kDa respectively) in a ratio of about 1:1:10.

For most AAV serotypes, VP1 has 735 to 738 amino acids. AAV5 VP1 has 724 amino acids. For most serotypes (e.g., AAV1, AAV2, or AAV8), capsid protein VP2 is made up of amino acids 138-735 or 138-738 of VP1. In some serotypes, e.g., AAV5, capsid protein VP2 is made up of amino acids 137-724 of VP1. For most serotypes, capsid protein VP3 is made up of amino acids 203-735 of VP1.

The AAV capsid surface topology arises from loops that connect the core beta strands of each subunit, generating distinctive features including protruding spikes surrounding the 3-fold symmetry axis; a cylindrical protrusion surrounding the pore near the 5-fold symmetry axis (also referred to herein as the "5-fold region"), and a dimple near the 2-fold symmetry axis. Differences in the intervening loops of different AAV serotypes lead to unique capsid structural features, which contribute to serotype-specific receptor interactions, immune recognition, cell tropism, and transduction efficiency. Images of the 3-fold symmetry axis, 5-fold region, and 2-fold symmetry axis are shown in Lerch et al. (*Virology.* 2010 Jul. 20; 403(1): 26-36), and Govindasamy et al. (*J. Virol.*, 2013, 87(20): 11187-11199), each of which are incorporated herein by reference in their entirety, and also specifically for their depictions of the 5-fold region.

In some embodiments, the 5-fold region of a rAAV is a region which comprises the AAV DE-loop, the AAV HI-loop, the 2/5-fold wall, and surrounding surface residues. In some embodiments, a DE-loop comprises amino acids 323-335 (VP1 numbering) based on the reference amino acid sequence of AAV1 identified as SEQ ID NO:18. In some embodiments, a HI-loop comprises amino acids 659-668 (VP1 numbering) based on the reference amino acid sequence of AAV1 identified as SEQ ID NO:18. In some embodiments, a 2/5-fold wall comprises amino acids 258-277, 545-550, and 716-720 (VP1 numbering) based on the reference amino acid sequence of AAV1 identified as SEQ ID NO:18. In some embodiments, a DE-loop consists of amino acids 323-335 (VP1 numbering) based on the reference amino acid sequence of AAV1 identified as SEQ ID NO:18. In some embodiments, a HI-loop consists of amino acids 659-668 (VP1 numbering) based on the reference amino acid sequence of AAV1 identified as SEQ ID NO:18. In some embodiments, a 2/5-fold wall consists of amino acids 258-277, 545-550, and 716-720 (VP1 numbering) based on the reference amino acid sequence of AAV1 identified as SEQ ID NO:18. In some embodiments, a 5-fold region comprise amino acids outside of the DE-loop, the AAV HI-loop, and the 2/5-fold wall (e.g., 250-257, 365-375, or 550-557, 655-657; VP1 numbering) based on the reference amino acid sequence of AAV1 identified as SEQ ID NO:18. In some embodiments, the 5-fold region of a rAAV comprises the amino acid residues listed in the first column of Table 4.

Recombinant a AV Capsid Proteins Comprising a Modified 5-Fold Region

Provided herein is a rAAV capsid protein comprising a modified 5-fold region. The modifications may comprise, for example, substitutions, deletions, and/or insertions. In some embodiments, the modified 5-fold region comprises one or more amino acids substitutions (e.g., 1, 2, 3, 4, 5, 6, 7, 8, 9, 10 or more amino acid substitutions). In some embodiments, a modified 5-fold region comprises one or more amino acid substitutions in the DE-loop compared to the native sequence. In some embodiments, a modified 5-fold region comprises one or more amino acid substitutions in the HI-loop compared to the native sequence. In some embodiments, a modified 5-fold region comprises one or more amino acid substitutions in the 2/5-fold wall compared to the native sequence. In some embodiments, a modified 5-fold region comprises one or more amino acids substitutions in the DE-loop and HI-loop. In some embodiments, a modified 5-fold region comprises one or more amino acid substitutions in the DE-loop and the 2/5-fold wall. In some embodiments, a modified 5-fold region comprises one or more amino acid substitutions in the HI-loop and the 2/5-fold wall. In some embodiments, a modified 5-fold region comprises one or more amino acid substitutions in the DE-loop, HI-loop, and 2/5-fold wall.

In some embodiments, a rAAV capsid protein comprises a substitution resulting in one of the following amino acid sequences at the amino acids corresponding to amino acids 661-670 of the native AAV8 capsid protein: VGTFNEAKLH (h1; SEQ ID NO:166), VSTFNPAKLM (h9; SEQ ID NO:167), PLTFNCCKLN (d5; SEQ ID NO:168), PVTFNQDKLW (d4; SEQ ID NO:169), PVTFNSGKLC (h6; SEQ ID NO:170), IGTFNGQKLC (h4; SEQ ID NO:171), QVTFNGGKLF (h5; SEQ ID NO:172), PGTFNGGKLW (h3; SEQ ID NO:173), PGTFNGGKLA (h8; SEQ ID NO:174), PGTFNRGKLQ (h7; SEQ ID NO:175), PGTFNDGKLG (d6; SEQ ID NO:176), PSTFNCMKLP (h2; SEQ ID NO:177), PSTFNCPKLQ (h11; SEQ ID NO:178), PSTFNLGKLS (d1; SEQ ID NO:179), PSTFNGGKLP (d7; SEQ ID NO:180), SCTFNLHKLC (h12; SEQ ID NO:181), QDTFNRTKLC (h10; SEQ ID NO:182), PTTFNRTKLM (d3; SEQ ID NO:183), FVTFNGDKLM (xx4; SEQ ID NO:184), RRTFNSRKLK (xx2; SEQ ID NO:185), SVTFNSAKLQ (e2; SEQ ID NO:186), VLTFNGSKLA (e1; SEQ ID NO:187), PTTFNPSKLW (xx3; SEQ ID NO:188), PVTFNEGKLF (e3; SEQ ID NO:189), PTTFNQGKLQ (e5; SEQ ID NO:190), PGTFNGGKLG (xx1; SEQ ID NO:191), PLTFNNGKLS (xx5; SEQ ID NO:192), RSTFNGDKLN (hi-C; SEQ ID NO:193), PTTFNVDKLG (hi-A; SEQ ID NO:194), PITFNEPKLA (hi-B; SEQ ID NO:195), or WPTFNAGKLR (hi-e; SEQ ID NO:196). In some embodiments, an rAAV capsid protein comprises an amino acid substitution at one, two, three, four, or all five of amino acids corresponding to P661, T662, Q666, S667, and N670 of the native AAV8 sequence. In some embodiments, an rAAV capsid protein comprises a sequence that is at least 90%, 95%, 97%, 98% or 99% similar or identical to the native AAV8 capsid protein sequence and comprises an amino acid substitution at one of, two of, three of, four of, or all five amino acids corresponding to P661, T662, Q666, S667, and N670 of the native AAV8 sequence. In some embodiments, a recombinant AAV capsid protein comprises at least one of the following amino acid substitutions: P661V, P661I, P661Q, P661S, P661F, P661R, P661W, T662G, T662S, T662L, T662V, T662C, T662D, T662R, T662I, T662P, Q666E, Q666P, Q666C, Q666S, Q666G, Q666R, Q666D, Q666L, Q666N, Q666V, Q666A, S667P, S667Q, S667G, S667R, S667D, S667C, S667A, S667M, S667H, S667T, N670H, N670M, N670W, N670C, N670F, N670A, N670Q, N670G, N670P, N670S, N670K, N670W, or N670R (numbering based on the reference amino acid sequence of AAV8 identified as SEQ ID NO:8). In some embodiments, a recombinant AAV capsid protein comprises the following amino acid substitutions: P661R, P662S, P666G, and P667D.

In some embodiments, a recombinant AAV capsid protein comprises a substitution resulting one of the following amino acid sequences at the amino acids corresponding to amino acids 659-668 of the native AAV9 capsid protein: VGTFNEAKLH (h1; SEQ ID NO:166), VSTFNPAKLM (h9; SEQ ID NO:167), PLTFNCCKLN (d5; SEQ ID NO:168), PVTFNQDKLW (d4; SEQ ID NO:169), PVTFNSGKLC (h6; SEQ ID NO:170), IGTFNGQKLC (h4; SEQ ID NO:171), QVTFNGGKLF (h5; SEQ ID NO:172), PGTFNGGKLW (h3; SEQ ID NO:173), PGTFNGGKLA (h8; SEQ ID NO:174), PGTFNRGKLQ (h7; SEQ ID NO:175), PGTFNDGKLG (d6; SEQ ID NO:176), PSTFNCMKLP (h2; SEQ ID NO:177), PSTFNCPKLQ (h11; SEQ ID NO:178), PSTFNLGKLS (d1; SEQ ID NO:179), PSTFNGGKLP (d7; SEQ ID NO:180), SCTFNLHKLC (h12; SEQ ID NO:181), QDTFNRTKLC (h10; SEQ ID NO:182), PTTFNRTKLM (d3; SEQ ID NO:183), FVTFNGDKLM (xx4; SEQ ID NO:184), RRTFNSRKLK (xx2; SEQ ID NO:185), SVTFNSAKLQ (e2; SEQ ID NO:186), VLTFNGSKLA (e1; SEQ ID NO:187), PTTFNPSKLW (xx3; SEQ ID NO:188), PVTFNEGKLF (e3; SEQ ID NO:189), PTTFNQGKLQ (e5; SEQ ID NO:190), PGTFNGGKLG (xx1; SEQ ID NO:191), PLTFNNGKLS (xx5; SEQ ID NO:192), RSTFNGDKLN (hi-C; SEQ ID NO:193), PTTFNVDKLG (hi-A; SEQ ID NO:194), PITFNEPKLA (hi-B; SEQ ID NO:195), or WPTFNAGKLR (hi-e; SEQ ID NO:196). In some embodiments, an rAAV capsid protein comprises an amino acid substitution at one, two, three, four, or all five of amino acids corresponding to P659, T660, A661, K664, and N668 of the native AAV9 sequence. In some embodiments, an rAAV capsid protein comprises a sequence that is at least 90%, 95%, 97%, 98% or 99% similar or identical to the native AAV9 capsid protein sequence and comprises an amino acid substitution at one of, two of, three of, four of, or all five amino acids corresponding to P659, T660, A661, K664, and N668 of the native AAV9 sequence. In some embodiments, a recombinant AAV capsid protein comprises one or more of the following amino acid substitutions: P659R, T660S, A661T, and/or K664G. In some embodiments, a recombinant AAV capsid protein comprises the following amino acid substitutions: P659R, T660S, A661T, and K664G.

In some embodiments, a modified 5-fold region comprises one or more amino acids substitutions in any of the positions within an antigenic footprint. In some embodiments, an antigenic footprint is one of the antigenic footprints listed in Table 5. For example, one or more amino acid substitutions in a modified 5-fold region may be within the antigenic footprint for AVB in amino acid positions (e.g., 250-258, 324-333, 371, 372, 546-550, 557, 655-674, and 716-721; 250-258 323-332, 370, 371 545-548, 556 655-673, and 715-720; or 240-248, 314-323, 372, 373, 532-535, 546, 644-662, and 704-709). In some embodiments, one or more amino acid substitutions in a modified 5-fold region may be within the antigenic footprint for Capture Select Affinity Ligand for AAV9 (CSAL9) in amino acid positions (e.g., 251-255, 264, 325-334, and 656-674). In some embodiments, one or more amino acid substitutions in a modified 5-fold region may be within the antigenic footprint for HL2372 in amino acid positions (e.g., 252-266, 326-335, 658-676, and 720; or 251-266, 325-334, 657-673, and 718). In some embodiments, one or more amino acid substitutions in a modified 5-fold region may be within the antigenic footprint for ADK5a in amino acid positions (e.g., 218, 240-258, 261, 263, 267, 279, 331, 350, 355-360, 364, 365, 377, 378, 395, 429-432, 437, 450, 451, 453-456, 458, 459, 530-543, 545-548, 639, 641, 642, 648-651, 653-658, 660-662, 697-700, 704-712). In some embodiments, one or more amino acid substitutions in a modified 5-fold region may be within the antigenic footprint for ADK5b in amino acid positions (e.g., 241-248, 313-319, 321, 323, 355, 356, 358-362, 440-443, 446-449, 530-548, 645-651, 653-661, 697, 698, and 704-712).

In some embodiments, a modified 5-fold region comprises one or more amino acids substitutions in any of the positions within any of the amino acid positions listed in Table 5. In some embodiments, there are more than one amino acid substitutions within a single footprint. In some embodiments, there are more than one amino acid substitutions wherein the more than one amino acid substitutions lie within different antigenic footprints. For example, a modified 5-fold region may have one or more amino acid substitutions in a footprint for ADK5a and one or more amino acid substitutions in a footprint for ADK5b. In some embodiments, a modified 5-fold region comprises one or more amino acid substitutions within the ranges of amino acids shown in Table 5 and/or one or more amino acid substitutions up to 10 amino acids on either or both sides of these ranges (e.g., 1, 2, 3, 4, 5, 6, 7, 8, 9, or 10 amino acids on either or both sides of these ranges).

In some embodiments, a modified 5-fold region comprises amino acid positions 328-333, 658-663, 671, 719-721, and up to 10 amino acids on either or both sides of these ranges (e.g., 1, 2, 3, 4, 5, 6, 7, 8, 9, or 10 amino acids on either or both sides of these ranges).

In some embodiments, a modified 5-fold region comprises one or more amino acids substitutions in any of the positions listed in the first column of Table 4. In some embodiments, a modified 5-fold region comprises one or more amino acids substitutions in any of the positions listed as being shared by other AAV serotypes and antibodies of Table 4 (i.e., marked as "x"). In some embodiments, a modified 5-fold region comprises one or more amino acid substitutions in any of the positions listed as being unique for a particular serotype in Table 4 (i.e., not marked as "x").

In some embodiments, the residues within the 5-fold antigenic region or epitope do not overlap with antibody epitopes for antibodies that bind the 3-fold axes, or the 2-/5-fold wall regions of the AAV capsid.

In some embodiments, a modified 5-fold region comprises one or more amino acid substitutions within footprints that are specific to particular neutralizing antibodies (e.g., AVB, CSAL9, HL2372, ADK5a, or ADK5b). In some embodiments, neutralizing antibodies are specific to or specifically recognize AAV particles or capsids of particular serotypes. For example, HL2372 recognizes AAV8 and AAV9 (see FIG. 3), ADK5a and ADK5b recognize AAV5, CSAL9 recognizes AAV9, AVB recognizes AAV1, AAV2, AAV5, and AAV8, and so on. Specific recognition means that an antibody recognizes an AAV particle of a particular serotype to a greater degree (e.g., 1.5-fold, 2-fold, 3-fold, 4-fold, 5-fold, 2-5-fold, 5-10-fold, or 10 fold or greater) than AAV particles of other serotypes.

Amino Acid Substitutions

In some embodiments, an amino acid substitution in a modified 5-fold region comprises substitution of a charged amino acid (e.g., D, E, K, R, or H) with an uncharged or polar amino acid (e.g., A, N, C, Q, G, I, L, M, F, P, S, T, W, Y, or V). In some embodiments, an amino acid substitution in a modified 5-fold region comprises substitution of an uncharged or polar amino acid (e.g., A, N, C, Q, G, I, L, M, F, P, S, T, W, Y, V) with a charged amino acid (e.g., D, E, K, R, or H).

In some embodiments, an amino acid substitution in a modified 5-fold region comprises substitution of a negatively charged amino acid (e.g., D, or E) with a positively charged amino acid (e.g., K, R, or H). In some embodiments, an amino acid substitution in a modified 5-fold region comprises substitution of a positively charged amino acid (e.g., K, R, or H) with a negatively charged amino acid (e.g., D, or E).

In some embodiments, an amino acid substitution in a modified 5-fold region comprises substitution of a polar amino acid (e.g., D, E, H, K, R, N, Q, S, T, or Y) with a non-polar amino acid (e.g., A, C, G, I, L, M, F, P, V, or W). In some embodiments, an amino acid substitution in a modified 5-fold region comprises substitution of a non-polar amino acid (e.g., A, C, G, I, L, M, F, P, V, or W) with a polar amino acid (e.g., D, E, H, K, R, N, Q, S, T, or Y).

In some embodiments, an amino acid substitution in a modified 5-fold region comprises substitution of an acidic amino acid (e.g., D, or E) with a basic amino acid (e.g., H, K, or R). In some embodiments, an amino acid substitution in a modified 5-fold region comprises substitution of a basic amino acid (e.g., H, K, or R) with an acidic amino acid (e.g., D, or E).

In some embodiments, an amino acid substitution comprises substitution with an amino acid in a capsid protein of another AAV serotype at an equivalent position. For example, the amino acid E718 in AAV9 can be substituted with an N, like in AAV2 at an equivalent position.

The present disclosure also provides an AAV capsid comprising the AAV capsid protein of this disclosure. Further provided herein is a viral vector comprising the AAV capsid of this disclosure as well as a composition comprising the AAV capsid protein, AAV capsid and/or viral vector of this disclosure in a pharmaceutically acceptable carrier.

In some embodiments, the virus vector of this disclosure is immunologically distinct from its parental AAV serotype and is not recognized by antibodies (e.g., neutralizing antibodies) that bind the parental serotype.

The present disclosure additionally provides a method of introducing a nucleic acid into a cell in the presence of antibodies against the AAV capsid, comprising contacting the cell with the viral vector of this disclosure. The cell can be in a subject and in some embodiments, the subject can be a human subject.

In particular embodiments, the modified virus capsid proteins of the disclosure are not limited to AAV capsid proteins in which amino acids from one AAV capsid protein are substituted into another AAV capsid protein, and the substituted and/or inserted amino acids can be from any source, and can further be naturally occurring or partially or completely synthetic.

As described herein, the nucleic acid and amino acid sequences of the capsid proteins from a number of AAV are known in the art. Thus, the amino acids "corresponding" to amino acid positions of the native AAV capsid protein can be readily determined for any other AAV (e.g., by using sequence alignments).

It is contemplated that the modified capsid proteins of the disclosure can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10 or AAV11 capsid protein or any of the AAV shown in Table 1) but is not so limited. Those skilled in the art will understand that a variety of manipulations to the AAV capsid proteins are known in the art and the disclosure is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). Such AAV capsid proteins are also within the scope of the present disclosure.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 1, etc.), it is intended to encompass the native capsid protein as well as capsid proteins that have alterations other than the modifications of the disclosure. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present disclosure) as compared with the native AAV capsid protein sequence. In embodiments of the disclosure, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present disclosure) as compared with the native AAV capsid protein sequence. In embodiments, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids (other than the amino acid deletions of the disclosure) as compared with the native AAV capsid protein sequence.

Thus, for example, the term "AAV2 capsid protein" includes AAV capsid proteins having the native AAV2 capsid protein sequence (see GenBank Accession No. AAC03780) as well as those comprising substitutions, insertions and/or deletions (as described in the preceding paragraph) in the native AAV2 capsid protein sequence.

In particular embodiments, the AAV capsid protein has the native AAV capsid protein sequence or has an amino acid sequence that is at least about 90%, 95%, 97%, 98% or 99% similar or identical to a native AAV capsid protein sequence. For example, in particular embodiments, an "AAV2" capsid protein encompasses the native AAV2 capsid protein sequence as well as sequences that are at least about 90%, 95%, 97%, 98% or 99% similar or identical to the native AAV2 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci.* USA 85,2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996). WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

Also provided is a virus capsid comprising, consisting essentially of, or consisting of the modified AAV capsid protein of the disclosure. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV capsid, avian AAV capsid or any other AAV now known or later identified. A nonlimiting list of AAV serotypes is shown in Table 1 an AAV capsid of this disclosure can be any AAV serotype listed in Table 1 or derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the disclosure the therapeutically useful molecule is covalently linked (i.e., conjugated or chemically coupled) to the capsid proteins. Methods of covalently linking molecules are known by those skilled in the art.

The modified virus capsids of the disclosure also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present disclosure. Further, the disclosure provides compositions and pharmaceutical formulations comprising the inventive modified virus capsids; optionally, the composition also comprises a modified virus vector of the disclosure.

Also provided are nucleic acids (optionally, isolated nucleic acids) encoding the modified virus capsids and capsid proteins of the disclosure. Further provided are vectors comprising the nucleic acids, and cells (in vivo or in culture) comprising the nucleic acids and/or vectors of the disclosure. As one example, the present disclosure provides a virus vector comprising: (a) a modified AAV capsid of this disclosure; and (b) a nucleic acid comprising at least one terminal repeat sequence, wherein the nucleic acid is encapsidated by the AAV capsid.

Other suitable vectors include without limitation viral vectors (e.g., adenovirus, AAV, herpesvirus, vaccinia, pox-viruses, baculoviruses, and the like), plasmids, phage, YACs, BACs, and the like. Such nucleic acids, vectors and cells can be used, for example, as reagents (e.g., helper packaging constructs or packaging cells) for the production of modified virus capsids or virus vectors as described herein.

Virus capsids according to the disclosure can be produced using any method known in the art, e.g., by expression from a baculovirus (Brown et al., (1994) *Virology* 198:477-488).

The modifications to the AAV capsid protein according to the present disclosure are "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 20, 18, 15, 12, 10, 9, 8, 7, 6, 5, 4 or 3 contiguous amino acids.

The modified capsid proteins and capsids of the disclosure can further comprise any other modification, now known or later identified.

For example, the AAV capsid proteins and virus capsids of the disclosure can be chimeric in that they can comprise all or a portion of a capsid subunit from another virus, optionally another parvovirus or AAV, e.g., as described in international patent publication WO 00/28004.

In some embodiments, the virus capsid can be a targeted virus capsid, comprising a targeting sequence (e.g., substituted or inserted in the viral capsid) that directs the virus capsid to interact with cell-surface molecules present on desired target tissue(s) (see, e.g., international patent publication WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

For example, a virus capsid of this disclosure may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., *Annu Rev Biophys Biomol Struct.* 35:225-49 (2006)) can be incorporated into an AAV capsid subunit of this disclosure at an orthogonal site as a means of redirecting a low-transduction vector to desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques,* 1$^{st}$ edition, Academic Press, 1996).

In some embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor (Brown et al., (1993) *Science* 262:114). The structure of B19 has been determined to 8 Å resolution (Agbandje-McKenna et al., (1994) *Virology* 203:106). The region of the B19 capsid that binds to globoside has been mapped between amino acids 399-406 (Chapman et al., (1993) *Virology* 194:419), a looped out region between β-barrel structures E and F (Chipman et al., (1996) *Proc. Nat. Acad. Sci. USA* 93:7502). Accordingly, the globoside receptor binding domain of the B19 capsid may be substituted into an AAV capsid protein of this disclosure to target a virus capsid or virus vector comprising the same to erythroid cells.

In some embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, ρ or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP (SEQ ID NO:31) peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV capsid that otherwise does not bind to HS or heparin). It is known in the art that HS/heparin binding is mediated by a "basic patch" that is rich in arginines and/or lysines. In exemplary embodiments, a sequence following the motif BXXB (SEQ ID NO:32), where "B" is a basic residue and X is neutral and/or hydrophobic can be employed. As a nonlimiting example, BXXB can be RGNR (SEQ ID NO:33). As another nonlimiting example, BXXB is substituted for amino acid positions 262 through 265 in the native AAV2 capsid protein or at the corresponding position(s) in the capsid protein of another AAV serotype.

Other nonlimiting examples of suitable targeting sequences include the peptides targeting coronary artery endothelial cells identified by Müller et al., *Nature Biotechnology* 21:1040-1046 (2003) (consensus sequences NSVRDL(G/S) (SEQ ID NO:34), PRSVTVP (SEQ ID NO:35), NSVSSX(S/A) (SEQ ID NO:36); tumor-targeting peptides as described by Grifman et al., *Molecular Therapy* 3:964-975 (2001) (e.g., NGR, NGRAHA (SEQ ID NO:37)); lung or brain targeting sequences as described by Work et al., *Molecular Therapy* 13:683-693 (2006) (QPEHSST [SEQ ID NO:38], VNTANST [SEQ ID NO:39], HGPMQKS [SEQ ID NO:40], PHKPPLA [SEQ ID NO:41], IKNNEMW [SEQ ID NO:42], RNLDTPM [SEQ ID NO:43], VDSHRQS [SEQ ID NO:44], YDSKTKT [SEQ ID NO:45], SQLPHQK [SEQ ID NO:46], STMQQNT [SEQ ID NO:47], TERYMTQ [SEQ ID NO:48], QPEHSST [SEQ ID NO:49], DASLSTS [SEQ ID NO:50], DLPNKKT [SEQ ID NO:51], DLTAARL [SEQ ID NO:52], EPHQFNY [SEQ ID NO:53], EPQSNHT [SEQ ID NO:54], MSSWPSQ [SEQ ID NO:55], NPKHNAT [SEQ ID NO:56], PDGMRTT [SEQ ID NO:57], PNNNKTT [SEQ ID NO:58], QSTTHDS [SEQ ID NO:59], TGSKQKQ [SEQ ID NO:60], SLKHQAL [SEQ ID NO:61] and SPIDGEQ [SEQ ID NO:62]); vascular targeting sequences described by Hajitou et al., *TCM* 16:80-88 (2006) (WIFPWIQL [SEQ ID NO:63], CDCRGDCFC [SEQ ID NO:64], CNGRC [SEQ ID NO:65], CPRECES [SEQ ID NO:66], GSL, CTTHWGFTLC [SEQ ID NO:67], CGRRAGGSC [SEQ ID NO:68], CKGGRAKDC [SEQ ID NO:69], and CVPELGHEC [SEQ ID NO:70]); targeting peptides as described by Koivunen et al., *J. Nucl. Med.* 40:883-888 (1999) (CRRETAWAK [SEQ ID NO:71], KGD, VSWFSHRYSPFAVS [SEQ ID NO:72], GYRDGYAGPILYN [SEQ ID NO:73], XXXY*XXX [SEQ ID NO:74; where Y* is phospho-Tyr], Y*E/MNW [SEQ ID NO:75], RPLPPLP [SEQ ID NO:76], APPLPPR [SEQ ID NO:77], DVFYPYPYASGS [SEQ ID NO:78], MYWYPY [SEQ ID NO:79], DITWDQLWDLMK [SEQ ID NO:80], CWDD(G/L)WLC [SEQ ID NO:81], EWCEYLGGYLRCYA [SEQ ID NO:82], YXCXXGPXTWXCXP [SEQ ID NO:83], IEGPTLRQWLAARA [SEQ ID NO:84], LWXX(Y/W/F/H) [SEQ ID NO:85], XFXXYLW [SEQ ID NO:86], SSIISHFRWGLCD [SEQ ID NO:87], MSRPACPPNDKYE [SEQ ID NO:88], CLRSGRGC [SEQ ID NO:89], CHWMFSPWC [SEQ ID NO:90], WXXF [SEQ ID NO:91], CSSRLDAC [SEQ ID NO:92], CLPVASC [SEQ ID NO:93], CGFECVRQCPERC [SEQ ID NO:94], CVALCREACGEGC [SEQ ID NO:95], SWCEPGWCR [SEQ ID NO:96], YSGKWGW [SEQ ID NO:97], GLSGGRS [SEQ ID NO:98], LMLPRAD [SEQ ID NO:99], CSCFRDVCC [SEQ ID NO:100], CRDVVSVIC [SEQ ID NO:101], CNGRC [SEQ ID NO:102], and GSL); and tumor targeting peptides as described by Newton & Deutscher, Phage Peptide Display in Handbook of Experimental Pharmacology, pages 145-163, Springer-Verlag, Berlin (2008) (MARSGL [SEQ ID NO:103], MARAKE [SEQ ID NO:104], MSRTMS [SEQ ID NO:105], KCCYSL [SEQ ID NO:106], WRR, WKR, WVR, WVK, WIK, WTR, WVL, WLL, WRT, WRG, WVS, WVA, MYWGDSHWLQYWYE [SEQ ID NO:107], MQLPLAT [SEQ ID NO:108], EWLS [SEQ ID NO:109], SNEW [SEQ ID NO:110], TNYL [SEQ ID NO:111], WIFPWIQL [SEQ ID NO:112], WDLAWMFRLPVG [SEQ ID NO:113], CTVALPGGYVRVC [SEQ ID NO:114], CVPELGHEC [SEQ ID NO:115], CGRRAGGSC [SEQ ID NO:116], CVAYCIEHHCWTC [SEQ ID NO:117], CVFAHNYDYLVC [SEQ ID NO:118], CVFTSNYAFC [SEQ ID NO:119], VHSPNKK [SEQ ID NO:120], CDCRGDCFC [SEQ ID NO:121], CRGDGWC [SEQ ID NO:122], XRGCDX [SEQ ID NO:123], PXX(S/T) [SEQ ID NO:124], CTTHWGFTLC [SEQ ID NO:125], SGKGPRQITAL [SEQ ID NO:126], A(A/Q)(N/A)(L/Y)(T/V/M/R)(R/K) [SEQ ID NO:127], VYMSPF [SEQ ID NO:128], MQLPLAT [SEQ ID NO:129], ATWLPPR [SEQ ID NO:130], HTMYYHHYQHHL [SEQ ID NO:131], SEVGCRAGPLQWLCEKYFG [SEQ ID NO:132], CGLLPVGRPDRNVWRWLC [SEQ ID NO:133], CKGQCDRFKGLPWEC [SEQ ID NO:134], SGRSA [SEQ ID NO:135], WGFP [SEQ ID NO:136], LWXXAr [Ar=Y, W, F, H) [SEQ ID NO:85], XFXXYLW [SEQ ID NO:137], AEPMPHSLNFSQYLWYT [SEQ ID NO:138], WAY(W/F)SP [SEQ ID NO:139], IELLQAR [SEQ ID NO:140], DITWDQLWDLMK [SEQ ID NO:141], AYTKCSRQWRTCMTTH [SEQ ID NO:142], PQNSKIPGPTFLDPH [SEQ ID NO:143], SMEPALPDWWWKMFK [SEQ ID NO:144], ANTPCGPYTHDCPVKR [SEQ ID NO:145], TACHQHVRMVRP [SEQ ID NO:146], VPWMEPAYQRFL [SEQ ID NO:147], DPRATPGS [SEQ ID NO:148], FRPNRAQDYNTN [SEQ ID NO:149], CTKNSYLMC [SEQ ID NO:150], C(R/Q)L/RT(G/N)XXG(A/V)GC [SEQ ID NO:151], CPIEDRPMC [SEQ ID NO:152], HEWSYLAPYPWF [SEQ ID NO:153], MCPKHPLGC [SEQ ID NO:154], RMWPSSTVNLSAGRR [SEQ ID NO:155], SAKTAVSQRVWLPSHRGGEP [SEQ ID NO:156], KSREHVNNSACPSKRITAAL [SEQ ID NO:157], EGFR [SEQ ID NO:158], RVS, AGS, AGLGVR [SEQ ID NO:159], GGR, GGL, GSV, GVS, GTRQGHTMRLGVSDG [SEQ ID NO:160], IAGLATPGWSHWLAL [SEQ ID NO:161], SMSIARL [SEQ ID NO:162], HTFEPGV [SEQ ID NO:163], NTSLKRISNKRIRRK [SEQ ID NO:164], LRIKRKRRKRKKTRK [SEQ ID NO:165], GGG, GFS, LWS, EGG, LLV, LSP, LBS, AGG, GRR, GGH and GTV).

As yet a further embodiment, the targeting sequence may be a peptide that can be used for chemical coupling (e.g., can comprise arginine and/or lysine residues that can be chemically coupled through their R groups) to another molecule that targets entry into a cell.

As another embodiment, the AAV capsid protein or virus capsid of the disclosure can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV serotype.

Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.).

Furthermore, in representative embodiments, the capsid protein, virus capsid or vector of this disclosure can comprise amino acid modifications such as described in PCT Publication No. WO 2010/093784 (e.g., 2i8) and/or in PCT Publication No. WO 2014/144229 (e.g., dual glycan).

In some embodiments, a capsid protein, virus capsid or vector of this disclosure can have equivalent or enhanced transduction efficiency relative to the transduction efficiency of the AAV serotype from which the capsid protein, virus capsid or vector of this disclosure originated. In some embodiments, a capsid protein, virus capsid or vector of this disclosure can have reduced transduction efficiency relative to the transduction efficiency of the AAV serotype from which the capsid protein, virus capsid or vector of this disclosure originated. In some embodiments, the capsid protein, virus capsid or vector of this disclosure can have equivalent or enhanced tropism relative to the tropism of the AAV serotype from which the capsid protein, virus capsid or vector of this disclosure originated. In some embodiments, the capsid protein, virus capsid or vector of this disclosure can have an altered or different tropism relative to the tropism of the AAV serotype from which the capsid protein, virus capsid or vector of this disclosure originated.

In some embodiments, the capsid protein, virus capsid or vector of this disclosure can have or be engineered to have tropism for brain tissue.

The foregoing embodiments can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2 (see, e.g., Table 6). As discussed elsewhere herein, the corresponding amino acid position(s) will be readily apparent to those skilled in the art using well-known techniques.

Nonlimiting examples of corresponding positions in a number of other AAV are shown in Table 6 (Position 2). In particular embodiments, the amino acid insertion or substitution is a threonine, aspartic acid, glutamic acid or phenylalanine (excepting AAV that have a threonine, glutamic acid or phenylalanine, respectively, at this position).

In other representative embodiments, the modified capsid proteins or virus capsids of the disclosure further comprise one or more mutations as described in WO 2007/089632 (e.g., an E→K mutation at amino acid position 531 of the AAV2 capsid protein or the corresponding position of the capsid protein from another AAV).

In further embodiments, the modified capsid protein or capsid can comprise a mutation as described in WO 2009/108274.

As another, possibility, the AAV capsid protein can comprise a mutation as described by Zhong et al. (*Virology* 381: 194-202 (2008); *Proc. Nat. Acad. Sci.* 105: 7827-32 (2008)). For example, the AAV capsid protein can comprise a Y→F mutation at amino acid position 730.

The modifications described above can be incorporated into the capsid proteins or capsids of the disclosure in combination with each other and/or with any other modification now known or later discovered.

The disclosure also encompasses virus vectors comprising the modified capsid proteins and capsids of the disclosure. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AAV capsid comprising a modified capsid subunit of the disclosure and a vector genome.

For example, in representative embodiments, the virus vector comprises: (a) a modified virus capsid (e.g., a modified AAV capsid) comprising a modified capsid protein of the disclosure; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In particular embodiments, the virus vectors of the disclosure (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), and/or (v) reduced transduction of brain tissues (e.g., neurons) as compared with the level of transduction by a virus vector without the modified capsid protein. In particular embodiments, the virus vector has systemic transduction toward muscle, e.g., transduces multiple skeletal muscle groups throughout the body and optionally transduces cardiac muscle and/or diaphragm muscle.

Recombinant AAV (rAAV) virus vectors, i.e., particles, as disclosed herein may comprise a viral capsid and a nucleic acid vector, which is encapsidated by the viral capsid. In some embodiments, rAAV may be an empty capsid and does not comprise any transgenes (e.g., a virus-like particle, VLP). As referred to herein, a capsid is the outer protein coat of AAV. A capsid may be empty or comprise a nucleic acid vector. In some embodiments, rAAV may be self-complementary (scAAV). In some embodiments, rAAV may be chimeric (e.g., containing a capsid protein comprising amino acids of different serotypes, or a rep gene comprising base pairs of different serotypes). In some embodiments, a rAAV is pseudotyped (e.g., comprising a capsid protein of one serotype and a rep gene of another serotype).

Recombinant AAV particles may comprise a nucleic acid vector, which may comprise at a minimum: (a) one or more heterologous nucleic acid regions comprising a sequence encoding a protein or polypeptide of interest or an RNA of interest (e.g., a siRNA or microRNA), and (b) one or more regions comprising inverted terminal repeat (ITR) sequences (e.g., wild-type ITR sequences or engineered ITR sequences) flanking the one or more nucleic acid regions (e.g., heterologous nucleic acid regions). Herein, heterologous nucleic acid regions comprising a sequence encoding a protein of interest or RNA of interest are referred to as genes of interest.

In some embodiments, a gene of interest encodes a detectable molecule. In some embodiments, a detectable molecule is a fluorescent protein, a bioluminescent protein, or a protein that provides color (e.g., β-galactosidase, β-lactamases, β-glucuronidase, or spheriodenone). In some embodiments, a detectable molecule is a fluorescent, bioluminescent, or enzymatic protein or functional peptide or functional polypeptide thereof. In some embodiments, a gene of interest encodes a therapeutic protein or therapeutic RNA. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA, or other nucleic acid or protein for gene editing.

In some embodiments, the nucleic acid vector comprised in a rAAV is between 4 kb and 5.2 kb in size (e.g., 4.2 to 5.2 kb in size). Any nucleic acid vector described herein may be encapsidated by a viral capsid, such as an AAV8 or AAV9 capsid or any other serotype, which may comprise a chimeric capsid protein as described herein. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

As mentioned above, in some embodiments, the nucleic acid vector comprises (1) one or more heterologous nucleic acid regions comprising a sequence encoding an RNA, protein or polypeptide of interest, (2) one or more nucleic acid regions comprising a sequence that facilitates expression of the heterologous nucleic acid region (e.g., a promoter), and (3) one or more nucleic acid regions comprising a sequence that facilitate integration of the heterologous nucleic acid region (optionally with the one or more nucleic acid regions comprising a sequence that facilitates expression) into the genome of the subject. In some embodiments, viral sequences that facilitate integration comprise Inverted Terminal Repeat (ITR) sequences. In some embodiments, the nucleic acid vector comprises one or more heterologous nucleic acid regions comprising a sequence encoding an RNA, protein or polypeptide of interest operably linked to a control element (e.g., a promoter), wherein the one or more heterologous nucleic acid regions are flanked on each side with an ITR sequence. Such a nucleic acid vector is herein also referred to as AAV-ITR containing one or more genes of interest. The ITR sequences can be derived from any AAV serotype (e.g., serotype 1, 2, 3, 4, 5, 6, 7, 8, 9, 10, 11, 12, or 13) or can be derived from more than one serotype.

ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, CA; and Addgene, Cambridge, MA; and "Gene delivery to skeletal muscle results in sustained expression and systemic delivery of a therapeutic protein" Kessler et al. *Proc Natl Acad Sci USA*. 1996 Nov. 26; 93(24):14082-7; and Machida. *Methods in Molecular Medicine. Viral Vectors for Gene Therapy Methods and Protocols*. 10.1385/1-59259-304-6:201 © Humana Press Inc. 2003. Chapter 10. "Targeted Integration by Adeno-Associated Virus" Weitzman et al. U.S. Pat. Nos. 5,139,941 and 5,962,313, all of which are incorporated herein by reference).

A capsid of a rAAV particle may comprise capsid proteins VP1, VP2, and VP3. In some embodiments, a capsid comprises only two capsid proteins.

In some embodiments, the nucleic acid vector comprises one or more regions comprising a sequence that facilitates expression of the nucleic acid (e.g., the heterologous nucleic acid), e.g., expression control sequences operatively linked to the nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

To achieve appropriate expression levels of the protein or polypeptide of interest, any of a number of promoters suitable for use in the selected host cell may be employed. The promoter may be, for example, a constitutive promoter, a tissue-specific promoter, an inducible promoter, or a synthetic promoter. For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter (e.g. chicken β-actin promoter) and human elongation factor-1α (EF-1α) promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include airway epithelial cell-specific promoters.

Synthetic promoters are also contemplated herein. A synthetic promoter may comprise, for example, regions of known promoters, regulatory elements, transcription factor binding sites, enhancer elements, repressor elements, and the like.

Recombinant AAV particles may be of any AAV serotype, including any derivative or pseudotype (e.g., 1, 2, 3, 4, 5, 6, 7, 8, 9, 10, 11, 12, 13, 2/1, 2/5, 2/8, 2/9, 3/1, 3/5, 3/8, or 3/9). Pseudotyping refers to using the capsid of one serotype and the genome of another serotype, or the mixing of a capsid and genome from different viral serotypes. These serotypes are denoted using a slash, so that AAV2/5 indicates a virus containing the genome of serotype 2 packaged in the capsid from serotype 5.

As used herein, the serotype of an rAAV particle refers to the serotype of the capsid proteins of the recombinant virus. Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, AAVrh.39, AAVrh.43, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y->F), AAV8 (Y733F), AAV2.15, AAV2.4, AAVrh3.45, and those listed in Table 1.

Genbank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety for the purpose of incorporating Genbank reference numbers, as well as for any other purpose.

Non-limiting examples of wild-type VP1 capsid protein sequences are provided herein as SEQ ID NOs:1-30. Examples of DE-loop residues are shown as underlined amino acids. Examples of HI-loop residues are shown in uppercase italics. Examples of 2/5-fold wall residues are shown in bold.

It will be understood by those skilled in the art that the modified capsid proteins, virus capsids and virus vectors of the disclosure exclude those capsid proteins, capsids and virus vectors that have the indicated amino acids at the specified positions in their native state (i.e., are not mutants).

Methods of Producing Virus Vectors

In one embodiment, the present disclosure provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the disclosure). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158: 67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377.

As a further alternative, the virus vectors described herein can be produced in insect cells using baculovirus vectors to deliver the rep/cap genes and rAAV template as described, for example, by Urabe et al., (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Methods of making or packaging rAAV are known in the art and reagents are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP2 region as described herein), and transfected into a recombinant cells such that the rAAV can be packaged and subsequently purified.

In some embodiments, the packaging is performed in a helper cell or producer cell, such as a mammalian cell or an insect cell. Exemplary mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC® CRL-1711™). The helper cell may comprise rep and/or cap genes that encode the Rep protein and/or Cap proteins for use in a method described herein. In some embodiments, the packaging is performed in vitro.

In some embodiments, a plasmid containing comprising the gene of interest is combined with one or more helper plasmids, e.g., that contain a rep gene of a first serotype and a cap gene of the same serotype or a different serotype, and transfected into helper cells such that the rAAV is packaged.

In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the cap gene is modified such that one or more of the proteins VP1, VP2 and VP3 do not get expressed. In some embodiments, the cap gene is modified such that VP2 does not get expressed. Methods for making such modifications are known in the art (Lux et al. (2005), *J Virology*, 79: 11776-87)

Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081.; Grimm et al. (2003), Helper Virus-Free, Optically Controllable, and Two-Plasmid-Based Production of Adeno-associated Virus Vectors of Serotypes 1 to 6, *Molecular Therapy*, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adeno-associated viral vector reference standards, *Molecular Therapy*, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), *J Virology*, 6:3096-3101).

AAV derivatives/pseudotypes, and methods of producing such derivatives/pseudotypes are known in the art (see, e.g., Asokan et al. *Mol Ther.* 2012 April; 20(4):699-708. doi: 10.1038/mt.2011.287. Epub 2012 Jan. 24. "The AAV vector toolkit: poised at the clinical crossroads"). Methods for producing and using pseudotyped rAAV vectors are known in the art (see, e.g., Duan et al., *J. Virol.*, 75:7662-7671, 2001; Halbert et al., J. Virol., 74:1524-1532, 2000; Zolotukhin et al., *Methods*, 28:158-167, 2002; and Auricchio et al., *Hum. Molec. Genet.*, 10:3075-3081, 2001).

An exemplary, non-limiting, rAAV production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV production. The rAAV can then be purified using any method known in the art or described herein, e.g., by iodixanol step gradient, CsCl gradient, chromatography, or polyethylene glycol (PEG) precipitation.

Provided herein are nucleic acids encoding the capsid proteins of the present disclosure. In some embodiments, nucleic acids encoding capsid proteins are present in nucleic acid vectors, e.g., plasmids. These nucleic acid vectors may be used to transfect helper cells or producer cells are described above to produce rAAV particles.

Recombinant Virus Vectors

The virus vectors of the present disclosure are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present disclosure. Nucleic acids of interest include nucleic acids encoding polypeptides, including therapeutic (e.g., for medical or veterinary uses) or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al. (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, apolipoproteins such as apoA (apoA1, apoA2, apoA4, apoA-V), apoB (apoB100, ApoB48), apoC (apoCI, apoCII, apoCIII, apoCIV), apoD, apoE, apoH, apoL, apo(a), anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, progranulin, ornithine transcarbamylase, β-globin, α-globin, spectrin, $α_1$-antitrypsin, adenosine deaminase, hypoxanthine guanine phosphoribosyl transferase, β-glucocerebrosidase, battenin, sphingomyelinase, lysosomal hexosaminidase A, branched-chain keto acid dehydrogenase, frataxin, RP65 protein, cytokines (e.g., α-interferon, β-interferon, interferon-γ, interleukin-2, interleukin-4, alpha synuclein, parkin, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), huntingtin, lysosomal acid α-glucosidase, iduronate-2-sulfatase, N-sulfogucosamine sulfohydrolase, α-galactosidase A, receptors (e.g., the tumor necrosis growth factorα soluble receptor), S100A1, ubiquitin protein ligase E3, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. No. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the disclosure.

In some embodiments, a nucleic acid sequence that directs gene editing can be delivered. For example, the nucleic acid may encode a guide RNA. In some embodiments, the guide RNA is a single guide RNA (sgRNA) comprising a crRNA sequence and a tracrRNA sequence. In some embodiments, the nucleic acid may encode a nuclease. In some embodiments, the nuclease is a zinc-finger nuclease, a homing endonuclease, a TALEN (transcription activator-like effector nuclease), a NgAgo (agronaute endonuclease), a SGN (structure-guided endonuclease), a RGN (RNA-guided nuclease), or modified or truncated variants thereof. In some embodiments, the RNA-guided nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, or modified or truncated variants thereof. In some embodiments, the Cas9 nuclease is isolated or derived from *S. pyogenes* or *S. aureus*.

In some embodiments, a nucleic acid sequence that directs gene knockdown can be delivered. For example, the nucleic acid sequence may encode a siRNA, an shRNA, a microRNA, or an antisense nucleic acid.

The virus vector may also comprise a heterologous nucleic acid that shares homology with and recombines with a locus on a host chromosome. This approach can be utilized, for example, to correct a genetic defect in the host cell.

The present disclosure also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. No. 5,882,652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present disclosure.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or—preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present disclosure provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors disclosed herein can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), Canavan's disease, amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tay-Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., IIC), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The virus vectors of the disclosure can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The virus vectors of the disclosure can also be used to produce induced pluripotent stem cells (iPS). For example, a virus vector of the disclosure can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Non-limiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The disclosure can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present disclosure permit the treatment and/or prevention of genetic diseases.

The virus vectors according to the present disclosure may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant disclosure find use in diagnostic and screening methods, whereby a nucleic acid of interest is transiently or stably expressed in a cell culture system, or alternatively, a transgenic animal model.

The virus vectors of the present disclosure can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present disclosure may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present disclosure can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the disclosure provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant disclosure. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Neutralizing Antibodies and Methods of Measuring Evasion of Neutralizing Antibodies An antibody that is capable of binding to an AAV particle and reduces its ability to infect cells in vivo is a "neutralizing antibody." In some embodiments, a neutralizing antibody is naturally occurring. In some embodiments, a neutralizing antibody is developed by injecting a recombinant rAAV particle or capsid into a subject (e.g., a rabbit, or mouse). In some embodiments, the interaction between neutralizing antibodies and an administered rAAV particle results in an immune response. In some embodiments, the interaction between neutralizing antibodies and an administered rAAV particle reduces the efficiency of the rAAV particles to transduce cells, tissue, organ, or a subject such that a higher dose of rAAV particles has to be administered to a subject to cover the loss due to antibody neutralization.

To measure the ability of a rAAV particle to evade neutralizing antibodies, transduction of cells can be carried out in the presence of neutralizing antibodies under in vitro or ex vivo conditions. In some embodiments, rAAV particles are pre-incubated with neutralizing antibodies before allowing them to transduce or infect cells. In some embodiments, a purified antibody known to neutralize AAV particles is used to test the ability of the particles to evade them. In some embodiments, a neutralizing antibody is polyclonal. In some embodiments, a neutralizing antibody is monoclonal. Non-limiting examples of neutralizing antibodies are discussed above. Other non-limiting examples of neutralizing antibodies are 4E4, 5H7, A20, C37-B, D3, ADK8, ADK1, and ADK6. Examples of neutralizing antibodies that involve the 5-fold region and/or 2/5-fold wall include ADK1b, A20, ADK5a, ADK5b, AVB, CSAL9, and HL2372. Examples of neutralizing antibodies that involve the 3-fold region 4E4, 5H7, ADK1α, ADK4, ADK6, ADK8, ADK9, C37-B, HL2370, HL2374, HL2381, and HL2383.

The antibodies disclosed herein are further described in Tseng et al. "Adeno-associated virus serotype I (AAV1)- and AAV5-antibody complex structures reveal evolutionary commonalities in parvovirus antigenic reactivity" *J. Virol.* 89(3):1794-1808 (2015) (ADK1a, ADK5a, ADK5b); Tseng et al. "Generation and characterization of anti-Adeno-associated virus serotype 8 (AAV8) and anti-AAV9 monoclonal antibodies" *J. Virol. Methods* 236:105-110 (2016) (HL2372); Wobus et al. "Monoclonal antibodies against the adeno-associated virus type 2 (AAV-2) capsid: epitope mapping and identification of capsid domains involved in AAV-2-cell interaction and neutralization of AAV-2 infection" *J. Virol.* 74(19):9281-9293 (2000), and McCraw et al. "Structure of adeno-associated virus-2 in complex with neutralizing monoclonal antibody A20" *Virology* 431(1-2):40-49 (2012) (A20); and Gurda et al. "Capsid Antibodies to Different Adeno-Associated Virus Serotypes Bind Common Regions" *J. Virol.* 87(16):9111-9124 (2013), Gurda et al. "Mapping a neutralizing epitope onto the capsid of adeno-associated virus serotype 8" *J. Virol.* 86(15):7739-7751 (2012), and Bennett et al. "AAV6 K531 serves a dual function in selective receptor and antibody ADK6 recognition" *Virology* 518:369-376 (2018) (4E4, 5H7, ADK1α, ADK4, ADK6, ADK8, ADK9, and C37-B), the disclosures of which are incorporated herein by reference to the extent they are consistent with the disclosure set forth herein. The AAV-binding fragment of the AVB antibody is commercially available from GE Healthcare ("AVB Sepharose"), and the AAV-binding fragment of the CSAL9 antibody is commercially available from ThermoFisher ("POROS CaptureSelect AAV9"), the disclosures of which are incorporated herein by reference to the extent they are consistent with the disclosure set forth herein.

The example below describes a method of purifying such antibodies, and also provides one way of measuring neutralization of AAV particles by antibodies. In some embodiments, purified immunoglobulins from a subject or animal model are used as a source of neutralizing antibodies. In some embodiments, the blood or serum of a subject is used as a source of neutralizing antibodies. In some embodiments, neutralization of an rAAV particle is tested at different ratios of particle: neutralizing antibody/ies.

Transduction of a cell by an AAV particle can be tested in a number of different ways. For example, transduction can be measured by measuring the amount of gene that is transferred into a cell (e.g., using methods such as qPCR, or protein assays for protein that is expressed from the transferred gene). In some embodiments, transduction can be measured by measuring the amount of virus that is replicated.

Measuring Seropositivity

In some embodiments, a method of administering to a subject that is seropositive for AAV a rAAV particle comprising a capsid protein of the present disclosure (e.g., a capsid protein comprising a substitution resulting in the amino acid sequence $X^1$—$X^2$-T-F—N—$X^3$—$X^4$—K-L-$X^5$ (SEQ ID NO:197), the amino acid sequence $X^1$—$X^2$-T-F—N—$X^3$—$X^4$ (SEQ ID NO:198) and/or a capsid protein comprising a modified 5-fold region) further comprises determining whether the subject is seropositive for AAV of the serotype that is to be administered.

Methods of determining whether a subject is seropositive for a particular serotype of AAV are known in the art. See e.g., Ferreira et al. (*Frontiers in Immunology*, 2014, 5(82): 1). In some embodiments, determining whether a subject is seropositive for a particular serotype of AAV comprises determining whether a subject has anti-AAV antibodies and/or T-cells directed against AAV epitopes. Presence of anti-AAV antibodies in a subject's blood or serum can be detected by incubating a sample of the subject's blood or serum with one or more AAV capsid antigens, and thereafter measuring the amount of anti-AAV antibodies bound to the one or more AAV capsid antigens. Non-limiting examples of capsid antigens include digests of AAV capsids, or a combination of purified capsid peptides, polypeptides, and/or proteins. In some embodiments, only one capsid peptide, polypeptide, or protein is used as an AAV6 antigen. In some embodiments, a protein, peptide, or polypeptide that is used as an antigen has a sequence that is comprised in AAV VP1, VP2 or VP3 capsid protein.

In some embodiments, presence of anti-AAV antibodies in a subject's blood or serum can be detected by incubating a sample of the subject's blood or serum with whole capsids.

The amount of antibody bound to capsid antigens or whole capsids can be determined using any number of biochemical and biophysical techniques. See e.g., Neri et al (*Trends in Biotechnology*, 1996, 14(12): 465), which discusses biophysical methods to determine antibody-antigen affinities, Goldberg et al. (*Current Opinion in Immunology*, 1993, 5(2): 278), which discusses methods for measuring antibody-antigen affinity based on ELISA and RIA), Quintero-Ronderos et al. (*Autoimmunity: From Bench to Bedside*, Chapter 48, Analysis of proteins and antibodies, 2013), and Rapti et al. (*Mol Ther.* 2012 January; 20(1): 73-83), each of which is incorporated herein by reference in its entirety. Non-limiting examples of biochemical approaches to measure interaction between antibodies and antigens and/or capsids include co-immunoprecipitation, bimolecular fluorescence complementation, affinity electrophoresis, ELISA and its various forms (e.g., ELISPOT). Non-limiting examples of biophysical approaches to measure interaction between antibodies and antigens and/or capsids include bio-layer interferometry, dual polarization interferometry, static light scattering, dynamic light scattering, surface plasmon resonance, fluorescence polarization/anisotropy, fluorescence correlation spectroscopy, fluorescence resonance energy transfer, and isothermal titration calorimetry. In some embodiments of detecting anti-AAV antibodies, the antigen or capsid is immobilized on a solid support for separating bound antibodies from unbound antibodies. In some embodiments, the solid support are beads.

In some embodiments, determining whether a subject is seropositive for AAV comprises determining whether a subject has T-cells directed against AAV6 epitopes. Ferreira et al. (*Frontiers in Immunology*, 2014, 5(82): 1) describes an assay for AAV1-specific T lymphocytes that can be adapted for AAV6.

Improvement of Transduction Efficiency by Decreased Reactivity to Neutralizing Antibodies In some embodiments, administering one or more rAAV particles comprising a capsid protein of the present disclosure (e.g., comprising a substitution resulting in the amino acid sequence $X^1$—$X^2$-T-F—N—$X^3$—$X^4$—K-L-$X^5$ (SEQ ID NO:197), the amino acid sequence $X^1$-$X^2$-T-F—N—$X^3$—$X^4$ (SEQ ID NO:198) and/or comprising a modified 5-fold region) as disclosed herein to a subject who is to receive or who has received rAAV will result in decreased reactivity to a neutralizing antibody, or an improvement in the transduction efficiency of the administered rAAV, relative to administering of a control; (e.g., rAAV particles that comprise VP protein without a substitution resulting in the amino acid sequence $X^1$—$X^2$-T-F—N—$X^3$—$X^4$—K-L-$X^5$ (SEQ ID NO:197), the amino acid sequence $X^1$—$X^2$-T-F—N—$X^3$—$X^4$ (SEQ ID NO:198) and/or without a modified 5-fold region). In some embodiments, any one of the methods disclosed herein involve administering one or more rAAV particles comprising a capsid protein of the present disclosure in an amount that results in decreased reactivity to a neutralizing, or an increased AAV transduction efficiency in vivo.

In some embodiments, any one of the methods disclosed herein involve administering one or more rAAV particles comprising capsid protein of the present disclosure in an amount that results in increased AAV transduction efficiency in an in vitro context, even if administered in vivo. For example, the increase in transduction efficiency for an in vivo administration of rAAV can be determined by introducing the rAAV to cells cultured in vitro in the presence of neutralizing antibodies, and comparing the transduction efficiency to cells that are introduced to rAAV without a capsid protein of the present disclosure (e.g., rAAV particles that comprise VP protein without a substitution resulting in the amino acid sequence $X^1$—$X^2$-T-F—N—$X^3$—$X^4$—K-L-$X^5$ (SEQ ID NO:197), the amino acid sequence $X^1$—$X^2$-T-F—N—$X^3$—$X^4$ (SEQ ID NO:198) and/or without a modified 5-fold region). A cell used for in vitro measurement of AAV transduction efficiency may be cultured in a culture dish, or within an organoid.

Transduction efficiency can be measured by allowing rAAV of a fixed multiplicity of infection (MOI) to infect cells and measuring the amount of expressed RNA or protein from the genetic load that is delivered by the rAAV particle. For example, a fluorescent (e.g., EGFP) or luciferase gene can be delivered using rAAV particles and after a certain time (e.g., 24 h, or 48 h), either fluorescent or luciferase RNA expression or luciferase protein can be measured using one of numerous techniques known in the art (e.g., cell fractionation, polymerase chain reaction, microscopy, and/or luciferase enzyme assays).

In some embodiments of any one of the methods provided herein, modifications to the capsid protein of an rAAV particle as disclosed herein (e.g., substitution(s) resulting in the amino acid sequence $X^1$—$X^2$-T-F—N—$X^3$—$X^4$—K-L-$X^5$ (SEQ ID NO:197), the amino acid sequence $X^1$—$X^2$-T-F—N—$X^3$—$X^4$ (SEQ ID NO:198) and/or modifications in the 5-fold region) results in decreased reactivity to neutralizing antibodies by a factor of 1.2-100 (e.g., 1.2-100, 1.3-5, 1.4-5, 1.5-2, 1.2-10, 10-20, 10-15, 12-18, 15-20, more than 1.5-fold, more than 2-fold, more than 3-fold, more than 4-fold, more than 5-fold, more than 6-fold, more than 7-fold, more than 8-fold, more than 10-fold, more than 12-fold, more than 14-fold, more than 16-fold, or more than 20-fold), compared to when rAAV particles without the modification are administered. In some embodiments of any one of the methods provided herein, modifications to the capsid protein of an rAAV particle as disclosed herein results in AAV transduction efficiency improvement by a factor of 1.2-100 times (e.g., 1.2-100, 1.3-5, 1.4-5, 1.5-2, 1.2-10, 10-20, 10-15, 12-18, 15-20, more than 1.5-fold, more than 2-fold, more than 3-fold, more than 4-fold, more than 5-fold, more than 6-fold, more than 7-fold, more than 8-fold, more than 10-fold, more than 12-fold, more than 14-fold, more than 16-fold, or more than 20-fold), compared to when rAAV particles without the modification are administered.

Generation of Antigenic Footprints on rAAV Particles

Provided herein are also methods of generating antigenic footprints on rAAV particles of various serotypes. In some embodiments, a method of generating an antigenic footprint for a particular antibody on a particular rAAV particle comprises purification of the antibody from hybridoma supernatant (e.g., using column purification), cleaving the purified antibody using an enzyme, purifying Fabs and complexing them with rAAV particles, or virus-like particles (empty capsids) at various molar ratios (e.g., 60:1, 70:1, 80:1, 90:1, 100:1, 11:1, 120:1), collecting cryo-EM data using an electron microscope, isolating individual images of the complex, performing single-particle reconstruction, interpreting the reconstructed density maps using available crystal structures of the virus capsid and a generic Fab structure, and visualizing the interacting residues between the Fab and the capsid. In some embodiments, the resolution of the capsid-Fab structure is high enough to visualize the interacting residues between the Fab and capsid. In some embodiments, a footprint generated using cryo-EM is validated using mutagenesis.

Subjects, Pharmaceutical Formulations, and Modes of Administration

Virus vectors and capsids according to the present disclosure find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the disclosure.

In particular embodiments, the present disclosure provides a pharmaceutical composition comprising a virus vector and/or capsid and/or capsid protein and/or virus particle of the disclosure in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

Provided herein are compositions comprising any one of the rAAV particles with a capsid protein of the present disclosure. In some embodiments, any one of the compositions provided herein comprises a pharmaceutically acceptable carrier. The term "carrier" refers to a diluent, adjuvant, excipient, or vehicle with which the rAAV particle is administered to a subject. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be designed.

In some embodiments, the concentration of rAAV particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In some embodiments, rAAV particles of a higher concentration than $10^{13}$ particles/ml are administered. In some embodiments, the concentration of rAAV particles administered to a subject may be on the order ranging from $10^6$ to $10^{14}$ vector genomes(vgs)/ml or $10^3$ to $10^{15}$ vgs/ml, or any values therebetween for either range (e.g., $10^6$, $10^7$, $10^8$, $10^9$, $10^{10}$, $10^{11}$, $10^{12}$, $10^{13}$, or $10^{14}$ vgs/ml). In some embodiments, rAAV particles of higher concentration than $10^{13}$ vgs/ml are administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween (e.g., $10^6$, $10^7$, $10^8$, $10^9$, $10^{10}$, $10^{11}$, $10^{12}$, $10^{13}$, or $10^{14}$ vgs/mg). In some embodiments, the dose of rAAV particles administered to a subject may be on the order ranging from $10^{12}$-$10^{14}$ vgs/kg. In some embodiments, the volume of rAAV6 composition delivered to a subject (e.g., via one or more routes of administration as described herein) is 0.0001 mL to 10 mLs.

Since rAAV particles having a capsid protein of the present disclosure as disclosed herein have a decreased reactivity to neutralizing antibody, and therefore a greater transduction efficiency compared to particles without substitution(s) resulting in the amino acid sequence $X^1$—$X^2$-T-F—N—$X^3$—$X^4$—K-L-$X^5$ (SEQ ID NO:197), the amino acid sequence $X^1$—$X^2$-T-F—N—$X^3$—$X^4$ (SEQ ID NO:198) and/or without modifications in the 5-fold region, a smaller dose of rAAV particles with a capsid protein of the present disclosure is required. Accordingly, smaller concentrations or smaller volumes of rAAV particles comprising a capsid protein of the present disclosure are needed, compared to particles without a capsid protein modified as disclosed herein.

One aspect of the present disclosure is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

Thus, the present disclosure provides a method of administering a nucleic acid to a cell, the method comprising contacting the cell with the virus vector, virus particle and/or composition of this disclosure.

A further aspect of the disclosure is a method of administering the virus vector, virus particle and/or virus capsid of this disclosure to a subject. Thus, the present disclosure also provides a method of delivering a nucleic acid to a subject, comprising administering to the subject a virus particle, virus vector and/or composition of this disclosure. Administration of the virus vectors, virus particles and/or capsids according to the present disclosure to a human subject or an animal in need thereof can be by any means known in the art. Optionally, the virus vector, virus particle and/or capsid is delivered in a treatment effective or prevention effective dose in a pharmaceutically acceptable carrier.

The virus vectors and/or capsids of the disclosure can further be administered to elicit an immunogenic response (e.g., as a vaccine). Typically, immunogenic compositions of the present disclosure comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

As described above, any one of the rAAV particles disclosed herein has the ability to evade antigenic responses by reducing the interaction with neutralizing antibodies, compared to a control (e.g., rAAV that are not modified as described herein, e.g., e.g., wild-type rAAV particles, e.g., rAAV particles that do not comprise capsid proteins comprising substitution(s) resulting in the amino acid sequence $X^1$—$X^2$-T-F—N—$X^3$—$X^4$—K-L-$X^5$ (SEQ ID NO:197) and/or the amino acid sequence $X^1$—$X^2$-T-F—N—$X^3$—$X^4$ (SEQ ID NO:198), e.g., rAAV particles that do not have a modified 5-fold region, or rAAV particles that have an unmodified 5-fold region). Examples of wild-type rAAV capsid proteins are provided in SEQ ID NOs:1-30. Any one of the rAAV particles comprising a capsid protein of the present disclosure as disclosed herein can be used to deliver one or more genes of interest to a subject who has antibodies capable of neutralizing a rAAV particle. Accordingly, provided herein is a method of administering to a subject that is seropositive for AAV of any one of the rAAV with modified capsid protein as disclosed herein.

A subject is "seropositive for AAV" if the immune response to an administered rAAV particle is statistically higher than the response in a control subject. In some embodiments, a subject is "seropositive for AAV" if the level of anti-AAV antibodies detected in the subject (e.g., in the subject's serum) is statistically higher than the level of anti-AAV antibodies detected in a control subject. A control subject may be a subject that has not previously been exposed to AAV particles (e.g., rAAV particles or a particular serotype). A subject may be "seropositive for AAV9" if exposure to AAV9 particles results in an immune response. In some embodiments, a subject that is seropositive for AAV has preexisting anti-AAV antibodies and/or T-cells directed against AAV epitopes. In some embodiments, a subject may have neutralizing antibodies that recognize AAV (i.e., "AAV antibodies" or "anti-AAV antibodies") because of a previous exposure to AAVs. The AAVs to which a subject has been previously exposed may be of a natural source (i.e., naturally occurring AAV particles). In some embodiments, AAV particles to which a subject has been previously exposed may be recombinant (i.e. rAAV particles made by man), e.g., for treatment by a therapeutic gene.

An administration of a composition of rAAV particles (e.g., comprising a therapeutic gene) may cause a subject to become seropositive for AAV. In such instances, it may not be possible to administer or re-administer rAAV particles to the subject (or at least rAAV particles of the same serotype), or administering a subsequent rAAV particle results in undesired immune response. For such instances, provided herein is a method comprising administering to a subject a subsequent rAAV particle, wherein the subsequent rAAV particle comprises a capsid protein of the present disclosure. In some embodiments, a method comprises administering to a subject a subsequent rAAV particle, wherein the subsequent rAAV particle is any one of the rAAV particles with modified capsid protein of the present disclosure.

In some embodiments, a subsequent rAAV particle is administered within 12 months (e.g., within 12, 11, 10, 9, 8, 7, 6, 5, 4, 3, 2, or 1 month) of the previously received or administered rAAV particle. In some embodiments, a subsequent rAAV particle is administered within 1 month (e.g., within 31 days, 30 days, 25 days, 20 days, 21 days, 14 days, 7 days, 5 days, 3 days, 2 days, 1 day, 18 hours, 12 hours, 6 hours, 4 hours, 2 hours, or within 1 hour) of the previously received or administered rAAV particle. In some embodiments, a subsequent rAAV particle is administered more than 12 months after (e.g., 1 year, 18 months, 2 years, 3 years, 5 years, 10 years, 20 years, or 50 years after) the previously received or administered rAAV particle.

In some embodiments, a subject has been previously administered a rAAV particle. In some embodiments, AAV particles to which a subject has been previously exposed are of serotype 1, 2, 3, 4, 5, 6, 7, 8, 9, 10, 11, 12, or 13.

Aspects of the disclosure relate to methods for use with a subject. In some embodiments, a subject is a mammal. In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a laboratory animal, e.g., a mouse. In some embodiments, the subject is a human subject. In some embodiments, a subject is an adult (e.g., an adult human, or adult mouse). In some embodiment, a subject is juvenile (e.g., an infant, or a teenager).

In some embodiments, "administering" or "administration" means providing a material to a subject in a manner that is pharmacologically useful. In some embodiments, a rAAV particle is administered to a subject enterally. In some embodiments, an enteral administration is oral. In some embodiments, a rAAV particle is administered to the subject parenterally. In some embodiments, a rAAV particle is administered to a subject subcutaneously, intraocularly, intravitreally, subretinally, intravenously (IV), intracerebroventricularly, intramuscularly, intrathecally (IT), intracisternally, intraperitoneally, via inhalation, topically, or by direct injection to one or more cells, tissues, or organs. In some embodiments, a rAAV particle is administered to the subject by injection into the hepatic artery or portal vein.

In some embodiments, any one of the rAAV particles of the present disclosure is administered to treat a disease in a subject. To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., a neurodegenerative disease using a rAAV9 particle with a modified capsid protein as disclosed herein. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently. Furthermore, use of particular AAV serotypes to target particular tissue types or organs is well known based on AAV tropism. For example, AAV1, AAV2, AAV4, AAV5, AAV8, or AAV9 may be used to target the central nervous system, AAV1, AAV8, or AAV9 may be used to target the heart. AAV2 may be used to target the kidney. AAV3B, AAV7, AAV8, or AAV9 may be used to target the liver. AAV4, AAV5, AAV6, or AAV9 may be used to target the lungs. AAV1, AAV2, AAV4, AAV5, or AAV8 may be used to target different regions of the eye. AAV1, AAV6, AAV7, AAV8, or AAV9 may be used to target skeletal muscle.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator intermus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, stemohyoid, stemothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the disclosure, the virus vectors and/or capsids of the disclosure can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the disclosure can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present disclosure is administered to skeletal muscle, diaphragm muscle and/or cardiac muscle (e.g., to treat and/or prevent muscular dystrophy, heart disease [for example, PAD or congestive heart failure]).

In representative embodiments, the disclosure is used to treat and/or prevent disorders of skeletal, cardiac and/or diaphragm muscle.

In a representative embodiment, the disclosure provides a method of treating and/or preventing muscular dystrophy in a subject in need thereof, the method comprising: administering a treatment or prevention effective amount of a virus vector of the disclosure to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the disclosure can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent publication US 2002/0192189.

Thus, as one aspect, the disclosure further encompasses a method of treating and/or preventing a metabolic disorder in a subject in need thereof, the method comprising: administering a treatment or prevention effective amount of a virus vector of the disclosure to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory, according to this embodiment, administration to the skeletal muscle can result in secretion of the polypeptide into the systemic circulation and delivery to target tissue(s). Methods of delivering virus vectors to skeletal muscle is described in more detail herein.

The disclosure can also be practiced to produce antisense RNA, RNAi or other functional RNA (e.g., a ribozyme) for systemic delivery.

The disclosure also provides a method of treating and/or preventing congenital heart failure or PAD in a subject in need thereof, the method comprising administering a treatment or prevention effective amount of a virus vector of the disclosure to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the disclosure in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the present disclosure.

In particular embodiments, the delivery vectors of the disclosure may be administered to treat diseases of the CNS, including genetic disorders, neurodegenerative disorders, psychiatric disorders and tumors. Illustrative diseases of the CNS include, but are not limited to Alzheimer's disease, Batten's disease, Parkinson's disease, Huntington's disease, Canavan disease, Gaucher's disease, Leigh's disease, Hunter Syndrome, Refsum disease, Tourette syndrome, primary lateral sclerosis, amyotrophic lateral sclerosis, progressive muscular atrophy, Pick's disease, Sanfilipo syndrome, Angelman syndrome, muscular dystrophy, multiple sclerosis, myasthenia gravis, Binswanger's disease, trauma due to spinal cord or head injury, Friedreich's ataxia, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present disclosure can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the disclosure.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present disclosure may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the disclosure can also be used to treat epilepsy, which is marked by multiple seizures over time.

In one representative embodiment, somatostatin (or an active fragment thereof) is administered to the brain using a delivery vector of the disclosure to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

EXAMPLES

Example 1: Evaluation of Antibody Escape Capability of Mutant AAV Capsids

A library of sequences with randomized modifications in the footprint of the antibody HL2372 was generated and screened for the ability to produce replication competent AAV particles, to screen out nonviable sequences which may not fold, assemble, or package DNA appropriately. Replication competent AAV mutants comprising the sequences able to evade binding by the antibody HL2372 that can assemble into genome packaging particles were selected and generated. Viable capsid sequences identified from the methods disclosed herein as modified in the footprint of, and thus able to evade binding by, the antibody HL2372 are shown in FIG. 1. Underlined residues match that position in the wild-type AAV8 sequence (SEQ ID NO:8). Mutated residues are P661, T662, Q666, S667, N670. Different amino acid residues that were evolved following selection of AAV capsid libraries randomized in each position are highlighted. The mutated residues were evolved to yield similar viral particle numbers compared to the wild type AAV sequence.

Exemplary AAV mutants (e.g., comprising hiA, hiC, and xx1 capsid sequences) packaging green fluorescent protein (GFP) sequences were further incubated with increasingly concentrated amounts of a neutralizing antibody HL2372 (shown as fold dilutions), as shown in FIG. 2. The capsid containing the wild type version of the amino acid sequence was readily neutralized in highly diluted samples (at 1:4480); GFP expression (white dots) in cultured cells was markedly reduced. In contrast, mutants hiA and hiC and to a lesser extent xx1 were not neutralized, as GFP expression was robust, supporting the notion that these evolved variants evade HL2372. These results affirm that evolution of new amino acid residues at this surface motif yields novel, synthetic AAV variants that can evade neutralizing antibodies against AAV capsids.

Example 2: Generation of Antigenic Footprints on rAAV Particles

Expression of and purification of AAV8 and AAV9 capsids: Recombinant AAV8 and AAV9 virus-like particles (VLPs) were expressed using the Bac-to-Bac baculovirus-Sf9 insect cell expression system (Gibco/Invitrogen, Carlsbad, CA) and purified using a 20% sucrose cushion followed by sucrose gradient (5 to 40% [wt/vol]) as previously reported (Lane et al. 2005; Mitchell et al. 2009). Purified AAV8 and AAV9 VLPs were concentrated to 1-3 mg/ml and buffer exchanged into 1×PBS, pH 7.4. The concentration of the samples was estimated by optical density measurements (using OD280 and E=1.7 for calculation in mg/ml), as well as SDS-PAGE gel electrophoresis with BSA concentration standards. Prior to use, the purity and integrity of the VLPs were also monitored by SDS-PAGE and negative stain EM, respectively.

Generation of AAV capsid specific monoclonal antibodies: Six-week-old female BALB/CByj mice were immunized three times with subcutaneous injections of 5, 10, 25, 50 or 75 µg of AAV capsids at 21-day intervals and one intraperitoneal injection on day 120 as the last boost. The first three subcutaneous injections were accompanied by a Sigma Adjuvant System (Sigma-Aldrich, St. Louis, MO), which contain 0.5 mg monophosphoryl lipid A, 0.5 mg synthetic trehalose dicorynomycolate in 44 µl squalene oil, 0.2% TWEEN 80 and water. Test bleeds from immunized animals were obtained 10-14 days after every booster injection, following animal care protocols. The collected sera were tested for high specific antibody response using ELISA and Dot Blot (against intact capsid) assays as described below. Four days after the final boost injection, the splenocytes of immunized mice were fused with mouse myeloma Sp2/0 cells using 50% PEG 1500 (polyethylene glycol) as the fusing agent. The fused hybrids were cultured in HAT (hypoxanthine-aminopterin-thymidine) (Sigma-Aldrich, St. Louis, MO) supplemented Dulbeccos Modified Eagles Medium (DMEM) to eradicate the unfused myeloma cells. To obtain the positive hybridoma clones, with highest specific anti-AAV capsid antibody response, the supernatants from the resulting hybridoma cells were collected and screened by total of 5 rounds of ELISA assays, as described below.

Screening of mice serum or hybridoma supernatants using VLP ELISA: The supernatants of hybridomas were screened using AAV8 and AAV9 virus-like particles (VLPs) ELISA assays. Briefly, Nunc Maxisorp 96 well plates (Thermo Scientific, Rochester, NY) were coated with AAV VLPs at 4° C. O/N prior to each ELISA assay. The plates were then blocked with 1% BSA in PBS at RT for 1 h, and then washed with washing buffer (1×PBS with 0.5% Tween 20). The immunized mouse serum or the hybridoma supernatants were applied to the plate and incubated at RT for 1 h. After washes, the secondary antibody, a rabbit anti-mouse IgG whole molecule AP (alkaline phosphatase), goat anti-mouse IgG gamma chain specific AP, or goat anti-mouse IgM mu chain specific AP (Sigma-Aldrich, St. Louis, MO) were added at 1:1000, 1:4000, and 1:4000 dilution in PBS with 1% BSA, respectively, for 1 h at RT. Finally after several washes, the substrates, p-Nitrophenyl Phosphate Disodium (Sigma), was applied to the plate and incubated for 1 h, then optical density readings were taken at 405 nm using a Molecular Devices SpectraMax 384 Plus (Sunnyvale, CA).

Anti-AA V VLP dot blot analysis: AAV VLPs were allowed to adsorb onto supported nitrocellulose membranes (Bio-Rad, Hercules, CA) in the dot blot manifold (Schleicher and Schuell, Dassel, Germany). Excess fluid was drawn through the membrane by vacuum filtration. The membrane was removed from the manifold and blocked with 10% milk in PBS, pH 7.4 for 1 h. Primary antibody in the form of anti-AAV mouse serum, hybridoma supernatant, or the purified MAbs, in different dilutions depending on the sample being tested, was applied to the membrane in PBS with 5% milk and incubated for 1 h. Following this, the membrane was washed with PBS and horse radish peroxidase (HRP)-linked secondary antibody was applied at a dilution of 1:5000 in PBS and incubated for 1 h. The membrane was washed with PBS and then Super Signal West Pico Chemiluminescent Substrate (ThermoFisher, Waltham, WA) was applied to the membrane and the signal detected on X-ray film. The B1 antibody, which binds to the C terminus of the viral capsid proteins in all the AAV serotypes except for AAV4 (Wistuba et al. 1995), was used as a control to confirm the presence of AAV capsid proteins using denatured capsids (boiled and blotted). ADK8 and ADK9 (Sonntag et al. 2011) were used as positive controls for AAV8 and AAV9, respectively, to detect in intact (non-boiled) capsids.

Determination of the isotypes for the anti-AAVMAbs: Isotypes of newly generated anti-AAV antibodies were determined using the IsoStrip Mouse Monoclonal Antibody Isotyping Kit (Santa Cruz Biotechnology, Santa Cruz, CA). The supernatant of the hybridoma cell cultures were diluted 1:10 to 1:100 in PBS depending on the concentration of antibodies in the supernatant. The diluted samples were loaded onto the development tube provided in the kit and incubated for 30 s. One isotyping strip was placed in each development tube and incubated for 5-10 min until appearance of the blue bands for which their positions indicate the isotype (IgG1, IgG2a, IgG2b, IgG3, IgM or IgA) and the light chain type (kappa or lambda) of the MAb.

Neutralization assay: The neutralization abilities of the newly generated anti-AAV8 and anti-AAV9 antibodies were assayed in HeLa cells (Veron et al. *J Immunol.* 2012; 188:6418-6424). Briefly, luciferase gene packaged recombinant rAAV8-Luc or rAAV9-Luc vectors were mixed with different hybridoma supernatants in a volume ratio 1:1, and then used to infect HeLa cells at a 10,000 MOI (multiplicity of infection). After 24 hours, the cells were lysed and the expressed luciferase activity was assayed for each complex using a luciferase assay (Promega, Madison, WI) as described in the manufacturer's protocol. In this assay, ADK4, a MAb that specifically recognizes AAV4 (Kuck et al. *J Virol Methods.* 2007; 140:17-24) was used as a negative control while ADK8 and ADK9, known to neutralize infection by AAV8 (Gurda et al. *J Virol.* 2012; 86:7739-7751) and AAV9 (Sonntag et al. *J Virol.* 2011; 85:12686-12697), respectively, were used as positive control.

Identification of antigenic footprints: Purified FAbs were complexed with AAV virus-like particles (VLPs), at a ratio of 1 to 2 ligand molecules per VP binding site on the capsid to result in a ligand:capsid molar ratio of 60-120:1. These complexes were used to collect cryo-electron microscopy data on an FEI Tecnai TF20 electron microscope. Individual complex images were isolated and used for single-particle reconstruction. Reconstructed density maps were interpreted using available crystal structures of the virus capsids and a generic FAb structure, which were docked into complex density maps to analyze the interface between the two models. The antibody footprint was identified by visualizing the interacting residues followed by mutagenesis to confirm.

Figure 3:
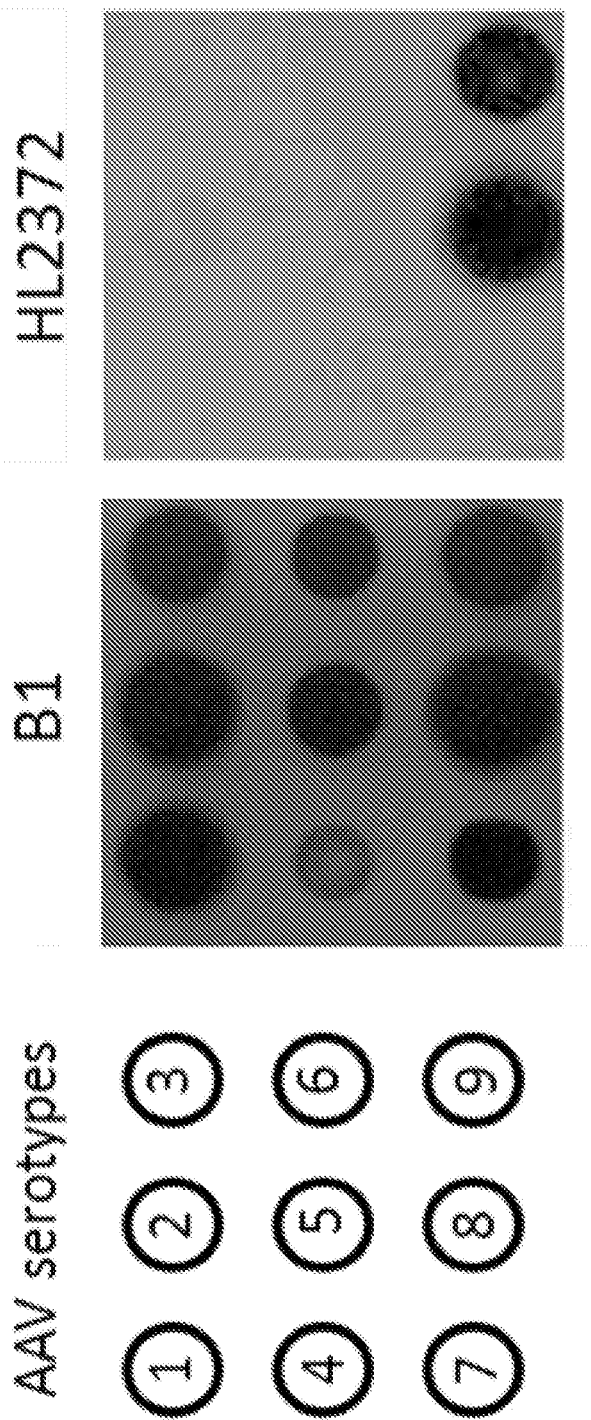

Results: FIG. 3 shows the cross reactivity of the HL antibodies. Different AAV capsids were loaded on the dot-blot membrane in the order shown, and presence of protein was confirmed by detection by B1 antibody, which recognizes denatured VP. Using the same loading pattern, capsids of different AAV serotypes were also detected by the HL2372 antibody. Only AAV8 and AAV9 reacted.

Figure 4:
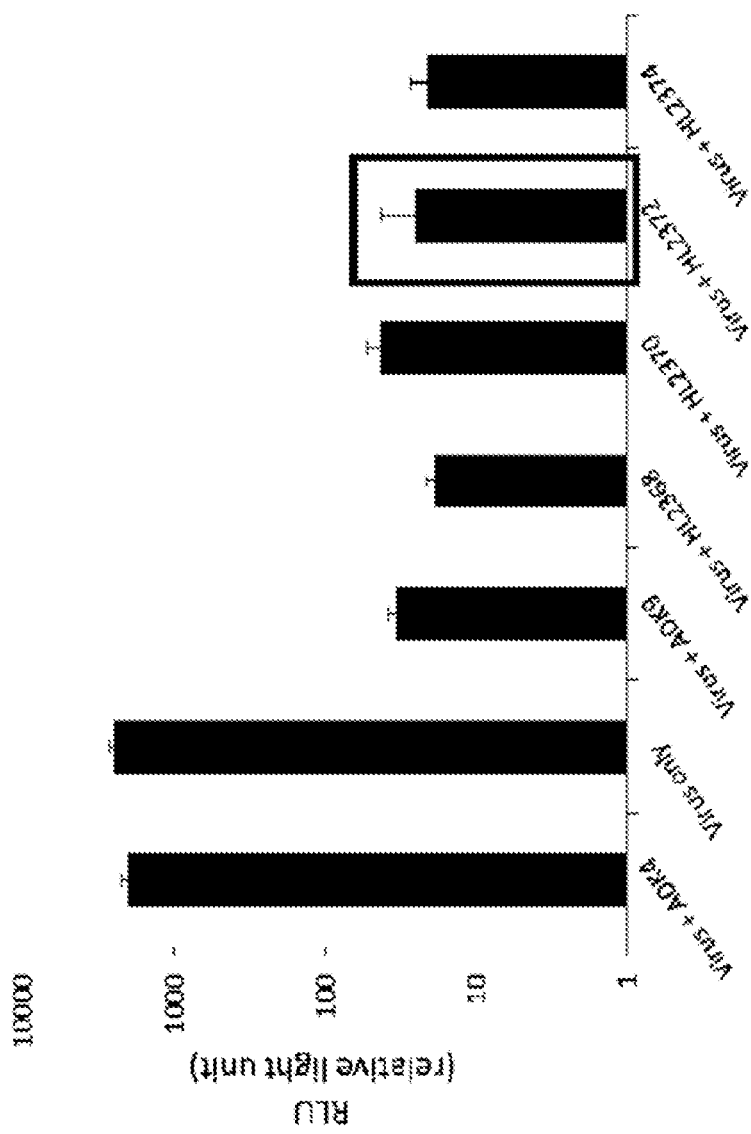

In in vitro neutralization assays, the transduction efficiency of rAAV9 was found to be decreased by the following antibodies: HL2368, HL2370, HL2372, and HL2374 (FIG. 4). The ADK4 antibody was used as a negative control, and the ADK9 antibody was used as a positive control, respectively.

Figure 5:
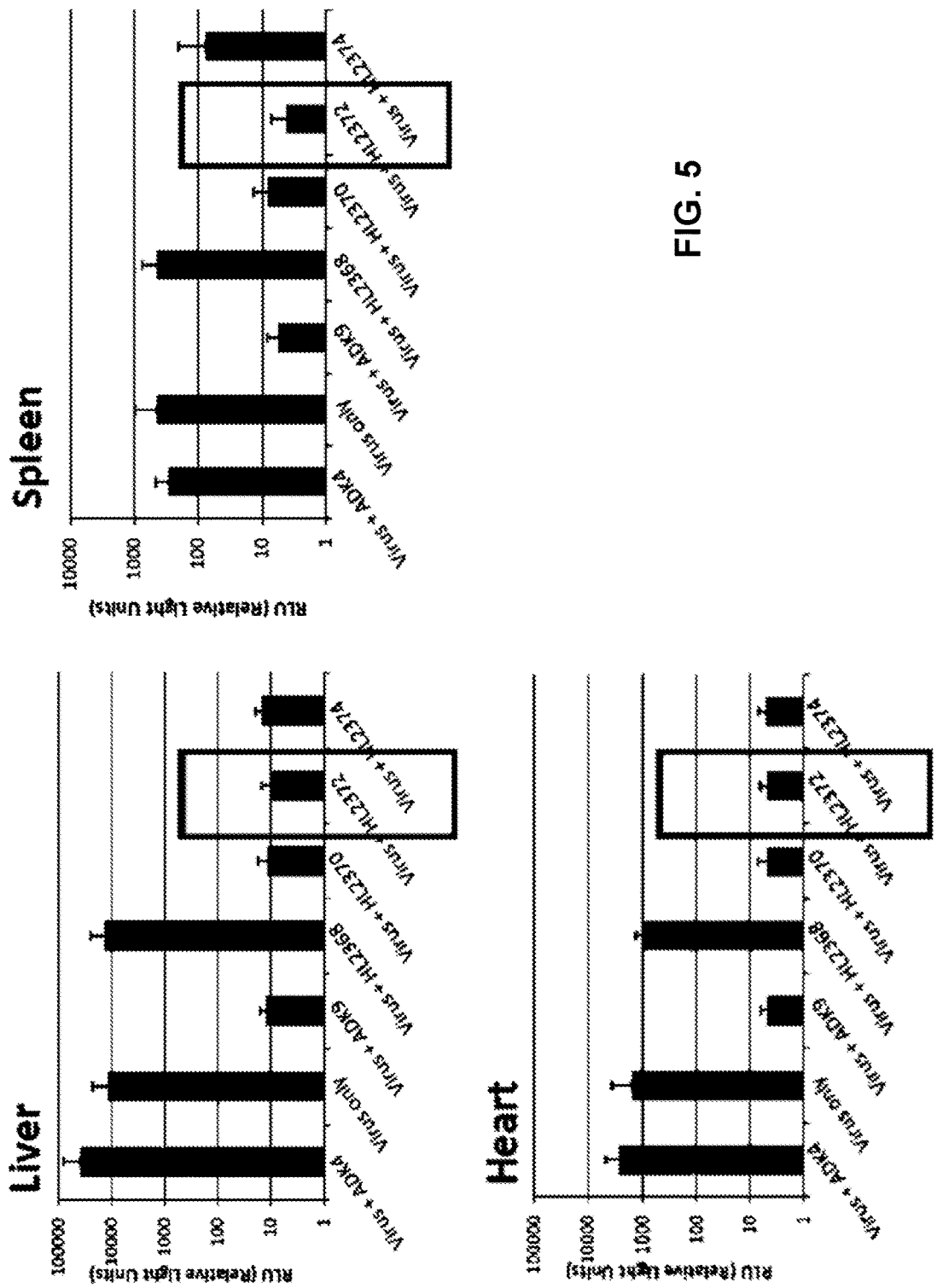

When tested in vivo, HL2370, HL2372, and HL2374 caused a decrease in transduction efficiency in the liver, spleen, and heart of Balb/C mice (FIG. 5).

FIGS. 6A-6B show antigenic footprints of the HL2372 antibody obtained from complexes of HL2372 with AAV8 VLP, and HL2372 with AAV9 VLP, respectively.

Footprints for other complexes of antibodies and AAV VLPs that were generated can be found in Table 5.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

The foregoing is illustrative of the present invention, and is not to be construed as limiting thereof. The invention is defined by the following claims, with equivalents of the claims to be included therein. Without further elaboration, it is believed that one skilled in the art can, based on the above description, utilize the present disclosure to its fullest extent. The specific embodiments described herein are, therefore, to be construed as merely illustrative, and not limiting of the remainder of the disclosure in any way whatsoever. All publications cited herein are incorporated by reference for the purposes or subject matter referenced herein.

TABLE 1

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |

TABLE 1-continued

| AAV Serotypes/Isolates | GenBank Accession Number |
|---|---|
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

TABLE 2

| Amino Acid Residue | Three-Letter Code | One-Letter Code |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 4

Shared 5-fold residues between AAV particles of different serotypes complexed with particular neutralizing antibodies. AAV1 numbering based on the reference amino acid sequence for AAV1 capsid protein identified herein as SEQ ID NO: 18 is used.

| Amino acid position | AAV1: AVB | AAV9: CSAL9 | AAV8: HL2372 | AAV9: HL2372 | AAV5: ADK5a | AAV5: ADK5b |
|---|---|---|---|---|---|---|
| 250 | X |  |  |  | X |  |
| 251 | X | X | X |  | X | X |
| 252 | X | X | X |  | X | X |
| 253 | X | X | X |  | X | X |
| 254 | X | X | X |  | X | X |
| 255 | X | X | X | X | X | X |
| 256 | X |  | X | X | X | X |
| 257 | X |  | X | X | X | X |
| 258 | X |  | X | X | X | X |
| 259 |  | X | X | X |  |  |
| 260 |  | X | X | X |  |  |
| 261 |  | X | X | X |  |  |
| 262 |  | X | X | X |  |  |
| 263 |  | X | X | X |  |  |
| 264 |  | X | X | X |  |  |
| 265 |  | X | X | X | X |  |
| 266 |  |  | X | X | X |  |
| 324 | X | X |  | X |  | X |
| 325 | X | X |  | X |  | X |
| 326 | X | X |  | X |  | X |
| 327 | X | X |  | X |  | X |
| 328 | X | X |  | X |  | X |
| 329 | X | X |  | X |  | X |
| 330 | X | X |  | X |  |  |
| 331 | X | X |  | X |  | X |
| 332 | X | X |  | X |  |  |
| 333 | X | X |  | X |  | X |
| 365 |  |  |  |  | X |  |
| 366 |  |  |  |  | X | X |
| 367 |  |  |  |  | X |  |
| 368 |  |  |  |  | X | X |
| 369 |  |  |  |  |  | X |
| 370 |  |  |  | X | X |  |
| 371 |  |  |  |  | X |  |
| 372 |  |  |  |  |  | X |
| 374 |  |  |  |  |  | X |
| 375 |  |  |  |  | X |  |
| 544 |  |  |  |  | X | X |
| 545 |  |  |  |  | X | X |
| 546 | X |  |  |  | X | X |
| 547 | X |  |  |  | X | X |
| 548 | X |  |  |  | X | X |
| 549 | X |  |  |  | X | X |
| 550 | X |  |  |  | X | X |
| 551 |  |  |  |  | X | X |
| 557 | X |  |  |  | X | X |
| 655 | X |  |  |  |  |  |
| 656 | X |  | X | X |  | X |
| 657 | X | X | X | X |  | X |
| 658 | X | X | X | X |  | X |
| 659 | X | X | X | X | X | X |
| 660 | X | X | X | X | X | X |
| 661 | X | X | X | X | X | X |
| 662 | X | X | X | X | X | X |
| 663 | X | X | X | X | X | X |
| 664 | X | X | X | X |  | X |
| 665 | X | X | X | X | X | X |
| 666 | X | X | X | X | X | X |
| 667 | X | X | X | X | X | X |
| 668 | X | X | X | X | X | X |
| 669 | X | X | X | X | X | X |
| 670 | X | X | X | X | X | X |
| 671 | X | X | X | X | X | X |
| 672 | X | X | X | X | X | X |
| 673 | X | X |  | X |  | X |
| 674 | X | X |  |  |  |  |
| 716 | X |  |  |  | X |  |
| 717 | X |  |  |  | X |  |
| 718 | X |  | X | X | X |  |
| 719 | X |  |  |  | X |  |
| 720 | X |  |  |  | X |  |

TABLE 5

Antigenic footprints for various particular AAV serotypes and neutralizing antibodies. Numbering represents amino acid positions for AAV serotypes listed. Numbering is based on the reference amino acid sequence identified herein of the capsid protein of the respective AAV serotypes listed below.

| Ligand | Footprint Residues | VR (Variable region) |
|---|---|---|
| AAV1:AVB | 250-258 | I |
|  | 324-333, 371, 372 | II |
|  | 546-550, 557 | VII |
|  | 655-674 | HI-loop |
|  | 716-721 | IX |
| AAV2:AVB | 250-258 | I |
|  | 323-332, 370, 371 | II |
|  | 545-548, 556 | VII |
|  | 655-673 | HI-loop |
|  | 715-720 | IX |
| AAV5:AVB | 240-248 | I |
|  | 314-323, 372, 373 | II |
|  | 532-535, 546 | VII |
|  | 644-662 | HI-loop |
|  | 704-709 | IX |
| AAV9:CSAL9 | 251-255, 264 | I |
|  | 325-334 | II |
|  | 656-674 | HI-loop |
| AAV8:HL2372 | 252-266 | I |
|  | 326-335 | II |
|  | 658-676 | HI-loop |
|  | 720 | IX |

TABLE 5-continued

Antigenic footprints for various particular AAV serotypes and neutralizing
antibodies. Numbering represents amino acid positions for AAV serotypes listed.
Numbering is based on the reference amino acid sequence identified herein of the capsid
protein of the respective AAV serotypes listed below.

| Ligand | Footprint Residues | VR (Variable region) |
|---|---|---|
| AAV9:HL2372 | 251-266 | I |
| | 325-334 | II |
| | 657-673 | HI-loop |
| | 718 | IX |
| AAV5:ADK5a | 218, 240-258, 261, 263, 267, 279 | I |
| | 331, 350, 355-360, 364, 365, 377, 378, 395 | II |
| | 429-432, 437, 450, 451, 453-456, 458, 459 | III |
| | 530-543, 545-548 | IV |
| | 639, 641, 642, 648-651, 653-658, 660-662 | VI, HI-Loop |
| | 697-700, 704-712 | IX |
| AAV5:ADK5b | 241-248 | I |
| | 313-319, 321, 323, 355, 356, 358-362 | II |
| | 440-443, 446-449 | III |
| | 530-548 | IV |
| | 645-651, 653-661 | VI, HI-Loop |
| | 697, 698, 704-712 | IX |

TABLE 6

| Serotype | Position 1 | Position 2 |
|---|---|---|
| AAV1 | A263X | T265X |
| AAV2 | Q263X | -265X |
| AAV3A | Q263X | -265X |
| AAV3B | Q263X | -265X |
| AAV4 | S257X | -259X |
| AAV5 | G253X | V255X |
| AAV6 | A263X | T265X |
| AAV7 | E264X | A266X |
| AAV8 | G264X | S266X |
| AAV9 | S263X | S265X |

Where, (X) → mutation to any amino acid;
(−) → insertion of any amino acid
Note:
Position 2 inserts are indicated by the site of insertion

SEQUENCES

AAV1 capsid protein (GenBank Accession No. AAD27757)
(SEQ ID NO: 1)

```
  1 MAADGYLPDW LEDNLSEGIR EWWDLKPGAP KPKANQQKQD DGRGLVLPGY KYLGPENGLD

61 KGEPVNAADA AALEHDKAYD QQLKAGDNPY LRYNHADAEF QERLQEDTSE GGNLGRAVEQ

121 AKKRVLEPLG LVEEGAKTAP GKKRPVEQSP QEPDSSSGIG KTGQQPAKKR LNFGQTGDSE

181 SVPDPQPLGE PPATPAAVGP TTMASGGGAP MADNNEGADG VGNASGNWHC DSTWLGDRVI

241 TTSTRTWALP TYNNHLYKQI SSASTGASND NHYFGYSTPW GYFDFNRFHC HESPRDWQRL

301 INNNWGFRPK RLNEKLFNIQ VKEVTTNDGV TTIANNLTST VQVESDSEYQ LPYVLGSAHQ

361 GCLPPFPADV FMIPQYGYLT LNNGSQAVGR SSFYCLEYFP SQMLRTGNNF TESYTFEEVP

421 FHSSYAHSQS LDRLMNPLID QYLYYLNRTQ NQSGSAQNKD LLESRGSPAG MSVQPKNWLP

481 GPCYRQQRVS KTKTDNNNSN FTWTGASKYN LNGRESIINP GTAMASHKDD EDKFFPMSGV

541 MIFGKESAGA SNTALDNVMI TDEEEIKATN PVATERFGTV AVNFQSSSTD PATGDVHAMG

601 ALPGMVWQDR DVYLQGPIWA KIPHTDGHFH PSPLMGGFGL KNPPPQILIK NTPVPANPPA

661 EFSATKFASE ITQYSTGQVS VEIEWELQKE NSKRWNPEVQ YTSNYAKSAN VDFTVDNNGL

721 YTEPRPIGTR YLTRPL
```

AAV2 capsid protein (GenBank Accession No. YP_680426)
(SEQ ID NO: 2)

```
  1 MAADGYLPDW LEDTLSEGIR QWWKLKPGPP PPKPAERHKD DSRGLVLPGY KYLGPENGLD

61 KGEPVNEADA AALEHDKAYD RQLDSGDNPY LKYNHADAEF QERLKEDTSF GGNLGRAVEQ

121 AKKRVLEPLG LVEEPVKTAP GKKRPVEHSP VEPDSSSGTG KAGQQPARKR LNFGQTGDAD
```

```
                              SEQUENCES
181 SVPDPQPLGQ PPAAPSGLGT NTMATGSGAP MADNNEGADG VGNSSGNWHC DSTWMGDRVI

241 TTSTRTWALP TYNNHLYKQI SSQSGASNDN HYFGYSTPWG YFDENRFHCH FSPRDWQRLI

301 NNNWGFRPKR LNFKLENIQV KEVTQNDGTT TIANNLTSTV QVETDSEYQL PYVLGSAHQG

361 CLPPFPADVF MVPQYGYLTL NNGSQAVGRS SFYCLEYFPS QMLRTGNNET FSYTFEDVPF

421 HSSYAHSQSL DRLMNPLIDQ YLYYLSRTNT PSGTTTQSRL QFSQAGASDI RDQSRNWLPG

481 PCYRQQRVSK TSADNNNSEY SWTGATKYHL NGRDSLVNPG PAMASHKDDE EKFFPQSGVL

541 IFGKQGSEKT NVDIEKVMIT DEEEIRTTNP VATEQYGSVS TNLQRGNRQA ATADVNTQGV

601 LPGMVWQDRD VYLQGPIWAK IPHTDGHFHP SPLMGGFGLK HPPPQILIKN TPVPANPSTT

661 FSAAKFASFI TQYSTGQVSV EIEWELQKEN SKRWNPEIQY TSNYNKSVNV DETVDINGVY

721 SEPRPIGTRY LTRNL

AAV3 capsid protein (GenBank Accession No. AAC55049)
                                                        (SEQ ID NO: 3)
  1 MAADGYLPDW LEDNLSEGIR EWWALKPGVP QPKANQQHQD NRRGLVLPGY KYLGPGNGLD

61 KGEPVNEADA AALEHDKAYD QQLKAGDNPY LKYNHADAEF QERLQEDTSF GGNLGRAVEQ

121 AKKRILEPLG LVEEAAKTAP GKKGAVDQSP QEPDSSSGVG KSGKQPARKR LNFGQTGDSE

181 SVPDPQPLGE PPAAPTSLGS NTMASGGGAP MADNNEGADG VGNSSGNWHC DSQWLGDRVI

241 TTSTRTWALP TYNNHLYKQI SSQSGASNDN HYFGYSTPWG YEDENRFHCH FSPRDWQRLI

301 NNNWGFRPKK LSFKLFNIQV RGVTQNDGTT TIANNLTSTV QVFTDSEYQL PYVLGSAHQG

361 CLPPFPADVF MVPQYGYLTL NNGSQAVGRS SFYCLEYFPS QMLRTGNNFQ FSYTFEDVPF

421 HSSYAHSQSL DRLMNPLIDQ YLYYLNRTQG TTSGTTNQSR LLFSQAGPQS MSLQARNWLP

481 GPCYRQQRLS KTANDNNNSN FPWTAASKYH LNGRDSLVNP GPAMASHKDD EEKFFPMHGN

541 LIFGKEGTTA SNAELDNVMI TDEEEIRTTN PVATEQYGTV ANNLQSSNTA PTTGTVNHQG

601 ALPGMVWQDR DVYLQGPIWA KIPHTDGHFH PSPLMGGFGL KHPPPQIMIK NTPVPANPPT

661 TFSPAKFASF ITQYSTGQVS VEIEWELQKE NSKRWNPEIQ YTSNYNKSVN VDFTVDTNGV

721 YSEPRPIGTR YLTRNL

AAV4 capsid protein (GenBank Accession No. NP_044927)
                                                        (SEQ ID NO: 4)
  1 MTDGYLPDWL EDNLSEGVRE WWALQPGAPK PKANQQHQDN ARGLVLPGYK YLGPGNGLDK

61 GEPVNAADAA ALEHDKAYDQ QLKAGDNPYL KYNHADAEFQ QRLQGDTSEG GNLGRAVEQA

121 KKRVLEPLGL VEQAGETAPG KKRPLIESPQ QPDSSTGIGK KGKQPAKKKL VFEDETGAGD

181 GPPEGSTSGA MSDDSEMRAA AGGAAVEGGQ GADGVGNASG DWHCDSTWSE GHVTTTSTRT

241 WVLPTYNNHL YKRLGESLQS NTYNGFSTPW GYFDENRFHC HESPRDWQRL INNNWGMRPK

301 AMRVKIFNIQ VKEVTTSNGE TTVANNLTST VQIFADSSYE LPYVMDAGQE GSLPPFPNDV

361 FMVPQYGYCG LVTGNTSQQQ TDRNAFYCLE YFPSQMLRTG NNFEITYSFE KVPFHSMYAH

421 SQSLDRLMNP LIDQYLWGLQ STTTGTTLNA GTATTNETKL RPTNFSNFKK NWLPGPSIKQ

481 QGFSKTANQN YKIPATGSDS LIKYETHSTL DGRWSALTPG PPMATAGPAD SKESNSQLIF

541 AGPKQNGNTA TVPGTLIFTS EEELAATNAT DTDMWGNLPG GDQSNSNLPT VDRLTALGAV

601 PGMVWQNRDI YYQGPIWAKI PHTDGHFHPS PLIGGFGLKH PPPQIFIKNT PVPANPATTE

661 SSTPVNSFIT QYSTGQVSVQ IDWEIQKERS KRWNPEVQFT SNYGQQNSLL WAPDAAGKYT

721 EPRAIGTRYL THHL
```

| SEQUENCES |
|---|
| AAV5 capsid protein (GenBank Accession No. AAD13756)<br>(SEQ ID NO: 5)<br>  1 MSFVDHPPDW LEEVGEGLRE FLGLEAGPPK PKPNQQHQDQ ARGLVLPGYN YLGPGNGLDR<br> 61 GEPVNRADEV AREHDISYNE QLEAGDNPYL KYNHADAEFQ EKLADDTSFG GNLGKAVFQA<br>121 KKRVLEPFGL VEEGAKTAPT GKRIDDHFPK RKKARTEEDS KPSTSSDAEA GPSGSQQLQI<br>181 PAQPASSLGA DTMSAGGGGP LGDNNQGADG VGNASGDWHC DSTWMGDRVV TKSTRTWVLP<br>241 SYNNHQYREI KSGSVDGSNA NAYFGYSTPW GYFDENRFHS HWS PRDWQRL INNYWGERPR<br>301 SLRVKIFNIQ VKEVTVQDST TTIANNLTST VQVETDDDYQ LPYVVGNGTE GCLPAFPPQV<br>361 FTLPQYGYAT LNRDNTENPT ERSSFFCLEY FPSKMLRTGN NFEFTYNFEE VPFHSSFAPS<br>421 QNLFKLANPL VDQYLYRFVS TNNTGGVQEN KNLAGRYANT YKNWFPGPMG RTQGWNLGSG<br>481 VNRASVSAFA TTNRMELEGA SYQVPPQPNG MTNNLQGSNT YALENTMIEN SQPANPGTTA<br>541 TYLEGNMLIT SESETQPVNR VAYNVGGQMA TNNQSSTTAP ATGTYNLQEI VPGSVWMERD<br>601 VYLQGPIWAK IPETGAHFHP SPAMGGFGLK HPPPMMLIKN TPVPGNITSF SDVPVSSFIT<br>661 QYSTGQVTVE MEWELKKENS KRWNPEIQYT NNYNDPQFVD FAPDSTGEYR TTRPIGTRYL<br>721 TRPL |
| AAV6 capsid protein (GenBank Accession No. AAB95450)<br>(SEQ ID NO: 6)<br>  1 MAADGYLPDW LEDNLSEGIR EWWDLKPGAP KPKANQQKQD DGRGLVLPGY KYLGPENGLD<br> 61 KGEPVNAADA AALEHDKAYD QQLKAGDNPY LRYNHADAEF QERLQEDTSF GGNLGRAVEQ<br>121 AKKRVLEPFG LVEEGAKTAP GKKRPVEQSP QEPDSSSGIG KTGQQPAKKR LNFGQTGDSE<br>181 SVPDPQPLGE PPATPAAVGP TTMASGGGAP MADNNEGADG VGNASGNWHC DSTWLGDRVI<br>241 TTSTRTWALP TYNNHLYKQI SSASTGASND NHYFGYSTPW GYFDFNRFHC HESPRDWQRL<br>301 INNNWGFRPK RLNFKLFNIQ VKEVTTNDGV TTIANNLTST VQVESDSEYQ LPYVLGSAHQ<br>361 GCLPPFPADV FMIPQYGYLT LNNGSQAVGR SSFYCLEYFP SQMLRTGNNF TFSYTFEDVP<br>421 FHSSYAHSQS LDRLMNPLID QYLYYLNRTQ NQSGSAQNKD LLFSRGSPAG MSVQPKNWLP<br>481 GPCYRQQRVS KTKTDNNNSN FTWTGASKYN LNGRESIINP GTAMASHKDD KDKFFPMSGV<br>541 MIFGKESAGA SNTALDNVMI TDEEEIKATN PVATERFGTV AVNLQSSSTD PATGDVHVMG<br>601 ALPGMVWQDR DVYLQGPIWA KIPHTDGHFH PSPLMGGFGL KHPPPQILIK NTPVPANPPA<br>661 EFSATKFASF ITQYSTGQVS VEIEWELQKE NSKRWNPEVQ YTSNYAKSAN VDFTVDNNGL<br>721 YTEPRPIGTR YLTRPL |
| AAV7 capsid protein (GenBank Accession No. AAN03855)<br>(SEQ ID NO: 7)<br>  1 MAADGYLPDW LEDNLSEGIR EWWDLKPGAP KPKANQQKQD NGRGLVLPGY KYLGPENGLD<br> 61 KGEPVNAADA AALEHDKAYD QQLKAGDNPY LRYNHADAEF QERLQEDTSF GGNLGRAVEQ<br>121 AKKRVLEPLG LVEEGAKTAP AKKRPVEPSP QRSPDSSTGI GKKGQQPARK RLNFGQTGDS<br>181 ESVPDPQPLG EPPAAPSSVG SGTVAAGGGA PMADNNEGAD GVGNASGNWH CDSTWLGDRV<br>241 ITTSTRTWAL PTYNNHLYKQ ISSETAGSTN DNTYFGYSTP WGYFDENRFH CHESPRDWQR<br>301 LINNNWGFRP KKLRFKLENI QVKEVTTNDG VTTIANNLTS TIQVESDSEY QLPYVLGSAH<br>361 QGCLPPFPAD VEMIPQYGYL TLNNGSQSVG RSSFYCLEYF PSQMLRTGNN FEFSYSFEDV<br>421 PFHSSYAHSQ SLDRLMNPLI DQYLYYLART QSNPGGTAGN RELQFYQGGP STMAEQAKNW<br>481 LPGPCFRQQR VSKTLDQNNN SNFAWTGATK YHLNGRNSLV NPGVAMATHK DDEDREFPSS<br>541 GVLIFGKTGA TNKTTLENVL MTNEEEIRPT NPVATEEYGI VSSNLQAANT AAQTQVVNNQ |

| SEQUENCES |
|---|

```
601 GALPGMVWQN RDVYLQGPIW AKIPHTDGNF HPSPLMGGFG LKHPPPQILI KNTPVPANPP

661 EVFTPAKFAS FITQYSTGQV SVEIEWELQK ENSKRWNPEI QYTSNFEKQT GVDFAVDSQG

721 VYSEPRPIGT RYLTRNL
```

AAV8 capsid protein (GenBank Accession No. AAN03857)
(SEQ ID NO: 8)
```
  1 MAADGYLPDW LEDNLSEGIR EWWALKPGAP KPKANQQKQD DGRGLVLPGY KYLGPENGLD

61 KGEPVNAADA AALEHDKAYD QQLQAGDNPY LRYNHADAEF QERLQEDTSF GGNLGRAVEQ

121 AKKRVLEPLG LVEEGAKTAP GKKRPVEPSP QRSPDSSTGI GKKGQQPARK RLNFGQTGDS

181 ESVPDPQPLG EPPAAPSGVG PNTMAAGGGA PMADNNEGAD GVGSSSGNWH CDSTWLGDRV

241 ITTSTRTWAL PTYNNHLYKQ ISNGTSGGAT NDNTYFGYST PWGYEDENRF HCHFSPRDWQ

301 RLINNNWGFR PKRLSFKLEN IQVKEVTQNE GTKTIANNLT STIQVFTDSE YQLPYVLGSA

361 HQGCLPPFPA DVEMIPQYGY LTLNNGSQAV GRSSFYCLEY FPSQMLRTGN NFQFTYTFED

421 VPFHSSYAHS QSLDRLMNPL IDQYLYYLSR TQTTGGTANT QTLGFSQGGP NTMANQAKNW

481 LPGPCYRQQR VSTTTGQNNN SNFAWTAGTK YHLNGRNSLA NPGIAMATHK DDEERFFPSN

541 GILIFGKQNA ARDNADYSDV MLTSEEEIKT TNPVATEEYG IVADNLQQQN TAPQIGTVNS

601 QGALPGMVWQ NRDVYLQGPI WAKIPHTDGN FHPSPLMGGF GLKHPPPQIL IKNTPVPADP

661 PTTENQSKLN SFITQYSTGQ VSVEIEWELQ KENSKRWNPE IQYTSNYYKS TSVDFAVNTE

721 GVYSEPRPIG TRYLTRNL
```

AAV9 capsid protein (GenBank Accession No. AAS99264)
(SEQ ID NO: 9)
```
  1 MAADGYLPDW LEDNLSEGIR EWWALKPGAP QPKANQQHQD NARGLVLPGY KYLGPGNGLD

61 KGEPVNAADA AALEHDKAYD QQLKAGDNPY LKYNHADAEF QERLKEDTSF GGNLGRAVEQ

121 AKKRLLEPLG LVEEAAKTAP GKKRPVEQSP QEPDSSAGIG KSGAQPAKKR LNFGQTGDTE

181 SVPDPQPIGE PPAAPSGVGS LTMASGGGAP VADNNEGADG VGSSSGNWHC DSQWLGDRVI

241 TTSTRTWALP TYNNHLYKQI SNSTSGGSSN DNAYFGYSTP WGYFDENRFH CHESPRDWQR

301 LINNNWGFRP KRLNFKLENI QVKEVTDNNG VKTIANNLTS TVQVFTDSDY QLPYVLGSAH

361 EGCLPPFPAD VEMIPQYGYL TLNDGSQAVG RSSFYCLEYF PSQMLRTGNN FQFSYEFENV

421 PFHSSYAHSQ SLDRLMNPLI DQYLYYLSKT INGSGQNQQT LKFSVAGPSN MAVQGRNYIP

481 GPSYRQQRVS TTVTQNNNSE FAWPGASSWA LNGRNSLMNP GPAMASHKEG EDRFFPLSGS

541 LIFGKQGTGR DNVDADKVMI TNEEEIKTTN PVATESYGQV ATNHQSAQAQ AQTGWVQNQG

601 ILPGMVWQDR DVYLQGPIWA KIPHTDGNFH PSPLMGGFGM KHPPPQILIK NTPVPADPPT

661 AFNKDKLNSF ITQYSTGQVS VEIEWELQKE NSKRWNPEIQ YTSNYYKSNN VEFAVNTEGV

721 YSEPRPIGTR YLTRNL
```

AAVrh.8 capsid protein (GenBank Accession No. AA088183)
(SEQ ID NO: 10)
```
  1 MAADGYLPDW LEDNLSEGIR EWWDLKPGAP KPKANQQKQD DGRGLVLPGY KYLGPENGLD

61 KGEPVNAADA AALEHDKAYD QQLKAGDNPY LRYNHADAEF QERLQEDTSF GGNLGRAVEQ

121 AKKRVLEPLG LVEEGAKTAP GKKRPVEQSP QEPDSSSGIG KTGQQPAKKR LNFGQTGDSE

181 SVPDPQPLGE PPAAPSGLGP NTMASGGGAP MADNNEGADG VGNSSGNWHC DSTWLGDRVI

241 TTSTRTWALP TYNNHLYKQI SNGTSGGSTN DNTYFGYSTP WGYFDENRFH CHESPRDWQR

301 LINNNWGFRP KRLNFKLFNI QVKEVTTNEG TKTIANNLTS TVQVFTDSEY QLPYVLGSAH
```

| SEQUENCES |
| --- |
| 361 QGCLPPFPAD VFMVPQYGYL TLNNGSQALG RSSFYCLEYF PSQMLRTGNN FQFSYTFEDV |
| 421 PFHSSYAHSQ SLDRLMNPLI DQYLYYLVRT QTTGTGGTQT LAFSQAGPSS MANQARNWVP |
| 481 GPCYRQQRVS TTTNQNNNSN FAWTGAAKFK LNGRDSLMNP GVAMASHKDD DDRFFPSSGV |
| 541 LIFGKQGAGN DGVDYSQVLI TDEEEIKATN PVATEEYGAV AINNQAANTQ AQTGLVHNQG |
| 601 VIPGMVWQNR DVYLQGPIWA KIPHTDGNFH PSPLMGGFGL KHPPPQILIK NTPVPADPPL |
| 661 TFNQAKLNSF ITQYSTGQVS VEIEWELQKE NSKRWNPEIQ YTSNYYKSTN VDFAVNTEGV |
| 721 YSEPRPIGTR YLTRNL |
| AAVrh. 10 capsid protein (GenBank Accession No. AAO88201) |
| (SEQ ID NO: 11) |
| 1 MAADGYLPDW LEDNLSEGIR EWWDLKPGAP KPKANQQKQD DGRGLVLPGY KYLGPENGLD |
| 61 KGEPVNAADA AALEHDKAYD QQLKAGDNPY LRYNHADAEF QERLQEDTSF GGNLGRAVEQ |
| 121 AKKRVLEPLG LVEEGAKTAP GKKRPVEPSP QRSPDSSTGI GKKGQQPAKK RLNFGQTGDS |
| 181 ESVPDPQPIG EPPAGPSGLG SGTMAAGGGA PMADNNEGAD GVGSSSGNWH CDSTWLGDRV |
| 241 ITTSTRTWAL PTYNNHLYKQ ISNGTSGGST NDNTYFGYST PWGYEDENRF HCHESPRDWQ |
| 301 RLINNNWGFR PKRLNFKLEN IQVKEVTQNE GTKTIANNLT STIQVFTDSE YQLPYVLGSA |
| 361 HQGCLPPFPA DVEMIPQYGY LTLNNGSQAV GRSSFYCLEY FPSQMLRTGN NFEFSYQFED |
| 421 VPFHSSYAHS QSLDRLMNPL IDQYLYYLSR TQSTGGTAGT QQLLESQAGP NNMSAQAKNW |
| 481 LPGPCYRQQR VSTTLSQNNN SNFAWTGATK YHLNGRDSLV NPGVAMATHK DDEERFFPSS |
| 541 GVLMFGKQGA GKDNVDYSSV MLTSEEEIKT TNPVATEQYG VVADNLQQQN AAPIVGAVNS |
| 601 QGALPGMVWQ NRDVYLQGPI WAKIPHTDGN FHPSPLMGGF GLKHPPPQIL IKNTPVPADP |
| 661 PTTESQAKLA SFITQYSTGQ VSVEIEWELQ KENSKRWNPE IQYTSNYYKS TNVDFAVNTD |
| 721 GTYSEPRPIG TRYLTRNL |
| AAV10 capsid protein (GenBank Accession No. AAT46337) |
| (SEQ ID NO: 12) |
| 1 MAADGYLPDW LEDNLSEGIR EWWDLKPGAP KPKANQQKQD DGRGLVLPGY KYLGPENGLD |
| 61 KGEPVNAADA AALEHDKAYD QQLKAGDNPY LRYNHADAEF QERLQEDTSF GGNLGRAVEQ |
| 121 AKKRVLEPLG LVEEAAKTAP GKKRPVEPSP QRSPDSSTGI GKKGQQPAKK RLNFGQTGES |
| 181 ESVPDPQPIG EPPAGPSGLG SGTMAAGGGA PMADNNEGAD GVGSSSGNWH CDSTWLGDRV |
| 241 ITTSTRTWAL PTYNNHLYKQ ISNGTSGGST NDNTYFGYST PWGYFDENRF HCHFSPRDWQ |
| 301 RLINNNWGFR PKRLSFKLEN IQVKEVTQNE GTKTIANNLT STIQVFTDSE YQLPYVLGSA |
| 361 HQGCLPPFPA DVEMIPQYGY LTLNNGSQAV GRSSFYCLEY FPSQMLRTGN NFEFSYTFED |
| 421 VPFHSSYAHS QSLDRLMNPL IDQYLYYLSR TQSTGGTQGT QQLLESQAGP ANMSAQAKNW |
| 481 LPGPCYRQQR VSTTLSQNNN SNFAWTGATK YHLNGRDSLV NPGVAMATHK DDEERFFPSS |
| 541 GVLMFGKQGA GRDNVDYSSV MLTSEEEIKT TNPVATEQYG VVADNLQQAN TGPIVGNVNS |
| 601 QGALPGMVWQ NRDVYLQGPI WAKIPHTDGN FHPSPLMGGF GLKHPPPQIL IKNTPVPADP |
| 661 PTTESQAKLA SFITQYSTGQ VSVEIEWELQ KENSKRWNPE IQYTSNYYKS TNVDFAVNTE |
| 721 GTYSEPRPIG TRYLTRNL |
| AAV11 capsid protein (GenBank Accession No. AAT46339) |
| (SEQ ID NO: 13) |
| 1 MAADGYLPDW LEDNLSEGIR EWWDLKPGAP KPKANQQKQD DGRGLVLPGY KYLGPENGLD |
| 61 KGEPVNAADA AALEHDKAYD QQLKAGDNPY LRYNHADAEF QERLQEDTSF GGNLGRAVEQ |
| 121 AKKRVLEPLG LVEEGAKTAP GKKRPLESPQ EPDSSSGIGK KGKQPARKRL NFEEDTGAGD |

| SEQUENCES |
|---|

```
181 GPPEGSDTSA MSSDIEMRAA PGGNAVDAGQ GSDGVGNASG DWHCDSTWSE GKVTTTSTRT

241 WVLPTYNNHL YLRLGTTSSS NTYNGESTPW GYFDENRFHC HESPRDWQRL INNNWGLRPK

301 AMRVKIFNIQ VKEVTTSNGE TTVANNLTST VQIFADSSYE LPYVMDAGQE GSLPPFPNDV

361 FMVPQYGYCG IVTGENQNQT DRNAFYCLEY FPSQMLRTGN NFEMAYNFEK VPFHSMYAHS

421 QSLDRLMNPL LDQYLWHLQS TTSGETLNQG NAATTFGKIR SGDFAFYRKN WLPGPCVKQQ

481 RESKTASQNY KIPASGGNAL LKYDTHYTLN NRWSNIAPGP PMATAGPSDG DESNAQLIFP

541 GPSVTGNTTT SANNLLFTSE EEIAATNPRD TDMFGQIADN NQNATTAPIT GNVTAMGVLP

601 GMVWQNRDIY YQGPIWAKIP HADGHFHPSP LIGGFGLKHP PPQIFIKNTP VPANPATTET

661 AARVDSFITQ YSTGQVAVQI EWEIEKERSK RWNPEVQFTS NYGNQSSMLW APDTTGKYTE

721 PRVIGSRYLT NHL
```

AAV12 capsid protein (GenBank Accession No. ABI16639)
(SEQ ID NO: 14)
```
  1 MAADGYLPDW LEDNLSEGIR EWWALKPGAP QPKANQQHQD NGRGLVLPGY KYLGPENGLD

61 KGEPVNEADA AALEHDKAYD KQLEQGDNPY LKYNHADAEF QQRLATDTSF GGNLGRAVEQ

121 AKKRILEPLG LVEEGVKTAP GKKRPLEKTP NRPTNPDSGK APAKKKQKDG EPADSARRTL

181 DEEDSGAGDG PPEGSSSGEM SHDAEMRAAP GGNAVEAGQG ADGVGNASGD WHCDSTWSEG

241 RVTTTSTRTW VLPTYNNHLY LRIGTTANSN TYNGESTPWG YEDENRFHCH FSPRDWQRLI

301 NNNWGLRPKS MRVKIFNIQV KEVTTSNGET TVANNLTSTV QIFADSTYEL PYVMDAGQEG

361 SFPPFPNDVF MVPQYGYCGV VTGKNQNQTD RNAFYCLEYF PSQMLRTGNN FEVSYQFEKV

421 PFHSMYAHSQ SLDRMMNPLL DQYLWHLQST TTGNSLNQGT ATTTYGKITT GDFAYYRKNW

481 LPGACIKQQK FSKNANQNYK IPASGGDALL KYDTHTTLNG RWSNMAPGPP MATAGAGDSD

541 FSNSQLIFAG PNPSGNTTTS SNNLLFTSEE EIATTNPRDT DMFGQIADNN QNATTAPHIA

601 NLDAMGIVPG MVWQNRDIYY QGPIWAKVPH TDGHFHPSPL MGGFGLKHPP PQIFIKNTPV

661 PANPNTTESA ARINSELTQY STGQVAVQID WEIQKEHSKR WNPEVQFTSN YGTQNSMLWA

721 PDNAGNYHEL RAIGSRELTH HL
```

AAVrh.32.33 capsid protein (GenBank Accession No. ACB55318)
(SEQ ID NO: 15)
```
  1 MAADGYLPDW LEDNLSEGIR EWWDLKPGAP KPKANQQKQD DGRGLVLPGY KYLGPENGLD

61 KGEPVNAADA AALEHDKAYD QQLKAGDNPY LRYNHADAEF QERLQEDTSF GGNLGRAVEQ

121 AKKRVLEPLG LVEEGAKTAP GKKRPLESPQ EPDSSSGIGK KGKQPAKKRL NFEEDTGAGD

181 GPPEGSDTSA MSSDIEMRAA PGGNAVDAGQ GSDGVGNASG DWHCDSTWSE GKVTTTSTRT

241 WVLPTYNNHL YLRLGTTSNS NTYNGESTPW GYFDFNRFHC HESPRDWQRL INNNWGLRPK

301 AMRVKIFNIQ VKEVTTSNGE TTVANNLTST VQIFADSSYE LPYVMDAGQE GSLPPFPNDV

361 FMVPQYGYCG IVTGENQNQT DRNAFYCLEY FPSQMLRTGN NFEMAYNFEK VPFHSMYAHS

421 QSLDRLMNPL LDQYLWHLQS TTSGETLNQG NAATTFGKIR SGDFAFYRKN WLPGPCVKQQ

481 RFSKTASQNY KIPASGGNAL LKYDTHYTLN NRWSNIAPGP PMATAGPSDG DESNAQLIFP

541 GPSVTGNTTT SANNLLFTSE EEIAATNPRD TDMFGQIADN NQNATTAPIT GNVTAMGVLP

601 GMVWQNRDIY YQGPIWAKIP HADGHFHPSP LIGGFGLKHP PPQIFIKNTP VPANPATTFT

661 AARVDSFITQ YSTGQVAVQI EWEIEKERSK RWNPEVQFTS NYGNQSSMLW APDTTGKYTE

721 PRVIGSRYLT NHL
```

SEQUENCES

AAV capsid protein (GenBank Accession No. YP_024971)
(SEQ ID NO: 16)

```
  1 MSFVDHPPDW LESIGDGFRE FLGLEAGPPK PKANQQKQDN ARGLVLPGYK YLGPGNGLDK
 61 GDPVNFADEV AREHDLSYQK QLEAGDNPYL KYNHADAEFQ EKLASDTSFG GNLGKAVFQA
121 KKRILEPLGL VETPDKTAPA AKKRPLEQSP QEPDSSSGVG KKGKQPARKR LNEDDE PGAG
181 DGPPPEGPSS GAMSTETEMR AAAGGNGGDA GQGAEGVGNA SGDWHCDSTW SESHVTTTST
241 RTWVLPTYNN HLYLRLGSSN ASDTENGEST PWGYEDENRF HCHESPRDWQ RLINNHWGLR
301 PKSMQVRIEN IQVKEVTTSN GETTVSNNLT STVQIFADST YELPYVMDAG QEGSLPPEPN
361 DVFMVPQYGY CGLVTGGSSQ NQTDRNAFYC LEYFPSQMLR TGNNFEMVYK FENVPFHSMY
421 AHSQSLDRLM NPLLDQYLWE LQSTTSGGTL NQGNSATNFA KLTKTNESGY RKNWLPGPMM
481 KQQRESKTAS QNYKIPQGRN NSLLHYETRT TLDGRWSNFA PGTAMATAAN DATDESQAQL
541 IFAGPNITGN TTTDANNLMF TSEDELRATN PRDTDLFGHL ATNQQNATTV PTVDDVDGVG
601 VYPGMVWQDR DIYYQGPIWA KIPHTDGHFH PSPLIGGEGL KSPPPQIFIK NTPVPANPAT
661 TESPARINSF ITQYSTGQVA VKIEWEIQKE RSKRWNPEVQ FTSNYGAQDS LLWAPDNAGA
721 YKEPRAIGSR YLTNHL
```

AAV ATCC VR-865 capsid protein (GenBank Accession No. NP_852781)
(SEQ ID NO: 17)

```
  1 MSLISDAIPD WLERLVKKGV NAAADFYHLE SGPPRPKANQ QTQESLEKDD SRGLVFPGYN
 61 YLGPENGLDK GEPVNEADAA ALEHDKAYDL EIKDGHNPYF EYNEADRRFQ ERLKDDTSFG
121 GNLGKAIFQA KKRVLEPFGL VEDSKTAPTG DKRKGEDEPR LPDTSSQTPK KNKKPRKERP
181 SGGAEDPGEG TSSNAGAAAP ASSVGSSIMA EGGGGPVGDA GQGADGVGNS SGNWHCDSQW
241 LENGVVTRTT RTWVLPSYNN HLYKRIQGPS GGDNNNKFFG FSTPWGYEDY NRFHCHESPR
301 DWQRLINNNW GIRPKAMRER LFNIQVKEVT VQDENTTIGN NLTSTVQVFA DKDYQLPYVL
361 GSATEGTFPP FPADIYTIPQ YGYCTLNYNN EAVDRSAFYC LDYFPSDMLR TGNNFEFTYT
421 FEDVPFHSMF AHNQTLDRLM NPLVDQYLWA FSSVSQAGSS GRALHYSRAT KTNMAAQYRN
481 WLPGPFFRDQ QIFTGASNIT KNNVFSVWEK GKQWELDNRT NLMQPGAAA TTESGEPDRQ
541 AMQNTLAFSR TVYDQTTATT DRNQILITNE DEIRPTNSVG IDAWGAVPTN NQSIVTPGTR
601 AAVNNQGALP GMVWQNRDIY PTGTHLAKIP DTDNHFHPSP LIGRFGCKHP PPQIFIKNTP
661 VPANPSETFQ TAKVASFINQ YSTGQCTVEI FWELKKETSK RWNPEIQFTS NFGNAADIQF
721 AVSDTGSYSE PRPIGTRYLT KPL
```

Example of AAV1 VP1 Capsid Protein Sequence

```
  1 maadgylpdw lednlsegir ewwdlkpgap kpkanqqkqd dgrglvlpgy
 51 kylgpfngld kgepvnaada aalehdkayd qqlkagdnpy lrynhadaef
101 gerlqedtsf ggnlgravfq akkrvleplg lveegaktap gkkrpveqsp
151 gepdsssgig ktgqqpakkr lnfgqtgdse svpdpqplge ppatpaavgp
201 ttmasgggap madnnegadg vgnasgnwhc dstwlgdrvi ttstrtwalp
251 tynnhlykqi ssastgasnd nhyfgystpw gyfdfnrfhc hfsprdwqrl
301 innnwgfrpk rlnfklfniq vkevttndgv ttianniltst vqvfsdseyq
351 lpyvlgsahq gclppfpadv fmipqygylt lnngsqavgr ssfycleyfp
401 sqmlrtgnnf tfsytfeevp fhssyahsgs ldrlmnplid qylyylnrtq
451 nqsgsagnkd llfsrgspag msvqpknwlp gpcyrqqrvs ktktdnnnsn
501 ftwtgaskyn lngresiinp gtamashkdd edkffpmsgv mifgkesaga
551 sntaldnvmi tdeeeikatn pvaterfgtv avnfqssstd patgdvhamg
601 alpgmvwqdr dvylqgpiwa kiphtdghfh psplmggfgl knpppgilik
651 ntpvpanpPA EFSATKFAsf itqystgqvs veiewelqke nskrwnpevq
701 ytsnyaksan vdftvdnngl yteprpigtr yltrpl (SEQ ID NO:18)
```

Example of AAV2 VP1 capsid protein sequence

```
  1 maadgylpdw ledtlsegir qwwklkpgpp ppkpaerhkd dsrglvlpgy
```

51 kylgpfngld kgepvneada aalehdkayd rqldsgdnpy lkyn-
hadaef
101 gerlkedtsf ggnlgravfq akkrvleplg lveepvktap
gkkrpvehsp
151 vepdsssgtg kagqqparkr lnfgqtgdad svpdpqplgq
ppaapsglgt
201 ntmatgsgap madnnegadg vgnssgnwhc dstwmgdrvi
ttstrtwalp
251 tynnhlykqi ssqsgasndn hyfgystpwg yfdfnrfhch
fsprdwqrli
301 nnnwgfrpkr lnfklfniqv kevtqndgtt tiannltstv qvftd-
seyql
351 pyvlgsahqg clppfpadvf mvpqygyltl nngsqavgrs sfy-
cleyfps
401 qmlrtgnnft fsytfedvpf hssyahsqsl drlmnplidq
ylyylsrtnt
451 psgtttqsrl qfsqagasdi rdqsrnwlpg pcyrqqrvsk tsadnnn-
sey
501 swtgatkyhl ngrdslvnpg pamashkdde ekffpqsgvl
ifgkqgsekt
551 nvdiekvmit deeeirttnp vategygsvs tnlqrgnrqa atad-
vntqgv
601 lpgmvwqdrd vylqgpiwak iphtdghfhp splmggfglk
hpppgilikn
651 tpvpanpSTT FSAAKFAsfi tqystgqvsv eiewelqken
skrwnpeiqy
701 tsnynksvnv dftvdtngvy seprpigtry ltrnl (SEQ ID
NO:19)

Example of AAV3 VP1 capsid protein sequence
1 maadgylpdw lednlsegir ewwwalkpgvp qpkanqqhqd nrr-
glvlpgy
51 kylgpgngld kgepvneada aalehdkayd qqlkagdnpy lkyn-
hadaef
101 gerlqedtsf ggnlgravfq akkrileplg lveeaaktap gkk-
gavdqsp
151 gepdsssgvg ksgkqparkr lnfgqtgdse svpdpqplge
ppaaptsIgs
201 ntmasgggap madnnegadg vgnssgnwhc dsqwlgdrvi
ttstrtwalp
251 tynnhlykqi ssqsgasndn hyfgystpwg yfdfnrfhch
fsprdwqrli
301 nnnwgfrpkk lsfklfniqv rgvtqndgtt tiannltstv qvftd-
seyql
351 pyvlgsahqg clppfpadvf mvpqygyltl nngsqavgrs sfy-
cleyfps
401 qmlrtgnnfq fsytfedvpf hssyahsqsl drlmnplidq
ylyylnrtqg
451 ttsgttnqsr llfsqagpqs mslqarnwlp gpcyrqqrls
ktandnnnsn
501 fpwtaaskyh ingrdslvnp gpamashkdd eekffpmhgn
lifgkegtta
551 snaeldnvmi tdeeeirttn pvateqygtv annlqssnta
pttgtvnhqg
601 alpgmvwqdr dvylqgpiwa kiphtdghfh psplmggfgl
khpppgimik
651 ntpvpanpPT TFSPAKFAsf itqystgqvs veiewelqke
nskrwnpeiq
701 ytsnynksvn vdftvdtngv yseprpigtr yltrnl (SEQ ID
NO:20)

Example of AAV4 VP1 capsid protein sequence
1 mtdgylpdwl ednlsegvre wwalqpgapk pkanqqhqdn
arglvlpgyk
51 ylgpgngldk gepvnaadaa alehdkaydq qlkagdnpyl kyn-
hadaefq
101 grlqgdtsfg gnlgravfqa kkrvleplgl veqagetapg kkr-
pliespq 151 qpdsstgigk kgkqpakkkl vfedetgagd gppegstsga msdd-
semraa
201 aggaaveggq gadgvgnasg dwhcdstwse ghvtttstrt wvlp-
tynnhl
251 ykrlgeslqs ntyngfstpw gyfdfnrfhc hfsprdwqrl
innnwgmrpk
301 amrvkifniq vkevttsnge ttvannltst vqifadssye lpyvm-
dagqe
351 gslppfpndv fmvpqygycg lvtgntsqqq tdrnafycle yfp-
sqmlrtg
401 nnfeitysfe kvpfhsmyah sqsldrlmnp lidqylwglq stttgt-
tlna
451 gtattnftkl rptnfsnfkk nwlpgpsikq qgfsktangn yki-
patgsds
501 likyethstl dgrwsaltpg ppmatagpad skfsnsqlif
agpkqngnta
551 tvpgtlifts eeelaatnat dtdmwgnlpg gdqsnsnlpt vdrltal-
gav
601 pgmvwqnrdi yyqgpiwaki phtdghfhps pliggfglkh ppp-
gifiknt
651 pvpanpATTF SSTPVNsfit qystgqvsvq idweiqkers
krwnpevqft
701 snygqqnsll wapdaagkyt epraigtryl thhl (SEQ ID
NO:21)

Example of AAV5 VP1 capsid protein sequence
1 msfvdhppdw leevgeglre flgleagppk pkpnqqhqdq
arglvlpgyn
51 ylgpgngldr gepvnradev arehdisyne qleagdnpyl kynha-
daefq
101 ekladdtsfg gnlgkavfqa kkrvlepfgl veegaktapt gkrid-
dhfpk
151 rkkarteeds kpstssdaea gpsgsqqlqi paqpasslga dtm-
sagggp
201 lgdnnqgadg vgnasgdwhc dstwmgdrvv tkstrtwvlp syn-
nhqyrei
251 ksgsvdgsna nayfgystpw gyfdfnrfhs hwsprdwqrl
innywgfrpr
301 slrvkifniq vkevtvqdst ttiannltst vqvftdddyq
lpyvvgngte
351 gclpafppqv ftlpqygyat lnrdntenpt erssffcley
fpskmlrtgn
401 nfeftynfee vpfhssfaps qnlfklanpl vdqylyrfvs
tnntggvqfn
451 knlagryant yknwfpgpmg rtqgwnlgsg vnrasvsafa
ttnrmelega
501 syqvppqpng mtnnlqgsnt yalentmifn sqpanpgtta
tylegnmlit
551 sesetqpvnr vaynvggqma tnnqssttap atgtynlgei
vpgsvwmerd
601 vylqgpiwak ipetgahfhp spamggfglk hpppmmlikn
tpvpgniTSF
651 SDVPVSsfit qystgqvtve mewelkkens krwnpeigyt
nnyndpqfvd
701 fapdstgeyr ttrpigtryl trpl (SEQ ID NO:22)

Example of AAV6 VP1 capsid protein sequence
1 maadgylpdw lednlsegir ewwwdlkpgap kpkanqqkqd dgr-
glvlpgy
51 kylgpfngld kgepvnaada aalehdkayd qqlkagdnpy lryn-
hadaef
101 gerlqedtsf ggnlgravfq akkrvlepfg lveegaktap
gkkrpveqsp
151 gepdsssgig ktgqqpakkr lnfgqtgdse svpdpqplge ppat-
paavgp
201 ttmasgggap madnnegadg vgnasgnwhc dstwlgdrvi
ttstrtwalp
251 tynnhlykqi ssastgasnd nhyfgystpw gyfdfnrfhc
hfsprdwqrl

```
301 innnwgfrpk rlnfklfniq vkevttndgv ttianlltst vqvfsd-
    seyq
351 lpyvlgsahq gclppfpadv fmipqygylt lnngsqavgr ssfy-
    cleyfp
401 sqmlrtgnnf tfsytfedvp fhssyahsgs ldrlmnplid
    qylyylnrtq
451 nqsgsagnkd llfsrgspag msvqpknwlp gpcyrqqrvs
    ktktdnnnsn
501 ftwtgaskyn lngresiinp gtamashkdd kdkffpmsgv
    mifgkesaga
551 sntaldnvmi tdeeeikatn pvaterfgtv avnlqssstd
    patgdvhvmg
601 alpgmvwqdr dvylqgpiwa kiphtdghfh psplmggfgl
    khpppgilik
651 ntpvpanpPA EFSATKFAsf itqystgqvs veiewelqke
    nskrwnpevq
701 ytsnyaksan vdftvdnngl yteprpigtr yltrpl (SEQ ID
    NO:23)
```
Example of AAV7 VP1 capsid protein sequence
```
  1 maadgylpdw lednlsegir ewwdlkpgap kpkanqqkqd ngr-
    glvlpgy
 51 kylgpfngld kgepvnaada aalehdkayd qqlkagdnpy lryn-
    hadaef
101 gerlqedtsf ggnlgravfq akkrvleplg lveegaktap
    akkrpvepsp
151 grspdsstgi gkkgqqpark rlnfgqtgds esvpdpqplg
    eppaapssvg
201 sgtvaaggga pmadnnegad gvgnasgnwh cdstwlgdrv
    ittstrtwal
251 ptynnhlykq issetagstn dntyfgystp wgyfdfnrfh
    chfsprdwqr
301 linnnwgfrp kklrfklfni qvkevttndg vttiannlts tiqvfsd-
    sey
351 qlpyvlgsah qgclppfpad vfmipqygyl tlnngsqsvg rssfy-
    cleyf
401 psqmlrtgnn fefsysfedv pfhssyahsq sldrlmnpli dqylyy-
    lart
451 qsnpggtagn relqfyqggp stmaeqaknw lpgpcfrqqr
    vsktldqnnn
501 snfawtgatk yhlngrnslv npgvamathk ddedrffpss
    gvlifgktga
551 tnkttlenvl mtneeeirpt npvateeygi vssnlqaant
    aaqtqvvnnq
601 galpgmvwqn rdvylqgpiw akiphtdgnf hpsplmggfg
    lkhpppgili
651 kntpvpanpP EVFTPAKFAs fitqystgqv sveiewelqk
    enskrwnpei
701 qytsnfekqt gvdfavdsqg vyseprpigt ryltrnl (SEQ ID
    NO:24)
```
Example of AAV8 VP1 capsid protein sequence
```
  1 maadgylpdw lednlsegir ewwalkpgap kpkanqqkqd dgr-
    glvlpgy
 51 kylgpfngld kgepvnaada aalehdkayd qqlqagdnpy lryn-
    hadaef
101 gerlqedtsf ggnlgravfq akkrvleplg lveegaktap
    gkkrpvepsp
151 grspdsstgi gkkgqqpark rlnfgqtgds esvpdpqplg
    eppaapsgvg
201 pntmaaggga pmadnnegad gvgsssgnwh cdstwlgdrv
    ittstrtwal
251 ptynnhlykq isngtsggat ndntyfgyst pwgyfdfnrf
    hchfsprdwq
301 rlinnnwgfr pkrlsfklfn iqvkevtqne gtktiannlt stiqvftdse
351 yqlpyvlgsa hqgclppfpa dvfmipqygy ltlnngsgav
    grssfycley
401 fpsqmlrtgn nfqftytfed vpfhssyahs qsldrlmnpl idqy-
    lyylsr
```
```
451 tqttggtant qtlgfsqggp ntmangaknw lpgpcyrqqr
    vstttgqnnn
501 snfawtagtk yhlngrnsla npgiamathk ddeerffpsn gil-
    ifgkqna
551 ardnadysdv mltseeeikt tnpvateeyg ivadnlqqqn tapqi-
    gtvns
601 qgalpgmvwq nrdvylqgpi wakiphtdgn fhpsplmggf
    glkhpppgil
651 ikntpvpadp PTTFNQSKLN sfitqystgq vsveiewelq
    kenskrwnpe
701 igytsnyyks tsvdfavnte gvyseprpig tryltrnl (SEQ ID
    NO:25)
```
Example of AAV9 VP1 capsid protein sequence
```
  1 maadgylpdw lednlsegir ewwalkpgap qpkanqqhqd nar-
    glvlpgy
 51 kylgpgngld kgepvnaada aalehdkayd qqlkagdnpy lkyn-
    hadaef
101 gerlkedtsf ggnlgravfq akkrlleplg lveeaaktap
    gkkrpveqsp
151 gepdssagig ksgaqpakkr lnfgqtgdte svpdpqpige
    ppaapsgvgs
201 ltmasgggap vadnnegadg vgsssgnwhc dsqwlgdrvi
    ttstrtwalp
251 tynnhlykqi snstsggssn dnayfgystp wgyfdfnrfh
    chfsprdwqr
301 linnnwgfrp krlnfklfni qvkevtdnng vktiannlts
    tvqvftdsdy
351 qlpyvlgsah egclppfpad vfmipqygyl tlndgsqavg rssfy-
    cleyf
401 psqmlrtgnn fqfsyefenv pfhssyahsq sldrlmnpli dqy-
    lyylskt
451 ingsgqnqqt lkfsvagpsn mavqgmyip gpsyrqqrvs
    ttvtqnnnse
501 fawpgasswa lngmslmnp gpamashkeg edrffplsgs
    lifgkqgtgr
551 dnvdadkvmi tneeeikttn pvatesygqv atnhqsaqaq
    aqtgwvqnqg
601 ilpgmvwqdr dvylqgpiwa kiphtdgnfh psplmggfgm
    khpppgilik
651 ntpvpadpPTAFNKDKLNsf itqystgqvs veiewelqke
    nskrwnpeiq
701 ytsnyyksnn vefavntegv yseprpigtr yltrnl (SEQ ID
    NO:26)
```
Example of AAV10 VP1 capsid protein sequence
```
  1 maadgylpdw lednlsegir ewwdlkpgap kpkanqqkqd dgr-
    glvlpgy
 51 kylgpfngld kgepvnaada aalehdkayd qqlkagdnpy lryn-
    hadaef
101 gerlqedtsf ggnlgravfq akkrvleplg lveegaktap
    gkkrpvepsp
151 grspdsstgi gkkgqqpakk rlnfgqtgds esvpdpqpig
    eppagpsglg
201 sgtmaaggga pmadnnegad gvgsssgnwh cdstwlgdrv
    ittstrtwal
251 ptynnhlykq isngtsggst ndntyfgyst pwgyfdfnrf
    hchfsprdwq
301 rlinnnwgfr pkrlnfklfn iqvkevtqne gtktiannlt stiqvftdse
351 yqlpyvlgsa hqgclppfpa dvfmipqygy ltlnngsqav
    grssfycley
401 fpsqmlrtgn nfefsyqfed vpfhssyahs qsldrlmnpl idqy-
    lyylsr
451 tqstggtagt qqllfsqagp nnmsaqaknw lpgpcyrqqr vst-
    tlsqnnn
501 snfawtgatk yhlngrdslv npgvamathk ddeerffpss
    gvlmfgkqga
551 gkdnvdyssv mltseeeikt tnpvateqyg vvadnlqqqn
    aapivgavns
```

601 qgalpgmvwq nrdvylqgpi wakiphtdgn fhpsplmggf glkhpppgil
651 ikntpvpadp PTTFSQAKLA sfitqystgq vsveiewelq kenskrwnpe
701 igytsnyyks tnvdfavntd gtyseprpig tryltml (SEQ ID NO:27)

Example of AAV 11 VP1 capsid protein sequence maadgylpdwlednlsegirewwdlkpgapkpkanqqkqddgr-glvlpgykylgpfngldkgepvnaadaaalehdkayd qqlk-agdnpylrynhadaefqerlqedtsfggnlgravfqakkrvle-plglveegaktapgkkrplespqepdsssgigkkgkqp arkrlnfeedtgagdgppegsdtsamssdiemraapgg-navdagqgsdgvgnasgdwhcdstwsegkvtttstrtwvlptynn hlylrlgttsssntyngfstpwgyfdfnrfhchfsprdwqr-linnnwglrpkamrvkifniqvkevttsngettvannltstvqifad ssyelpyvmdagqegslppfpndvfmvpqygy cgivtgenqngtdr-nafycyleyfpsqmlrtgnnfemaynfekvpfhsmy ahsgsldrlmn-plldqylwhlqsttsgetlnqgnaattfgkirsgd-fafyrknwlpgpcvkqqrfsktasqnykipasggnallky d thytlnnrwsniapgppmatagpsdgdfsnaqlifpgpsvtgnttt-sannllftseeeiaatnprdtdmfggiadnnqnattapitg nvtamgvlpgmvwqnrdiyyggpiwakiphadghfhpsp-liggfglkhpppgifikntpvpanpATTFTAAR VDsfitq ystgqvavqieweiekerskrwnpevqftsnygnqssmlwap-dttgkyteprvigsryltnhl (SEQ ID NO:28)

Example of AAV12 VP1 Capsid Protein Sequence maadgylpdwlednlsegirewwalkpgapqpkanqqhqdngr-glvlpgykylgpfngldkgepvneadaaalehdkayd kqleggdnpylkynhadaefqqrlatdtsfggnlgravfqakkrile-plglveegvktapgkkrplektpnrptnpdsgkapakkk qkdgepad-sarrtldfedsgagdgppegsssgemshdaemraapgg-naveagqgadgvgnasgdwhcdstwsegrvtttstrt wvlptynnhlylrigttansntyngfstpwgyfdfnrfhchfsprdwqr-linnnwglrpksmrvkifniqvkevttsngettvan nltstvqifad-styelpyvmdagqegsfppfpndvfmvpqygycgvvtgknqnqtdr-nafy cleyfpsqmlrtgnnfevsyqfe kvpfhsmyahsgsldrmmnplldqylwhlqstttgnslnqgtatttyg-kittgdfayyrknwlpgacikqqkfsknanqnykip asggdallky dthttlngrwsnmapgppmatagagdsdfsnsqlif-agpnpsgntttssnnllftseeeiattnprdtdmfggiad nnqnattaph-ianldamgivpgmvwqnrdiyyggpiwakvph-tdghfhpsplmggfglkhpppgifikntpvpanpNTT FSAAARINsfltqystgqvavqidweiqkehskrwnpe-vqftsnygtqnsmlwapdnagnyhelraigsrflthhl (SEQ ID NO:29)

Example of AAV13 VP1 capsid protein sequence mtdgylpdwlednlsegvrewwalqpgapkpkanqqhqdnar-glvlpgykylgpngldkgepvnaadaaalehdkaydq qlk-agdnpylkynhadaefqerlqedtsfggnlgravfqakkrileplglvee-aaktapgkkrpveqspaepdsssgigksgqqp arkrlnfgqtgdtesvpdpqplgqppaapsgvgsttmasgggap-madnneagadgvgnssgnwhcdsqwlgdrvittstrtwal ptynnh-lykqissqsgatndnhyfgystpwgyfdfnrfhchfsprdwqr-linnnwgfrpkrlnfklfniqvkevtqndetttian nltstvqvftdseyqlpyvlgsahqgclppfpadvfmvpqygyltlnng-sqavgrssfycleyfpsqmlrtgnnfqfsytfedvpf hssyahsqsl-drlmnplidqylyylnrtqtasgtqqsrllf-sqagptsmslqaknwlpgpcyrqqrlskqandnnnsnfpwtgatk yhlngrdslvnpgpamashkddkekffpmhgtlifgkegtnanna-dlenvmitdeeeirttnpvategygtvsnnlqnsnagpt tgtvnhqgalpgmvwqdrdvylqgpiwakiph-tdghfhpsplmggfglkhpppqimikntpvpanpPTNFSAAK-FAsf itqystgqvsveiewelqkenskrwn-peiqytsnynksvnvdftvdtngvyseprpigtryltrnl (SEQ ID NO:30)

---

That which is claimed is:

1. An adeno-associated virus (AAV) capsid protein, wherein the capsid protein comprises a substitution, wherein the substitution comprises the amino acid sequence of RSTFNGDKLN (hi-C: SEQ ID NO:193) at the amino acids corresponding to amino acid positions 661 to 670 of the native AAV8 capsid protein (VP1 numbering) based on the reference amino acid sequence of AAV8 identified as SEQ ID NO:8.

2. An AAV particle comprising the rAAV capsid protein of claim 1, wherein the substitution results in the AAV particle having decreased reactivity to a neutralizing antibody compared to a reference AAV particle that comprises capsid protein without the substitution.

3. The AAV particle of claim 2, wherein the neutralizing antibody is HL2372.

4. An AAV capsid comprising the AAV capsid protein of claim 1.

5. An AAV virus particle comprising the AAV capsid of claim 4.

6. A virus vector comprising:
   (a) the AAV capsid of claim 4; and
   (b) a nucleic acid comprising at least one terminal repeat sequence, wherein the nucleic acid is encapsidated by the AAV capsid.

7. The virus vector of claim 6, wherein the nucleic acid comprises a sequence encoding a therapeutic protein or therapeutic RNA.

8. The virus vector of claim 6, wherein the virus vector is immunologically distinct from its parental AAV serotype and is not recognized by antibodies that bind the parental serotype.

9. A composition comprising the AAV capsid protein of claim 1, in a pharmaceutically acceptable carrier.

10. A method of administering a nucleic acid to a cell, the method comprising contacting the cell with the virus vector of claim 6.

11. A method of delivering a nucleic acid to a subject, the method comprising administering to the subject the virus vector of claim 6.

12. The method of claim 11, wherein the subject is a human subject.

13. A polynucleotide comprising a nucleic acid sequence that encodes an AAV capsid protein, wherein the encoded AAV capsid protein comprises a substitution, wherein the substitution comprises the amino acid sequence of RSTFNGDKLN (hi-C; SEQ ID NO:193) at the amino acids corresponding to amino acid positions 661 to 670 of the native AAV8 capsid protein (VP1 numbering) based on the reference amino acid sequence of AAV8 identified as SEQ ID NO:8.

14. The polynucleotide of claim 13, wherein the polynucleotide is DNA or RNA.

15. An expression vector comprising the polynucleotide of claim 13.

16. An isolated cell comprising the polynucleotide of claim 13.

17. An in vitro method of introducing a nucleic acid molecule into a cell, comprising contacting the cell with the virus vector of claim 6.

18. A method of producing an adeno-associated virus (AAV) capsid protein, the method comprising:
   a. culturing the isolated cell of claim 16; and
   b. collecting the AAV capsid protein from the cell.

* * * * *

UNITED STATES PATENT AND TRADEMARK OFFICE
CERTIFICATE OF CORRECTION

PATENT NO. : 12,281,320 B2
APPLICATION NO. : 16/976408
DATED : April 22, 2025
INVENTOR(S) : Asokan et al.

Page 1 of 4

It is certified that error appears in the above-identified patent and that said Letters Patent is hereby corrected as shown below:

In the Specification

Column 2, Line 56: Please correct "PTTFNQGKLQ" to read --PTTFNQGKLQ--

Column 5, Line 27: Please correct "(xxi; SEQ ID NO:257)" to read --(xx1; SEQ ID NO:257)--

Column 9, Lines 36-37: Please correct "NC 001829, NC 001862, NC 000883," to read --NC_001829, NC_001862, NC_000883,--

Column 9, Line 37: Please correct "NC 001510, NC 006152," to read --NC_001510, NC_006152,--

Column 9, Line 40: Please correct "NC 001358," to read --NC_001358,--

Column 10, Line 44: Please correct "n-islet" to read --β-islet--

Column 15, Line 2: Please correct "PGTFNGGKLW" to read --PGTFNGGKLW--

Column 15, Line 3: Please correct "PGTFNGGKLA" to read --PGTFNGGKLA--

Column 15, Line 14: Please correct "PTTFNPSKLW" to read --PTTFNPSKLW--

Column 15, Line 15: Please correct "PTTFNQGKLQ" to read --PTTFNQGKLQ--

Column 17, Line 4: Please correct "a AV" to read --AAV--

Column 17, Line 50: Please correct "PTTFNQGKLQ" to read --PTTFNQGKLQ--

Column 17, Line 67: Please correct "P6611" to read --P661I--

Signed and Sealed this
Twenty-third Day of September, 2025

John A. Squires
*Director of the United States Patent and Trademark Office*

CERTIFICATE OF CORRECTION (continued)
U.S. Pat. No. 12,281,320 B2

Column 18, Line 2: Please correct "T6621" to read --T662I--

Column 18, Line 34: Please correct "<u>P</u>TTFNQGKLQ" to read --<u>P</u>TTFN<u>Q</u>GKLQ--

Column 18, Line 36: Please correct "RST<u>F</u>NGDKLN" to read --RSTFNGDKL<u>N</u>--

Column 25, Line 8: Please correct "ρ" to read --β--

Column 41, Line 62: Please correct "(al-antitrypsin)" to read --(αl-antitrypsin)--

Column 42, Line 10: Please correct "IIC" to read --I1C--

Column 46, Line 10: Please correct "ADK1α" to read --ADK1a--

Column 46, Line 34: Please correct "ADK1α" to read --ADK1a--

Column 62, Line 11: Please correct "Anti-AA V" to read --Anti-AAV--

Column 62, Line 38: Please correct "anti-AAVMAbs:" to read --anti-AAV MAbs:--

Column 75, SEQ ID NO: 10: Please correct "AA088183" to read --AAO88183--

Column 81, SEQ ID NO: 16: Please correct "AAV capsid" to read --Bovine AAV capsid--

Column 81, SEQ ID NO: 17: Please correct "AAV ATCC" to read --Avian AAV ATCC--

Column 81, Line 62: Please correct "tynnhlykqi ssastgasnd nhyfgystpw" to read --tynnhlykqi ssastgasnd nhyfgystpw--

Column 82, Line 56: Please correct "mifgkesaga" to read --mifgkesaga--

Column 82, Line 63: Please correct "vdftvdnngl" to read --vdftvdnngl--

Column 83, Line 9: Please correct "tynnhlykqi ssqsgasndn hyfgystpwg" to read --tynnhlykqi ssqsgasndn hyfgystpwg--

Column 83, Line 21: Please correct "ifgkqgsekt" to read --ifgkqgsekt--

Column 83, Line 28: Please correct "dftvdtngvy" to read --dftvdtngvy--

Column 83, Line 41: Please correct "tynnhlykqi ssqsgasndn hyfgystpwg" to read --tynnhlykqi ssqsgasndn hyfgystpwg--

Column 83, Line 51: Please correct "lifgkegtta" to read --lifgkegtta--

CERTIFICATE OF CORRECTION (continued)
U.S. Pat. No. 12,281,320 B2

Column 83, Line 59: Please correct "vdftvdtngv" to read --vdftvdtngv--

Column 84, Line 5: Please correct "ykrlgeslqs ntyngfstpw" to read --ykrlgeslqs ntyngfstpw--

Column 84, Line 16: Please correct "agpkqngnta" to read --agpkqngnta--

Column 84, Line 23: Please correct "wapdaagkyt" to read --wapdaagkyt--

Column 84, Lines 34-35: Please correct "synnhqyrei" to read --synnhqyrei--

Column 84, Line 36: Please correct "ksgsvdgsna nayfgystpw" to read --ksgsvdgsna nayfgystpw--

Column 84, Line 46: Please correct "sqpanpgtta" to read --sqpanpgtta--

Column 84, Line 54: Please correct "fapdstgeyr" to read --fapdstgeyr--

Column 84, Line 66: Please correct "tynnhlykqi ssastgasnd nhyfgystpw" to read --tynnhlykqi ssastgasnd nhyfgystpw--

Column 85, Line 10: Please correct "mifgkesaga" to read --mifgkesaga--

Column 85, Line 17: Please correct "vdftvdnngl" to read --vdftvdnngl--

Column 85, Line 30: Please correct "ptynnhlykq issetagstn dntyfgystp" to read --ptynnhlykq issetagstn dntyfgystp--

Column 85, Line 41: Please correct "gvlifgktga" to read --gvlifgktga--

Column 85, Line 42: Please correct "tnkttlenvl" to read --tnkttlenvl--

Column 85, Line 48: Please correct "gvdfavdsqg vyseprpigt" to read --gvdfavdsqg vyseprpigt--

Column 85, Line 61: Please correct "ptynnhlykq isngtsggat ndntyfgyst" to read --ptynnhlykq isngtsggat ndntyfgyst--

Column 86, Lines 3-4: Please correct "gilifgkqna" to read --gilifgkqna--

Column 86, Line 5: Please correct "ardnadysdv" to read --ardnadysdv--

Column 86, Line 11: Please correct "tsvdfavnte gvyseprpig" to read --tsvdfavnte gvyseprpig--

Column 86, Line 24: Please correct "tynnhlykqi snstsggssn dnayfgystp" to read --tynnhlykqi snstsggssn dnayfgystp--

Column 86, Line 35: Please correct "lifgkqgtgr" to read --lifgkqgtgr--

CERTIFICATE OF CORRECTION (continued)
U.S. Pat. No. 12,281,320 B2

Column 86, Line 42: Please correct "vefavntegv" to read --vefavntegv--

Column 86, Line 55: Please correct "ptynnhlykq isngtsggst ndntyfgyst" to read --ptynnhlykq isngtsggst ndntyfgyst--

Column 86, Line 65: Please correct "gvlmfgkqga" to read --gvlmfgkqga--

Column 86, Line 66: Please correct "gkdnvdyssv" to read --gkdnvdyssv--

Column 87, Line 5: Please correct "tnvdfavntd gtyseprpig" to read --tnvdfavntd gtyseprpig--

Column 87, Line 7-Column 88, Line 33: Please delete SEQ ID NOs:28, 29 and 30 and replace with the following:

Example of AAV11 VP1 capsid protein sequence
maadgylpdwlednlsegirewwdlkpgapkpkanqqkqddgrglvlpgykylgpfngldkgepvnaadaaalehdkaydqqlkagd npylrynhadaefqerlqedtsfggnlgravfqakkrvleplglveegaktapgkkrplespqepdsssgigkkgkqparkrlnfeedtgagd gppegsdtsamssdiemraapggnavdagqgsdgvgnasgdwhcdstwsegkvtttstrtwvlptynnhlylrlgttsssntyngfstpw gyfdfnrfhchfsprdwqrlinnnwglrpkamrvkifniqvk<u>evttsngettvann</u>ltstvqifadssyelpyvmdagqegslppfpndvfm vpqygycgivtgenqnqtdrnafycleyfpsqmlrtgnnfemaynfekvpfhsmyahsqsldrlmnplldqylwhlqsttsgetlnqgnaa ttfgkirsgdfafyrknwlpgpcvkqqrfsktasqnykipasggnallkydthytlnnrwsniapgppmatagpsdgdfsnaqlifpgpsvtg ntttsannllftseeeiaatnprdtdmfgqiadnnqnattapitgnvtamgvlpgmvwqnrdiyyqgpiwakiphadghfhpspliggfglk hpppqifikntpvpanp*ATTFTAARVD*sfitqystgqvavqieweiekerskrwnpevqftsnygnqssmlwapdttgkyteprvig sryltnhl (SEQ ID NO:28)

Example of AAV12 VP1 capsid protein sequence
maadgylpdwlednlsegirewwalkpgapqpkanqqhqdngrglvlpgykylgpfngldkgepvneadaaalehdkaydkqleqgd npylkynhadaefqqrlatdtsfggnlgravfqakkrileplglveegvktapgkkrplektpnrptnpdsgkapakkkqkdgepadsarrtl dfedsgagdgppegsssgemshdaemraapggnaveagqgadgvgnasgdwhcdstwsegrvtttstrtwvlptynnhlylrigttans ntyngfstpwgyfdfnrfhchfsprdwqrlinnnwglrpksmrvkifniqvk<u>evttsngettvann</u>ltstvqifadstyelpyvmdagqegsf ppfpndvfmvpqygycgvvtgknqnqtdrnafycleyfpsqmlrtgnnfevsyqfekvpfhsmyahsqsldrmmnplldqywhlqstt tgnslnqgtatttygkittgdfayyrknwlpgacikqqkfsknanqnykipasggdallkydthttlngrwsnmapgppmatagagdsdfsn sqlifagpnpsgntttssnnllftseeeiattnprdtdmfgqiadnnqnattaphianldamgivpgmvwqnrdiyyqgpiwakvphtdghf hpsplmggfglkhpppqifikntpvpanp*NTTFSAARIN*sfltqystgqvavqidweiqkehskrwnpevqftsnygtqnsmlwap dnagnyhelraigsrflthhl (SEQ ID NO:29)

Example of AAV13 VP1 capsid protein sequence
mtdgylpdwlednlsegvrewwalqpgapkpkanqqhqdnarglvlpgykylgpgngldkgepvnaadaaalehdkaydqqlkagdn pylkynhadaefqerlqedtsfggnlgravfqakkrileplglveeaaktapgkkrpveqspaepdsssgigksgqqparkrlnfgqtgdtesv pdpqplgqppaapsgvgsttmasgggapmadnnegadvgnssgnwhcdsqwlgdrvittstrtwalptynnhlykqissqsgatndn hyfgystpwgyfdfnrfhchfsprdwqrlinnnwgfrpkrlnfklfniqvk<u>evtqndgtttiann</u>ltstvqvftdseyqlpyvlgsahqgclpp fpadvfmvpqygyltlnngsqavgrssfycleyfpsqmlrtgnnfqfsytfedvpfhssyahsqsldrlmnplidqylyylnrtqtasgtqqsr llfsqagptsmslqaknwlpgpcyrqqrlskqandnnnsnfpwtgatkyhlngrdslvnpgpamashkddkekffpmhgtlifgkegtna nnadlenvmitdeeeirttnpvateqygtvsnnlqnsnagpttgtvnhqgalpgmvwqdrdvylqgpiwakiphtdghfhpsplmggfgl khpppqimikntpvpanp*PTNFSAAKFA*sfitqystgqvsveiewelqkenskrwnpeiqytsnynksvnvdftvdtngvyseprpi gtryltrnl (SEQ ID NO:30)